US012053470B2

(12) United States Patent
Alghalandis et al.

(10) Patent No.: US 12,053,470 B2
(45) Date of Patent: Aug. 6, 2024

(54) PHARMACEUTICAL COMBINATION COMPRISING AN ALK INHIBITOR AND A SHP2 INHIBITOR

(71) Applicants: Novartis AG, Basel (CH); The General Hospital Corporation, Boston, MA (US)

(72) Inventors: Leila Dardaei Alghalandis, Malden, MA (US); Jeffrey Adam Engelman, Chestnut Hill, MA (US); Huaixiang Hao, Lexington, MA (US); Matthew J. Lamarche, Reading, MA (US); Fang Li, Lexington, MA (US); Hui-Qin Wang, Lexington, MA (US)

(73) Assignees: NOVARTIS AG, Basel (CH); THE GENERAL HOSPITAL CORPORATION, Boston, MA (US)

( * ) Notice: Subject to any disclaimer, the term of this patent is extended or adjusted under 35 U.S.C. 154(b) by 46 days.

(21) Appl. No.: 17/714,996

(22) Filed: Apr. 6, 2022

(65) Prior Publication Data

US 2022/0241277 A1    Aug. 4, 2022

Related U.S. Application Data

(63) Continuation of application No. 16/475,982, filed as application No. PCT/IB2018/050111 on Jan. 8, 2018, now abandoned.

(60) Provisional application No. 62/444,493, filed on Jan. 10, 2017.

(51) Int. Cl.

| | | |
|---|---|---|
| *A61K 31/506* | (2006.01) | |
| *A61K 31/4545* | (2006.01) | |
| *A61K 31/497* | (2006.01) | |
| *A61K 31/519* | (2006.01) | |
| *A61K 31/53* | (2006.01) | |
| *A61K 31/5377* | (2006.01) | |
| *A61P 35/00* | (2006.01) | |

(52) U.S. Cl.
CPC ........ *A61K 31/506* (2013.01); *A61K 31/4545* (2013.01); *A61K 31/497* (2013.01); *A61K 31/519* (2013.01); *A61K 31/53* (2013.01); *A61K 31/5377* (2013.01); *A61P 35/00* (2018.01)

(58) Field of Classification Search
CPC .............. A61K 31/506; A61K 31/4545; A61K 31/497; A61K 31/519; A61K 31/53; A61K 31/5377; A61K 2300/00; A61P 35/00

See application file for complete search history.

(56) References Cited

U.S. PATENT DOCUMENTS

| 4,613,603 | A | 9/1986 | Biziere et al. |
|---|---|---|---|
| 9,296,721 | B1 | 3/2016 | Xu |
| 9,567,318 | B2 | 2/2017 | Chiosis et al. |
| 9,815,813 | B2 | 11/2017 | Chen et al. |
| 10,077,276 | B2 | 9/2018 | Chen et al. |
| 10,093,646 | B2 | 10/2018 | Chen et al. |
| 10,287,266 | B2 | 5/2019 | Chen et al. |
| 10,301,278 | B2 | 5/2019 | Chen et al. |
| 10,308,660 | B2 | 6/2019 | Chen et al. |
| 10,336,774 | B2 | 7/2019 | Chen et al. |
| 2003/0171359 | A1 | 9/2003 | Dahmann et al. |
| 2004/0229873 | A1 | 11/2004 | Harbige et al. |
| 2005/0222159 | A1 | 10/2005 | Tsutsumi et al. |
| 2006/0183911 | A1 | 8/2006 | Charrier et al. |
| 2008/0024964 | A1 | 1/2008 | Lev et al. |
| 2010/0029941 | A1 | 2/2010 | Wallace et al. |
| 2011/0257184 | A1 | 10/2011 | Qu et al. |
| 2011/0306606 | A1 | 12/2011 | Ryu et al. |
| 2011/0319381 | A1 | 12/2011 | Abouabdellah et al. |
| 2012/0190699 | A1 | 7/2012 | Charrier et al. |
| 2012/0252818 | A1 | 10/2012 | Chiosis et al. |
| 2013/0116430 | A1 | 5/2013 | Fujiwara et al. |
| 2013/0184259 | A1 | 7/2013 | Charrier et al. |
| 2015/0315207 | A1 | 11/2015 | Morales et al. |
| 2017/0001975 | A1 | 1/2017 | Chen et al. |
| 2017/0015680 | A1 | 1/2017 | Chen et al. |
| 2018/0065949 | A1 | 3/2018 | Chen et al. |
| 2018/0186770 | A1 | 7/2018 | Chen et al. |
| 2018/0201623 | A1 | 7/2018 | Chen et al. |
| 2018/0251471 | A1 | 9/2018 | Chen et al. |

(Continued)

FOREIGN PATENT DOCUMENTS

| CN | 102753177 A | 10/2012 |
|---|---|---|
| EP | 0 459 819 A2 | 12/1991 |
| EP | 0 799 617 A2 | 10/1997 |

(Continued)

OTHER PUBLICATIONS

Shaw, Ceritinib: A potent second-genreation ALK inhibitor for non-small-cell lung cancer. Advances at Mass General Cancer Center (Year: 2014).*

(Continued)

*Primary Examiner* — Barbara P Badio
(74) *Attorney, Agent, or Firm* — LATHROP GPM LLP; Brian C. Trinque

(57) ABSTRACT

A pharmaceutical combination comprising an ALK inhibitor, in free form or a pharmaceutically acceptable salt thereof, and a SHP2 inhibitor, in free form or a pharmaceutically acceptable salt thereof, and optionally a pharmaceutically acceptable carrier, for simultaneous or sequential administration; the uses of such combination in the treatment of proliferative diseases; and methods of treating a subject suffering from a proliferative disease comprising administering a therapeutically effective amount of such combination.

7 Claims, 4 Drawing Sheets

Specification includes a Sequence Listing.

(56) References Cited

U.S. PATENT DOCUMENTS

| | | |
|---|---|---|
| 2018/0362496 A1 | 12/2018 | Chen et al. |
| 2019/0185475 A1 | 6/2019 | Bagdanoff et al. |

FOREIGN PATENT DOCUMENTS

| | | |
|---|---|---|
| JP | H06340634 A | 12/1994 |
| WO | WO 1991/019305 A1 | 12/1991 |
| WO | WO 2000/059893 A1 | 10/2000 |
| WO | WO 2002/024679 A1 | 3/2002 |
| WO | WO 2005/117909 A2 | 12/2005 |
| WO | WO 2006/065946 A1 | 6/2006 |
| WO | WO 2007/031529 A1 | 3/2007 |
| WO | WO 2008/055959 A1 | 5/2008 |
| WO | WO 2008/100412 A1 | 8/2008 |
| WO | WO 2008/110611 A1 | 9/2008 |
| WO | WO 2009/131687 A2 | 10/2009 |
| WO | WO 2009/150230 A1 | 12/2009 |
| WO | WO 2009/158571 A1 | 12/2009 |
| WO | WO 2010/008739 A2 | 1/2010 |
| WO | WO 2010/011666 A2 | 1/2010 |
| WO | WO 2010/048149 A2 | 4/2010 |
| WO | WO 2010/121212 A2 | 10/2010 |
| WO | WO 2011/022440 A3 | 2/2011 |
| WO | WO 2011/078143 A1 | 6/2011 |
| WO | WO 2012/009217 A1 | 1/2012 |
| WO | WO 2012/016217 A1 | 2/2012 |
| WO | WO 2012/027495 A1 | 3/2012 |
| WO | WO 2012/052948 A1 | 4/2012 |
| WO | WO 2013/040044 A1 | 3/2013 |
| WO | WO 2013/096093 A1 | 6/2013 |
| WO | WO 2013/174876 A1 | 11/2013 |
| WO | WO 2013/182546 A1 | 12/2013 |
| WO | WO 2014/054053 A1 | 4/2014 |
| WO | WO 2014/160521 A1 | 10/2014 |
| WO | WO 2015/050344 A1 | 4/2015 |
| WO | WO 2015/092819 A2 | 6/2015 |
| WO | WO 2015/107493 A1 | 7/2015 |
| WO | WO 2015/107494 A1 | 7/2015 |
| WO | WO 2015/107495 A1 | 7/2015 |
| WO | WO 2015/168466 A1 | 11/2015 |
| WO | WO 2016/023404 A1 | 2/2016 |
| WO | WO 2016/032927 A1 | 3/2016 |
| WO | WO 2016/203404 A1 | 12/2016 |
| WO | WO 2016/203405 A1 | 12/2016 |
| WO | WO 2016/203406 A1 | 12/2016 |
| WO | WO 2017/156397 A1 | 9/2017 |
| WO | WO2017156397 * | 9/2017 |
| WO | WO 2017/216706 A1 | 12/2017 |
| WO | WO 2018/057884 A1 | 3/2018 |
| WO | WO 2018/081091 A1 | 5/2018 |

OTHER PUBLICATIONS

Aso et al., "Discovery of pyrrolo[2,3-d]pyrimidin-4-ones as corticotropin-releasing factor 1 receptor antagonists with a aarbonyl-based hydrogen bonding acceptor", Bioorganic & Medicinal Chemistry Letters, 21:2365-2371 (2011).

Cancer [online], [retrieved on Jul. 6, 2007]. Retrieved from the internet, URL <http://www.nim.nih.gov/medlineplus/cancer.html>.

Crystal et al., "Patient-derived models of acquired resistance can identify effective drug combinations for cancer", Cancer Therapy 346(6216):1480-1486 (2014).

Dardaei et al., "Abstract 1007: SHP2 inhibition restores sensitivity to ALK inhibition in resistant ALK-rearranged non-small cell lung cancer (NSCLC)", Cancer Research 77(13 Supplement 1) (2017).

Dardaei et al., "Abstract A145: SHP2 inhibition restores sensitivity to ALK inhibitors in resistant ALK-rearranged NSCLC", Molecular Cancer Therapeutics 17(1 Supplement) (2018).

Ellingboe et al., "(Pyrimidinyloxy)acetic Acids and Pyrimidineacetic Acids as a Novel Class of Aldose Reductase Inhibitors", Journal of Medicinal Chemistry 33:2892-2899 (1990).

Fortanet et al., "Allosteric Inhibition of SHP2: Identification of a Potent, Selective, and Orally Efficacious Phosphatase Inhibitor", Journal of Medicinal Chemistry 59:7773-7782 (2016).

Friboulet et al., "The ALK Inhibitor Ceritinib Overcomes Crizotinib Resistance in Non-Small Cell Lung Cancer", Cancer Discovery 4(6):662-673 (2014).

Golub et al., "Molecular Classification of Cancer: Class Discovery and Class Prediction by Gene Expression Monitoring", Science 286(5439):531-537 (1999).

Hussein et al., "Pharmacokinetics of 619C89, a novel neuronal sodium channel inhibitor, in acute stroke patients after loading and discrete maintenance infusions", British Journal of Clinical Pharmacology 41(6):505-511 (1996).

International Search Report and Written Opinion for International Application No. PCT/IB2018/050111, mailed Jun. 5, 2018, 19 pages.

Lala et al., "Role of nitric oxide in tumor progression: Lessons from experimental tumors", Cancer and Metastasis Reviews 17(1):91-106 (1998).

Large et al., "The relationship between sodium channel inhibition and anticonvulsant activity in a model of generalised seizure in the rat", Epilepsy Research 85(1):96-106 (2009).

Nair et al., "A simple practice guide for dose conversion between animals and human," Journal of Basic and Clinical Pharmacy 7(2):27-31 (2016).

Palmer et al., "The Role of Sodium Channels in Disease", Drug News & Perspectives 14(9):568-576 (2001).

Prahallad et al., "PTPN11 is a Central Node in Intrinsic and Acquired Resistance to Targeted Cancer Drugs", Cell Reports 12(12):1978-1985 (2015).

RN 1115905-67-3, Database Registry [Online], Mar. 5, 2009, Retrieved from STN.

RN 1115905-69-5, Database Registry [Online], Mar. 5, 2009, Retrieved from STN.

RN 1115905-70-8, Database Registry [Online], Mar. 5, 2009, Retrieved from STN.

RN 1115976-35-6, Database Registry [Online], Mar. 5, 2009, Retrieved from STN.

RN 1115976-39-0, Database Registry [Online], Mar. 5, 2009, Retrieved from STN.

RN 1326879-96-2, Database Registry [Online], Sep. 2, 2011, Retrieved from STN.

RN 1326894-16-9, Database Registry [Online], Sep. 2, 2011, Retrieved from STN.

RN 1326900-40-6, Database Registry [Online], Sep. 2, 2011, Retrieved from STN.

RN 1326924-17-7, Database Registry [Online], Sep. 2, 2011, Retrieved from STN.

Tsutsumi et al., "Off-target inhibition by active site-targeting SHP2 inhibitors", FEBS Open Bio 8(9):1405-1411 (2018).

Whelligan et al., "Aminopyrazine Inhibitors Binding to an Unusual Inactive Conformation of the Mitotic Kinase Nek2: SAR and Structural Characterization", Journal of Medicinal Chemistry 53(21):7682-7698 (2010).

Zykadia Capsules 150mg, Pharmaceutical Interview Form, 1$^{st}$ Edition, Novartis Pharma K.K., Mar. 2016.

* cited by examiner

SEQUENCE LISTING

<160> NUMBER OF SEQ ID NOS: 1

<210> SEQ ID NO 1
<211> LENGTH: 20
<212> TYPE: PRT
<213> ORGANISM: Artificial Sequence
<220> FEATURE:
<223> OTHER INFORMATION: biphosphorylated peptide derived from insulin
      receptor substrate-1 (IRS-1)
<220> FEATURE:
<221> NAME/KEY: MOD_RES
<222> LOCATION: (3)..(3)
<223> OTHER INFORMATION: PHOSPHORYLATED TYROSINE
<220> FEATURE:
<221> NAME/KEY: MOD_RES
<222> LOCATION: (9)..(10)

```
<223> OTHER INFORMATION: Pegylated (dPEG8) between valine residue 9 and
      leucine residue 10
<220> FEATURE:
<221> NAME/KEY: MOD_RES
<222> LOCATION: (13)..(13)
<223> OTHER INFORMATION: PHOSPHORYLATED TYROSINE
<220> FEATURE:
<221> NAME/KEY: MOD_RES
<222> LOCATION: (20)..(20)
<223> OTHER INFORMATION: AMIDATED Lysine

<400> SEQUENCE: 1

Leu Asn Tyr Ile Asp Leu Asp Leu Val Leu Ser Thr Tyr Ala Ser Ile
1               5                   10                  15

Asn Phe Gln Lys
            20
```

PHARMACEUTICAL COMBINATION COMPRISING AN ALK INHIBITOR AND A SHP2 INHIBITOR

This application is a continuation of U.S. patent application Ser. No. 16/475,982 filed on Jul. 3, 2019, which is a 371 U.S. national phase application of international application number PCT/IB2018/050111, filed Jan. 8, 2018, which application claims priority to U.S. Provisional Application No. 62/444,493, filed Jan. 10, 2017, each of which is incorporated by reference herein in their entirety.

FIELD OF THE INVENTION

The present invention relates to a pharmaceutical combination comprising an anaplastic lymphoma kinase (ALK) inhibitor as one of the combination partners, the uses of such a combination in the treatment of proliferative diseases, such as cancer, in particular non-small cell lung cancer (NSCLC); and methods of treating a subject suffering from a proliferative disease, such as cancer, in particular non-small cell lung cancer, comprising administering a therapeutically effective amount of such a combination.

BACKGROUND OF THE INVENTION

Highly potent and selective inhibitors targeting anaplastic lymphoma kinase (ALK)-rearranged lung cancer have been used to treat patients suffering from non-small cell lung cancer (NSCLC). However, in spite of these treatment options cases of resistance occur. The resistance to the selective inhibitors can develops through a variety of mechanisms, such as for example through secondary mutations in ALK, or activation of a compensatory signaling pathway. Thus, there remains a need for effective and safe therapeutic agents to treat such cases of resistance.

SUMMARY OF THE INVENTION

The invention provides pharmaceutical combinations and therapeutic methods which may be useful for treating cancer, particularly ALK-rearranged (i.e. ALK-positive) cancer, such as for example non-small cell lung cancers (NSCLCs). The cancer can also be resistant to an ALK inhibitor; for example due to activated bypass signaling pathways (off-target resistance). We found that co-targeting of ALK and SHP2 amplifies the anti-proliferative effect of an ALK inhibitor, even in an ALK resistant cancer. We found that methods involving co-targeting ALK and SHP2 using a combination of an ALK inhibitor and a SHP2 inhibitor decrease RAS-GTP loading potential of cells and inhibit phospho-ERK rebound, which can even overcome off-target resistance in ALK-rearranged cancer such as NSCLC.

The present invention provides the following aspects, advantageous features and specific embodiments, respectively alone or in combination, as listed in the following items:

Item 1: A pharmaceutical combination comprising:
(i) an ALK inhibitor or a pharmaceutically acceptable salt thereof, and
(ii) a SHP2 inhibitor, or a pharmaceutically acceptable salt thereof.

Item 2: The pharmaceutical combination of item 1, further comprising at least one pharmaceutically acceptable carrier.

Item 3: A pharmaceutical composition comprising a pharmaceutical combination of 1 or 2 and at least one pharmaceutically acceptable carrier.

Item 4: The pharmaceutical combination of item 1 or 2, or the pharmaceutical composition of item 3, wherein the ALK inhibitor or a pharmaceutically acceptable salt thereof and the SHP2 inhibitor or a pharmaceutically acceptable salt thereof are provided in jointly therapeutically effective amounts for use in the treatment of cancer.

Item 5: The pharmaceutical combination of item 4, or the pharmaceutical composition of item 4, wherein the ALK inhibitor or a pharmaceutically acceptable salt thereof and the SHP2 inhibitor or a pharmaceutically acceptable salt thereof are provided in synergistically effective amounts for use in the treatment of cancer.

Item 6: A commercial package comprising a pharmaceutical combination or pharmaceutical composition of any one of items 1 to 5 together with instructions for simultaneous or sequential administration thereof for use in the treatment of cancer.

Item 7: The pharmaceutical combination of item 4 or 5, the pharmaceutical composition of item 4 or 5, or the commercial package of item 6, wherein the cancer is an ALK-positive cancer.

Item 8: The pharmaceutical combination or pharmaceutical composition according item 4 or item 5, or the commercial package of item 6, wherein the cancer is ALK-positive cancer selected from anaplastic large-cell lymphoma, gastric cancer, breast cancers, oesophageal cancer, colorectal cancer, neuroblastoma, inflammatory myofibroblastic tumor, renal cancer, pancreatic cancer and lung cancer.

Item 9: The pharmaceutical combination or pharmaceutical composition according item 4 or item 5, or the commercial package of item 6, wherein the cancer is ALK-positive non-small cell lung cancer.

Item 10: The pharmaceutical combination or pharmaceutical composition according item 4 or item 5, or the commercial package of item 6, wherein the cancer is ALK-positive neuroblastoma.

Item 11: The pharmaceutical combination or pharmaceutical composition according item 4 or item 5, or the commercial package of item 6.

Item 12: The pharmaceutical combination or pharmaceutical composition according item 4 or item 5, or the commercial package of item 6, wherein the cancer is an ALK-positive cancer resistant to the ALK inhibitor of the pharmaceutical combination.

Item 13: The pharmaceutical combination or pharmaceutical composition according item 4 or item 5, or the commercial package of item 6, wherein the cancer is an ALK-positive cancer characterized by ALK-independent resistance to an ALK inhibitor.

Item 14: The pharmaceutical combination of item 1 or 2, the pharmaceutical composition of item 3 or the commercial package of item 6, for use as a medicament.

Item 15: The pharmaceutical combination of item 1 or 2, the pharmaceutical composition of item 3 or the commercial package of item 6, for use in the treatment of cancer.

Item 16: Use of the pharmaceutical combination of item 1 or 2, the pharmaceutical composition of item 3 or the commercial package of item 6, in the manufacture of a medicament for the treatment of cancer.

Item 17: A method of treating a cancer in a subject, comprising administering to said subject a therapeutically effective amount of:
(i) an ALK inhibitor or in pharmaceutically acceptable salt thereof, and
(ii) a SHP2 inhibitor or in pharmaceutically acceptable salt thereof.

Item 18: The pharmaceutical combination for use according to item 15, the pharmaceutical composition for use according to item 15, the commercial package for use according to item 15, use of the pharmaceutical combination according to item 16, use of the pharmaceutical composition according to item 16, use of the commercial package according to item 16, or the method of treating a cancer according to item 17, wherein the cancer is an ALK-positive cancer.

Item 19: The pharmaceutical combination for use according to item 15, the pharmaceutical composition for use according to item 15, the commercial package for use according to item 15, use of the pharmaceutical combination according to item 16, use of the pharmaceutical composition according to item 16, use of the commercial package according to item 16, or the method of treating a cancer according to item 17, wherein the cancer is ALK-positive cancer selected from anaplastic large-cell lymphoma, gastric cancer, breast cancers, oesophageal cancer, colorectal cancer, neuroblastoma, inflammatory myofibroblastic tumor, renal cancer, pancreatic cancer and lung cancer.

Item 20: The pharmaceutical combination for use according to item 15, the pharmaceutical composition for use according to item 15, the commercial package for use according to item 15, use of the pharmaceutical combination according to item 16, use of the pharmaceutical composition according to item 16, use of the commercial package according to item 16, or the method of treating a cancer according to item 17, wherein the cancer is ALK-positive non-small cell lung cancer.

Item 21: The pharmaceutical combination for use according to item 15, the pharmaceutical composition for use according to item 15, the commercial package for use according to item 15, use of the pharmaceutical combination according to item 16, use of the pharmaceutical composition according to item 16, use of the commercial package according to item 16, or the method of treating a cancer according to item 17, wherein the cancer is ALK-positive neuroblastoma.

Item 22: The pharmaceutical combination for use according to item 15, the pharmaceutical composition for use according to item 15, the commercial package for use according to item 15, use of the pharmaceutical combination according to item 16, use of the pharmaceutical composition according to item 16, use of the commercial package according to item 16, or the method of treating a cancer according to item 17, wherein the cancer is an ALK-positive cancer resistant to an ALK inhibitor.

Item 23: The pharmaceutical combination for use according to item 15, the pharmaceutical composition for use according to item 15, the commercial package for use according to item 15, use of the pharmaceutical combination according to item 16, use of the pharmaceutical composition according to item 16, use of the commercial package according to item 16, or the method of treating a cancer according to item 17, where the cancer is an ALK-positive cancer resistant to the ALK inhibitor of the pharmaceutical combination.

Item 24: The pharmaceutical combination for use according to item 15, the pharmaceutical composition for use according to item 15, the commercial package for use according to item 15, use of the pharmaceutical combination according to item 16, use of the pharmaceutical composition according to item 16, use of the commercial package according to item 16, or the method of treating a cancer according to item 17, wherein the cancer is an ALK-positive cancer characterized by ALK-independent resistance to an ALK inhibitor.

Item 25: The pharmaceutical combination of item 1 or item 2, the pharmaceutical composition of item 3, the commercial package of item 6, the pharmaceutical combination for use according to any one of items 4, 5, 7 to 15 or 18 to 24, the pharmaceutical composition for use according to any one of items 4, 5, 7 to 15 or 18 to 24, the commercial package for use according to any one of items 4, 5, 7 to 15 or 18 to 24, use of the pharmaceutical combination according to any one of items 16 or 18 to 24, use of the pharmaceutical composition according to any one of items 16 or 18 to 24, use of the commercial package according to any one of items 16 or 18 to 24, or the method of treating a cancer according to any one of items 17 to 24, wherein the ALK inhibitor is selected from 5-chloro-N2-[2-isopropoxy-5-methyl-4-(4-piperidinyl)phenyl]-N4-[2-(isopropylsulfonyl)phenyl]-2,4-pyrimidinediamine (ceritinib), (10R)-7-Amino-12-fluoro-2,10,16-trimethyl-15-oxo-10,15,16,17-tetrahydro-2H-8,4-(metheno)pyrazolo[4,3-h][2,5,11]-benzoxadiazacyclotetradecine-3-carbonitrile (lorlatinib; PF-06463922),

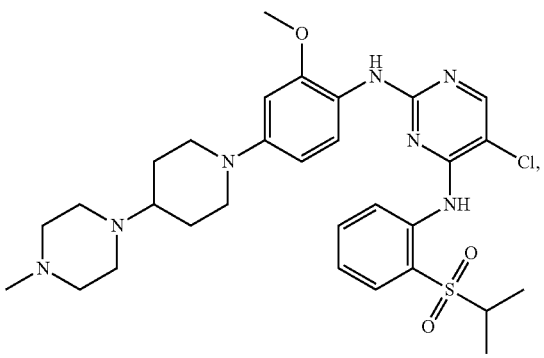

TAE684

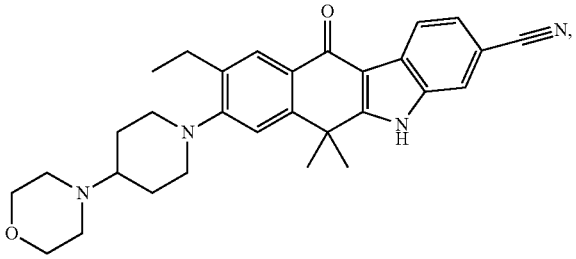

Alectinib

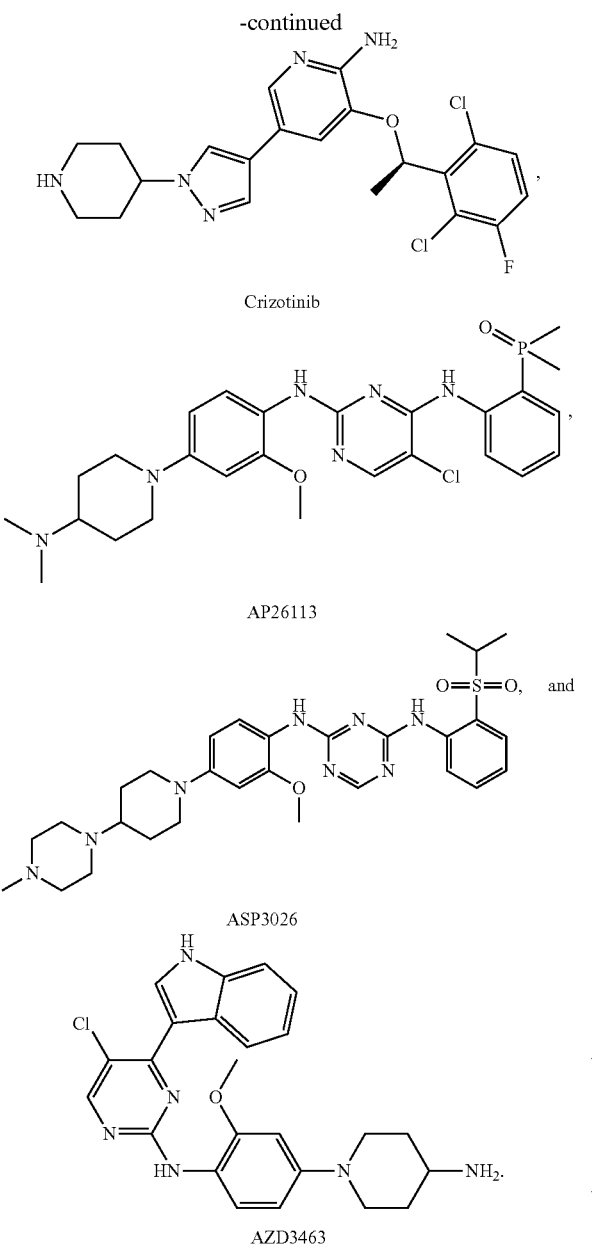

Item 26: The pharmaceutical combination of item 1 or item 2, the pharmaceutical composition of item 3, the commercial package of item 6, the pharmaceutical combination for use according to any one of items 4, 5, 7 to 15 or 18 to 24, the pharmaceutical composition for use according to any one of items 4, 5, 7 to 15 or 18 to 24, the commercial package for use according to any one of items 4, 5, 7 to 15 or 18 to 24, use of the pharmaceutical combination according to any one of items 16 or 18 to 24, use of the pharmaceutical composition according to any one of items 16 or 18 to 24, use of the commercial package according to any one of items 16 or 18 to 24, or the method of treating a cancer according to any one of items 17 to 24, wherein the ALK inhibitor is selected from 5-chloro-N2-[2-isopropoxy-5-methyl-4-(4-piperidinyl)phenyl]-N4-[2-(isopropylsulfonyl)phenyl]-2,4-pyrimidinediamine (ceritinib).

Item 27: The pharmaceutical combination according to any one of items 1, 2, 25 or 26, the pharmaceutical composition according to any one of items 3, 25 or 26, the commercial package to any one of items 6, 25 or 26, the pharmaceutical combination for use according to any one of items 4, 5, 7 to 15 or 18 to 26, the pharmaceutical composition for use according to any one of items 6, the commercial package for use according to any one of items 14, 15 or 18 to 26, use of the pharmaceutical combination according to any one of items 16 or 18 to 26, use of the pharmaceutical composition according to any one of items 16 or 18 to 26, use of the commercial package according to any one of items 16 or 18 to 26, or the method of treating a cancer according to any one of items 17 to 26, wherein the SHP2 inhibitor is selected from a SHP2 inhibitor of Table 1.

Item 28: The pharmaceutical combination of item 1 or item 2, the pharmaceutical composition of item 3, the commercial package of item 6, the pharmaceutical combination for use according to any one of items 4, 5, 7 to 15 or 18 to 24, the pharmaceutical composition for use according to any one of items 4, 5, 7 to 15 or 18 to 24, the commercial package for use according to any one of items 4, 5, 7 to 15 or 18 to 24, use of the pharmaceutical combination according to any one of items 16 or 18 to 24, use of the pharmaceutical composition according to any one of items 16 or 18 to 24, use of the commercial package according to any one of items 16 or 18 to 24, or the method of treating a cancer according to any one of items 17 to 24, wherein:
a) the ALK inhibitor is 5-chloro-N2-[2-isopropoxy-5-methyl-4-(4-piperidinyl)phenyl]-N4-[2-(isopropylsulfonyl)phenyl]-2,4-pyrimidinediamine (ceritinib) and the SHP2 inhibitor is 6-(4-amino-4-methylpiperidin-1-yl)-3-(2,3-dichlorophenyl)pyrazin-2-amine; or
b) the ALK inhibitor is 5-chloro-N2-[2-isopropoxy-5-methyl-4-(4-piperidinyl)phenyl]-N4-[2-(isopropylsulfonyl)phenyl]-2,4-pyrimidinediamine (ceritinib) and the SHP2 inhibitor is 6-(4-(aminomethyl)-4-phenylpiperidin-1-yl)-3-(2,3-dichlorophenyl)pyrazin-2-amine; or
c) the ALK inhibitor is 5-chloro-N2-[2-isopropoxy-5-methyl-4-(4-piperidinyl)phenyl]-N4-[2-(isopropylsulfonyl)phenyl]-2,4-pyrimidinediamine (ceritinib) and the SHP2 inhibitor is 6-(4-(aminomethyl)-4-methylpiperidin-1-yl)-3-(2,3-dichlorophenyl)pyrazin-2-amine; or
d) the ALK inhibitor is 5-chloro-N2-[2-isopropoxy-5-methyl-4-(4-piperidinyl)phenyl]-N4-[2-(isopropylsulfonyl)phenyl]-2,4-pyrimidinediamine (ceritinib) and the SHP2 inhibitor is 6-(4-(aminomethyl)-4-methylpiperidin-1-yl)-3-((2-(trifluoromethyl)pyridin-3-yl)thio)pyrazin-2-amine; or
e) the ALK inhibitor is 5-chloro-N2-[2-isopropoxy-5-methyl-4-(4-piperidinyl)phenyl]-N4-[2-(isopropylsulfonyl)phenyl]-2,4-pyrimidinediamine (ceritinib) and the SHP2 inhibitor is (R)-8-(6-amino-5-((2-(trifluoromethyl)pyridin-3-yl)thio)pyrazin-2-yl)-8-azaspiro[4.5]decan-1-amine; or
f) the ALK inhibitor is 5-chloro-N2-[2-isopropoxy-5-methyl-4-(4-piperidinyl)phenyl]-N4-[2-(isopropylsulfonyl)phenyl]-2,4-pyrimidinediamine (ceritinib) and the SHP2 inhibitor is (R)-8-(6-amino-5-((2-amino-3-chloropyridin-4-yl)thio)pyrazin-2-yl)-8-azaspiro[4.5]decan-1-amine; or g) the ALK inhibitor is 5-chloro-N2-[2-isopropoxy-5-methyl-4-(4-piperidinyl)phenyl]-N4-[2-(isopropylsulfonyl)phenyl]-2,4-pyrimidinediamine (ceritinib) and the SHP2 inhibitor is (3S,4S)-8-(6-amino-5-(2,3-dichlorophenyl)pyrazin-2-yl)-3-methyl-2-oxa-8-azaspiro[4.5]decan-4-amine; or h) the ALK inhibitor is 5-chloro-N2-[2-isopropoxy-5-methyl-4-(4-piperidinyl)phenyl]-N4-[2-(isopropylsulfonyl)phenyl]-2,4-pyrimidinediamine (ceritinib) and the SHP2 3-(2,3-dichlorophenyl)-6-(1,8-diazaspiro[4.5]decan-8-yl)pyrazin-2-amine; or i) the ALK inhibitor is 5-chloro-N2-[2-isopropoxy-5-methyl-4-(4-piperidinyl)phenyl]-N4-[2-(isopropylsulfonyl)phenyl]-2,4-pyrimidinediamine (ceritinib) and the SHP2 inhibitor is (R)-8-(6-amino-5-(2,3-dichlorophenyl)pyrazin-2-yl)-8-azaspiro[4.5]decan-1-amine; or j) the ALK inhibitor is 5-chloro-N2-[2-isopropoxy-5-methyl-4-(4-piperidinyl)phenyl]-N4-[2-(isopropylsulfonyl)phenyl]-2,4-pyrimidinediamine (ceritinib) and the SHP2 inhibitor is (S)-8-(6-amino-5-((2-(trifluoromethyl)pyridin-3-yl)thio)pyrazin-2-yl)-2-oxa-8-azaspiro[4.5]decan-4-amine; or k) the ALK inhibitor is 5-chloro-N2-[2-isopropoxy-5-methyl-4-(4-piperidinyl)phenyl]-N4-[2-(isopropylsulfonyl)phenyl]-2,4-pyrimidinediamine (ceritinib) and the SHP2 inhibitor is (S)-8-(6-amino-5-((2-amino-3-chloropyridin-4-yl)thio)pyrazin-2-yl)-2-oxa-8-azaspiro[4.5]decan-4-amine; or l) the ALK inhibitor is 5-chloro-N2-[2-isopropoxy-5-methyl-4-(4-piperidinyl)phenyl]-N4-[2-(isopropylsulfonyl)phenyl]-2,4-pyrimidinediamine (ceritinib) and the SHP2 inhibitor is (1R,3R)-8-(6-amino-5-((2-amino-3-chloropyridin-4-yl)thio)pyrazin-2-yl)-3-methyl-8-azaspiro[4.5]decan-1-amine; or m) the ALK inhibitor is 5-chloro-N2-[2-isopropoxy-5-methyl-4-(4-piperidinyl)phenyl]-N4-[2-(isopropylsulfonyl)phenyl]-2,4-pyrimidinediamine (ceritinib) and the SHP2 inhibitor is (2S,4R)-4-amino-8-(6-amino-5-((2,3-dichloropyridin-4-yl)thio)pyrazin-2-yl)-8-azaspiro[4.5]decan-2-ol; or n) the ALK inhibitor is 5-chloro-N2-[2-isopropoxy-5-methyl-4-(4-piperidinyl)phenyl]-N4-[2-(isopropylsulfonyl)phenyl]-2,4-pyrimidinediamine (ceritinib) and the SHP2 inhibitor is (2R,4R)-4-amino-8-(6-amino-5-((2,3-dichloropyridin-4-yl)thio)pyrazin-2-yl)-8-azaspiro[4.5]decan-2-ol; or o) the ALK inhibitor is 5-chloro-N2-[2-isopropoxy-5-methyl-4-(4-piperidinyl)phenyl]-N4-[2-(isopropylsulfonyl)phenyl]-2,4-pyrimidinediamine (ceritinib) and the SHP2 inhibitor is (1R)-8-(6-amino-5-((2-amino-3-chloropyridin-4-yl)thio)pyrazin-2-yl)-2-methyl-8-azaspiro[4.5]decan-1-amine; or p) the ALK inhibitor is 5-chloro-N2-[2-isopropoxy-5-methyl-4-(4-piperidinyl)phenyl]-N4-[2-(isopropylsulfonyl)phenyl]-2,4-pyrimidinediamine (ceritinib) and the SHP2 inhibitor is (3S,4S)-8-(6-amino-5-((2-amino-3-chloropyridin-4-yl)thio)pyrazin-2-yl)-3-methyl-2-oxa-8-azaspiro[4.5]decan-4-amine; or q) the ALK inhibitor is 5-chloro-N2-[2-isopropoxy-5-methyl-4-(4-piperidinyl)phenyl]-N4-[2-(isopropylsulfonyl)phenyl]-2,4-pyrimidinediamine (ceritinib) and the SHP2 inhibitor is (3S,4S)-8-(6-amino-5-((2-amino-3-chloropyridin-4-yl)thio)pyrazin-2-yl)-3-ethyl-2-oxa-8-azaspiro[4.5]decan-4-amine; or r) the ALK inhibitor is 5-chloro-N2-[2-isopropoxy-5-methyl-4-(4-piperidinyl)phenyl]-N4-[2-(isopropylsulfonyl)phenyl]-2,4-pyrimidinediamine (ceritinib) and the SHP2 inhibitor is (2R,4R)-4-amino-8-(5-((2-amino-3-chloropyridin-4-yl)thio)pyrazin-2-yl)-8-azaspiro[4.5]decan-2-ol; or s) the ALK inhibitor is 5-chloro-N2-[2-isopropoxy-5-methyl-4-(4-piperidinyl)phenyl]-N4-[2-(isopropylsulfonyl)phenyl]-2,4-pyrimidinediamine (ceritinib) and the SHP2 inhibitor is (1R,3R)-8-(5-((2-amino-3-chloropyridin-4-yl)thio)pyrazin-2-yl)-3-methyl-8-azaspiro[4.5]decan-1-amine; or t) the ALK inhibitor is 5-chloro-N2-[2-isopropoxy-5-methyl-4-(4-piperidinyl)phenyl]-N4-[2-(isopropylsulfonyl)phenyl]-2,4-pyrimidinediamine (ceritinib) and the SHP2 inhibitor is (1R)-8-(5-((2-amino-3-chloropyridin-4-yl)thio)pyrazin-2-yl)-2-methyl-8-azaspiro[4.5]decan-1-amine; or u) the ALK inhibitor is 5-chloro-N2-[2-isopropoxy-5-methyl-4-(4-piperidinyl)phenyl]-N4-[2-(isopropylsulfonyl)phenyl]-2,4-pyrimidinediamine (ceritinib) and the SHP2 inhibitor is (3S,4S)-8-(5-((6-amino-2,3-dichloropyridin-4-yl)thio)pyrazin-2-yl)-3-methyl-2-oxa-8-azaspiro[4.5]decan-4-amine; or v) the ALK inhibitor is 5-chloro-N2-[2-isopropoxy-5-methyl-4-(4-piperidinyl)phenyl]-N4-[2-(isopropylsulfonyl)phenyl]-2,4-pyrimidinediamine (ceritinib) and the SHP2 inhibitor is (3S,4S)-8-(5-((2-amino-3-chloropyridin-4-yl)thio)pyrazin-2-yl)-3-methyl-2-oxa-8-azaspiro[4.5]decan-4-amine; or w) the ALK inhibitor is 5-chloro-N2-[2-isopropoxy-5-methyl-4-(4-piperidinyl)phenyl]-N4-[2-(isopropylsulfonyl)phenyl]-2,4-pyrimidinediamine (ceritinib) and the SHP2 inhibitor is (R)-8-(5-((2-amino-3-chloropyridin-4-yl)thio)pyrazin-2-yl)-8-azaspiro[4.5]decan-1-amine; or x) the ALK inhibitor is 5-chloro-N2-[2-isopropoxy-5-methyl-4-(4-piperidinyl)phenyl]-N4-[2-(isopropylsulfonyl)phenyl]-2,4-pyrimidinediamine (ceritinib) and the SHP2 inhibitor is (S)-8-(5-((2-amino-3-chloropyridin-4-yl)thio)pyrazin-2-yl)-2-oxa-8-azaspiro[4.5]decan-4-amine; or y) the ALK inhibitor is 5-chloro-N2-[2-isopropoxy-5-methyl-4-(4-piperidinyl)phenyl]-N4-[2-(isopropylsulfonyl)phenyl]-2,4-pyrimidinediamine (ceritinib) and the SHP2 inhibitor is 6-amino-2-((3S,4S)-4-amino-3-methyl-2-oxa-8-azaspiro[4.5]decan-8-yl)-3-methyl-5-((2-(trifluoromethyl)pyridin-3-yl)thio)pyrimidin-4(3H)-one; or z) the ALK inhibitor is 5-chloro-N2-[2-isopropoxy-5-methyl-4-(4-piperidinyl)phenyl]-N4-[2-(isopropylsulfonyl)phenyl]-2,4-pyrimidinediamine (ceritinib) and the SHP2 inhibitor is 6-amino-2-((3S,4S)-4-amino-3-methyl-2-oxa-8-azaspiro[4.5]decan-8-yl)-5-((3-chloro-2-methylpyridin-4-yl)thio)-3-methylpyrimidin-4(3H)-one; or aa) the ALK inhibitor is 5-chloro-N2-[2-isopropoxy-5-methyl-4-(4-piperidinyl)phenyl]-N4-[2-(isopropylsulfonyl)phenyl]-2,4-pyrimidinediamine (ceritinib) and the SHP2 inhibitor is 6-amino-2-((3S,4S)-4-amino-3-methyl-2-oxa-8-azaspiro[4.5]decan-8-yl)-5-((2,3-dichlorophenyl)thio)-3-methylpyrimidin-4(3H)-one; or bb) the ALK inhibitor is 5-chloro-N2-[2-isopropoxy-5-methyl-4-(4-piperidinyl)phenyl]-N4-[2-(isopropylsulfonyl)phenyl]-2,4-pyrimidinediamine (ceritinib) and the SHP2 inhibitor is 6-amino-2-((1R,3R)-1- amino-3-methyl-8-azaspiro[4.5]decan-8-yl)-3-methyl-5-((3-(trifluoromethyl)pyridin-4-yl)thio)pyrimidin-4(3H)-one; or cc) the ALK inhibitor is 5-chloro-N2-[2-isopropoxy-5-methyl-4-(4-piperidinyl)phenyl]-N4-[2-(isopropylsulfonyl)phenyl]-2,4-pyrimidinediamine (ceritinib) and the SHP2 inhibitor is 6-amino-2-((1R,3R)-1-amino-3-methyl-8-azaspiro[4.5]decan-8-yl)-5-(2,3-dichlorophenyl)-3-methylpyrimidin-4(3H)-one; or dd) the ALK inhibitor is 5-chloro-N2-[2-isopropoxy-5-methyl-4-(4-piperidinyl)phenyl]-N4-[2-(isopropylsulfonyl)phenyl]-2,4-pyrimidinediamine (ceritinib) and the SHP2 inhibitor is 6-amino-2-((3S,4S)-4-amino-3-methyl-2-oxa-8-azaspiro[4.5]decan-8-yl)-5-((2-chloro-3-methoxyphenyl)thio)-3-methylpyrimidin-4(3H)-one; or ee) the ALK inhibitor is 5-chloro-N2-[2-isopropoxy-5-methyl-4-(4-piperidinyl)phenyl]-N4-[2-(isopropylsulfonyl)phenyl]-2,4-pyrimidinediamine (ceritinib) and the SHP2 inhibitor is 6-amino-2-((3S,4S)-4-amino-3-ethyl-2-oxa-8-azaspiro[4.5]decan-8-yl)-3-methyl-5-((2-(trifluoromethyl)pyridin-3-yl)thio)pyrimidin-4(3H)-one; or ff) the ALK inhibitor is 5-chloro-N2-[2-isopropoxy-5-methyl-4-(4-piperidinyl)phenyl]-N4-[2-(isopropylsulfonyl)phenyl]-2,4-pyrimidinediamine (ceritinib) and the SHP2 inhibitor is 6-amino-5-((3-amino-2-(trifluoromethyl)phenyl)thio)-2-((3S,4S)-4-amino-3-methyl-2-oxa-8-azaspiro[4.5]decan-8-yl)-3-methylpyrimidin-4(3H)-one; or gg) the ALK inhibitor is 5-chloro-N2-[2-isopropoxy-5-methyl-4-(4-piperidinyl)phenyl]-N4-[2-(isopropylsulfonyl)phenyl]-2,4-pyrimidinediamine (ceritinib) and the SHP2 inhibitor is (R)-6-amino-2-(1-amino-3,3-difluoro-8-azaspiro[4.5]decan-8-yl)-5-((2-amino-3-chloropyridin-4-yl)thio)-3-methylpyrimidin-4(3H)-one; or hh) the ALK inhibitor is 5-chloro-N2-[2-isopropoxy-5-methyl-4-(4-piperidinyl)phenyl]-N4-[2-(isopropylsulfonyl)phenyl]-2,4-pyrimidinediamine (ceritinib) and the SHP2 inhibitor is 6-amino-2-((3S,4S)-4-amino-3-methyl-2-oxa-8-azaspiro[4.5]decan-8-yl)-3-methyl-5-((3-(trifluoromethyl)pyridin-4-yl)thio)pyrimidin-4(3H)-one; or ii) the ALK inhibitor is 5-chloro-N2-[2-isopropoxy-5-methyl-4-(4-piperidinyl)phenyl]-N4-[2-(isopropylsulfonyl)phenyl]-2,4-pyrimidinediamine (ceritinib) and the SHP2 inhibitor is 6-amino-2-((1R,3R)-1-amino-3-methyl-8-azaspiro[4.5]decan-8-yl)-5-(4-chlorophenyl)-3-methylpyrimidin-4(3H)-one; or jj) the ALK inhibitor is 5-chloro-N2-[2-isopropoxy-5-methyl-4-(4-piperidinyl)phenyl]-N4-[2-(isopropylsulfonyl)phenyl]-2,4-pyrimidinediamine (ceritinib) and the SHP2 inhibitor is 6-amino-2-((1R,3R)-1-amino-3-methyl-8-azaspiro[4.5]decan-8-yl)-3-methyl-5-phenylpyrimidin-4(3H)-one; or kk) the ALK inhibitor is 5-chloro-N2-[2-isopropoxy-5-methyl-4-(4-piperidinyl)phenyl]-N4-[2-(isopropylsulfonyl)phenyl]-2,4-pyrimidinediamine (ceritinib) and the SHP2 inhibitor is (R)-6-(1-amino-8-azaspiro[4.5]decan-8-yl)-3-(2,3-dichlorophenyl)-5-methyl-2,5-dihydro-4H-pyrazolo[3,4-d]pyrimidin-4-one; or ll) the ALK inhibitor is 5-chloro-N2-[2-isopropoxy-5-methyl-4-(4-piperidinyl)phenyl]-N4-[2-(isopropylsulfonyl)phenyl]-2,4-pyrimidinediamine (ceritinib) and the SHP2 inhibitor is 2-(4-(aminomethyl)-4-methylpiperidin-1-yl)-5-(2,3-dichlorophenyl)-3,7-dihydro-4H-pyrrolo[2,3-d]pyrimidin-4-one; or mm) the ALK inhibitor is 5-chloro-N2-[2-isopropoxy-5-methyl-4-(4-piperidinyl)phenyl]-N4-[2-(isopropylsulfonyl)phenyl]-2,4-pyrimidinediamine (ceritinib) and the SHP2 inhibitor is (3S,4S)-8-(3-(2,3-dichloropyridin-4-yl)-1H-pyrazolo[3,4-b]pyrazin-6-yl)-3-methyl-2-oxa-8-azaspiro[4.5]decan-4-amine; or nn) the ALK inhibitor is 5-chloro-N2-[2-isopropoxy-5-methyl-4-(4-piperidinyl)phenyl]-N4-[2-(isopropylsulfonyl)phenyl]-2,4-pyrimidinediamine (ceritinib) and the SHP2 inhibitor is 3-(6-amino-2-methylpyridin-3-yl)-6-((1R,3R)-1-amino-3-methyl-8-azaspiro[4.5]decan-8-yl)-5-methyl-2,5-dihydro-4H-pyrazolo[3,4-d]pyrimidin-4-one; or oo) the ALK inhibitor is 5-chloro-N2-[2-isopropoxy-5-methyl-4-(4-piperidinyl)phenyl]-N4-[2-(isopropylsulfonyl)phenyl]-2,4-pyrimidinediamine (ceritinib) and the SHP2 inhibitor is (R)-3-(6-amino-2-methylpyridin-3-yl)-6-(1-amino-3,3-difluoro-8-azaspiro[4.5]decan-8-yl)-5-methyl-2,5-dihydro-4H-pyrazolo[3,4-d]pyrimidin-4-one; or pp) the ALK inhibitor is 5-chloro-N2-[2-isopropoxy-5-methyl-4-(4-piperidinyl)phenyl]-N4-[2-(isopropylsulfonyl)phenyl]-2,4-pyrimidinediamine (ceritinib) and the SHP2 inhibitor is 6-((3S,4S)-4-amino-3-methyl-2-oxa-8-azaspiro[4.5]decan-8-yl)-3-(3-chloro-2-(cyclopropylamino)pyridin-4-yl)-5-methyl-2,5-dihydro-4H-pyrazolo[3,4-d]pyrimidin-4-one; or qq) the ALK inhibitor is 5-chloro-N2-[2-isopropoxy-5-methyl-4-(4-piperidinyl)phenyl]-N4-[2-(isopropylsulfonyl)phenyl]-2,4-pyrimidinediamine (ceritinib) and the SHP2 inhibitor is 2-((3S,4S)-4-amino-3-methyl-2-oxa-8-azaspiro[4.5]decan-8-yl)-5-(3-chloro-2-methoxypyridin-4-yl)-3-methyl-3,7-dihydro-4H-pyrrolo[2,3-d]pyrimidin-4-one; or rr) the ALK inhibitor is 5-chloro-N2-[2-isopropoxy-5-methyl-4-(4-piperidinyl)phenyl]-N4-[2-(isopropylsulfonyl)phenyl]-2,4-pyrimidinediamine (ceritinib) and the SHP2 inhibitor is N-(3-((3-amino-5-(4-amino-4-methylpiperidin-1-yl)pyrazin-2-yl)thio)-2-chlorophenyl)-2-hydroxy-4-oxo-4H-pyrido[1,2-a]pyrimidine-3-carboxamide; or ss) the ALK inhibitor is 5-chloro-N2-[2-isopropoxy-5-methyl-4-(4-piperidinyl)phenyl]-N4-[2-(isopropylsulfonyl)phenyl]-2,4-pyrimidinediamine (ceritinib) and the SHP2 inhibitor is N-(3-((3-amino-5-((3S,4S)-4-amino-3-methyl-2-oxa-8-azaspiro[4.5]decan-8-yl)pyrazin-2-yl)thio)-2-chlorophenyl)-2-hydroxy-4-oxo-6,7,8,9-tetrahydro-4H-pyrido[1,2-a]pyrimidine-3-carboxamide; or tt) the ALK inhibitor is 5-chloro-N2-[2-isopropoxy-5-methyl-4-(4-piperidinyl)phenyl]-N4-[2-(isopropylsulfonyl)phenyl]-2,4-pyrimidinediamine (ceritinib) and the SHP2 inhibitor is N-(3-((3-amino-5-(4-amino-4-methylpiperidin-1-yl)pyrazin-2-yl)thio)-2-chlorophenyl)-4-hydroxy-2-oxo-1-phenyl-2,5-dihydro-1H-pyrrole-3-carboxamide; or uu) the ALK inhibitor is 5-chloro-N2-[2-isopropoxy-5-methyl-4-(4-piperidinyl)phenyl]-N4-[2-(isopropylsulfonyl)phenyl]-2,4-pyrimidinediamine (ceritinib) and the SHP2 inhibitor is (R)—N-(3-((3-amino-5-(1-amino-8-azaspiro[4.5]decan-8-yl)pyrazin-2-yl)thio)-2-chlorophenyl)-2-hydroxy-4-oxo-6,7,8,9-tetrahydro-4H-pyrido[1,2-a]pyrimidine-3-carboxamide; or vv) the ALK inhibitor is 5-chloro-N2-[2-isopropoxy-5-methyl-4-(4-piperidinyl)phenyl]-N4-[2-(isopropylsulfonyl)phenyl]-2,4-pyrimidinediamine (ceritinib) and the SHP2 inhibitor is N-(3-((3-amino-5-(4-(aminomethyl)-4-methylpiperidin-1-yl)pyrazin-2-yl)thio)-2-chlorophenyl)-2-hydroxy-4-oxo-6,7,8,9-tetrahydro-4H-pyrido[1,2-a]pyrimidine-3-carboxamide; or ww) the ALK inhibitor is 5-chloro-N2-[2-isopropoxy-5-methyl-4-(4-piperidinyl)phenyl]-N4-[2-(isopropylsulfonyl)phenyl]-2,4-pyrimidinediamine (ceritinib) and the SHP2 inhibitor is (R)—N-(3-((3-amino-5-(1-amino-3,3-difluoro-8-azaspiro[4.5]decan-8-yl)pyrazin-2-yl)thio)-2-chlorophenyl)-2-hydroxy-4-oxo-6,7,8,9-tetrahydro-4H-pyrido[1,2-a]pyrimidine-3-carboxamide; or xx) the ALK inhibitor is 5-chloro-N2-[2-isopropoxy-5-methyl-4-(4-piperidinyl)phenyl]-N4-[2-(isopropylsulfonyl)phenyl]-2,4-pyrimidinediamine (ceritinib) and the SHP2 inhibitor is N-(3-((3-amino-5-(4-(aminomethyl)-4-methylpiperidin-1-yl)pyrazin-2-yl)thio)-2-chlorophenyl)-2-hydroxy-4-oxo-4H-pyrido[1,2-a]pyrimidine-3-carboxamide; or yy) the ALK inhibitor is 5-chloro-N2-[2-isopropoxy-5-methyl-4-(4-piperidinyl)phenyl]-N4-[2-(isopropylsulfonyl)phenyl]-2,4-pyrimidinediamine (ceritinib) and the SHP2 inhibitor is N-(3-((3-amino-5-(4-amino-4-(fluoromethyl)piperidin-1-yl)pyrazin-2-yl)thio)-2-chlorophenyl)-2-hydroxy-4-oxo-6,7,8,9-tetrahydro-4H-pyrido[1,2-a]pyrimidine-3-carboxamide; or zz) the ALK inhibitor is 5-chloro-N2-[2-isopropoxy-5-methyl-4-(4-piperidinyl)phenyl]-N4-[2-(isopropylsulfonyl)phenyl]-2,4-pyrimidinediamine (ceritinib) and the SHP2 inhibitor is N-(3-((3-amino-5-(4-amino-4-(fluoromethyl)piperidin-1-yl)pyrazin-2-yl)thio)-2-chlorophenyl)-2-hydroxy-4-oxo-4H-pyrido[1,2-a]pyrimidine-3-carboxamide; or aaa) the ALK inhibitor is 5-chloro-N2-[2-isopropoxy-5-methyl-4-(4-piperidinyl)phenyl]-N4-[2-(isopropylsulfonyl)phenyl]-2,4-pyrimidinediamine (ceritinib) and the SHP2 inhibitor is (S)—N-(3-((3-amino-5-(4-amino-2-oxa-8-azaspiro[4.5]decan-8-yl)pyrazin-2-yl)thio)-2-chlorophenyl)-2-hydroxy-4-oxo-6,7,8,9-tetrahydro-4H-pyrido[1,2-a]pyrimidine-3-carboxamide; or bbb) the ALK inhibitor is 5-chloro-N2-[2-isopropoxy-5-methyl-4-(4-piperidinyl)phenyl]-N4-[2-(isopropylsulfonyl)phenyl]-2,4-pyrimidinediamine (ceritinib) and the SHP2 inhibitor is N-(3-((3-amino-5-(4-amino-4-methylpiperidin-1-yl)pyrazin-2-yl)thio)-2-chlorophenyl)-5-benzyl-4-hydroxy-1-methyl-2-oxo-2,5-dihydro-1H-pyrrole-3-carboxamide.

Item 29: The pharmaceutical combination, the pharmaceutical composition, the commercial package, the pharmaceutical combination for use, the pharmaceutical composition for use, the commercial package for use, use of the pharmaceutical combination, use of the pharmaceutical composition, use of the commercial package, or the method of treating a cancer according item 28, wherein the ALK inhibitor is 5-chloro-N2-[2-isopropoxy-5-methyl-4-(4-piperidinyl)phenyl]-N4-[2-(isopropylsulfonyl)phenyl]-2,4-pyrimidinediamine (ceritinib) and the SHP2 inhibitor is 6-(4-amino-4-methylpiperidin-1-yl)-3-(2,3-dichlorophenyl)pyrazin-2-amine.

Item 30: The pharmaceutical combination, the pharmaceutical composition, the commercial package, the pharmaceutical combination for use, the pharmaceutical composition for use, the commercial package for use, use of the pharmaceutical combination, use of the pharmaceutical composition, use of the commercial package, or the method of treating a cancer according item 28, wherein the ALK inhibitor is 5-chloro-N2-[2-isopropoxy-5-methyl-4-(4-piperidinyl)phenyl]-N4-[2-(isopropylsulfonyl)phenyl]-2,4-pyrimidinediamine (ceritinib) and the SHP2 inhibitor is 6-(4-(aminomethyl)-4-phenylpiperidin-1-yl)-3-(2,3-dichlorophenyl)pyrazin-2-amine.

Item 31: The pharmaceutical combination, the pharmaceutical composition, the commercial package, the pharmaceutical combination for use, the pharmaceutical composition for use, the commercial package for use, use of the pharmaceutical combination, use of the pharmaceutical composition, use of the commercial package, or the method of treating a cancer according item 28, wherein the ALK inhibitor is 5-chloro-N2-[2-isopropoxy-5-methyl-4-(4-piperidinyl)phenyl]-N4-[2-(isopropylsulfonyl)phenyl]-2,4-pyrimidinediamine (ceritinib) and the SHP2 inhibitor is 6-(4-(aminomethyl)-4-methylpiperidin-1-yl)-3-(2,3-dichlorophenyl)pyrazin-2-amine.

Item 32: The pharmaceutical combination, the pharmaceutical composition, the commercial package, the pharmaceutical combination for use, the pharmaceutical composition for use, the commercial package for use, use of the pharmaceutical combination, use of the pharmaceutical composition, use of the commercial package, or the method of treating a cancer according item 28, wherein the ALK inhibitor is 5-chloro-N2-[2-isopropoxy-5-methyl-4-(4-piperidinyl)phenyl]-N4-[2-(isopropylsulfonyl)phenyl]-2,4-pyrimidinediamine (ceritinib) and the SHP2 inhibitor is 6-(4-(aminomethyl)-4-methylpiperidin-1-yl)-3-((2-(trifluoromethyl)pyridin-3-yl)thio)pyrazin-2-amine.

Item 33: The pharmaceutical combination, the pharmaceutical composition, the commercial package, the pharmaceutical combination for use, the pharmaceutical composition for use, the commercial package for use, use of the pharmaceutical combination, use of the pharmaceutical composition, use of the commercial package, or the method of treating a cancer according item 28, wherein the ALK inhibitor is 5-chloro-N2-[2-isopropoxy-5-methyl-4-(4-piperidinyl)phenyl]-N4-[2-(isopropylsulfonyl)phenyl]-2,4-pyrimidinediamine (ceritinib) and the SHP2 inhibitor is (R)-8-(6-amino-5-((2-(trifluoromethyl)pyridin-3-yl)thio)pyrazin-2-yl)-8-azaspiro[4.5]decan-1-amine.

Item 34: The pharmaceutical combination, the pharmaceutical composition, the commercial package, the pharmaceutical combination for use, the pharmaceutical composition for use, the commercial package for use, use of the pharmaceutical combination, use of the pharmaceutical composition, use of the commercial package, or the method of treating a cancer according item 28, wherein the ALK inhibitor is 5-chloro-N2-[2-isopropoxy-5-methyl-4-(4-piperidinyl)phenyl]-N4-[2-(isopropylsulfonyl)phenyl]-2,4-pyrimidinediamine (ceritinib) and the SHP2 inhibitor is (R)-8-(6-amino-5-((2-amino-3-chloropyridin-4-yl)thio)pyrazin-2-yl)-8-azaspiro[4.5]decan-1-amine.

Item 35: The pharmaceutical combination, the pharmaceutical composition, the commercial package, the pharmaceutical combination for use, the pharmaceutical composition for use, the commercial package for use, use of the pharmaceutical combination, use of the pharmaceutical composition, use of the commercial package, or the method of treating a cancer according item 28, wherein the ALK inhibitor is 5-chloro-N2-[2-isopropoxy-5-methyl-4-(4-piperidinyl)phenyl]-N4-[2-(isopropylsulfonyl)phenyl]-2,4-pyrimidinediamine (ceritinib) and the SHP2 inhibitor is (3S,4S)-8-(6-amino-5-(2,3-dichlorophenyl)pyrazin-2-yl)-3-methyl-2-oxa-8-azaspiro[4.5]decan-4-amine.

Item 36: The pharmaceutical combination, the pharmaceutical composition, the commercial package, the pharmaceutical combination for use, the pharmaceutical composition for use, the commercial package for use, use of the pharmaceutical combination, use of the pharmaceutical composition, use of the commercial package, or the method of treating a cancer according item 28, wherein the ALK inhibitor is 5-chloro-N2-[2-isopropoxy-5-methyl-4-(4-piperidinyl)phenyl]-N4-[2-(isopropylsulfonyl)phenyl]-2,4-pyrimidinediamine (ceritinib) and the SHP2 3-(2,3-dichlorophenyl)-6-(1,8-diazaspiro[4.5]decan-8-yl)pyrazin-2-amine.

Item 37: The pharmaceutical combination, the pharmaceutical composition, the commercial package, the pharmaceutical combination for use, the pharmaceutical composition for use, the commercial package for use, use of the pharmaceutical combination, use of the pharmaceutical composition, use of the commercial package, or the method of treating a cancer according item 28, wherein the ALK inhibitor is 5-chloro-N2-[2-isopropoxy-5-methyl-4-(4-piperidinyl)phenyl]-N4-[2-(isopropylsulfonyl)phenyl]-2,4-pyrimidinediamine (ceritinib) and the SHP2 inhibitor is (R)-8-(6-amino-5-(2,3-dichlorophenyl)pyrazin-2-yl)-8-azaspiro[4.5]decan-1-amine.

Item 38: The pharmaceutical combination, the pharmaceutical composition, the commercial package, the pharmaceutical combination for use, the pharmaceutical composition for use, the commercial package for use, use of the pharmaceutical combination, use of the pharmaceutical composition, use of the commercial package, or the method of treating a cancer according item 28, wherein the ALK inhibitor is 5-chloro-N2-[2-isopropoxy-5-methyl-4-(4-piperidinyl)phenyl]-N4-[2-(isopropylsulfonyl)phenyl]-2,4-pyrimidinediamine (ceritinib) and the SHP2 inhibitor is (S)-8-(6-amino-5-((2-(trifluoromethyl)pyridin-3-yl)thio)pyrazin-2-yl)-2-oxa-8-azaspiro[4.5]decan-4-amine.

Item 39: The pharmaceutical combination, the pharmaceutical composition, the commercial package, the pharmaceutical combination for use, the pharmaceutical composition for use, the commercial package for use, use of the pharmaceutical combination, use of the pharmaceutical composition, use of the commercial package, or the method of treating a cancer according item 28, wherein the ALK inhibitor is 5-chloro-N2-[2-isopropoxy-5-methyl-4-(4-piperidinyl)phenyl]-N4-[2-(isopropylsulfonyl)phenyl]-2,4-pyrimidinediamine (ceritinib) and the SHP2 inhibitor is (S)-8-(6-amino-5-((2-amino-3-chloropyridin-4-yl)thio)pyrazin-2-yl)-2-oxa-8-azaspiro[4.5]decan-4-amine.

Item 40: The pharmaceutical combination, the pharmaceutical composition, the commercial package, the pharmaceutical combination for use, the pharmaceutical composition for use, the commercial package for use, use of the pharmaceutical combination, use of the pharmaceutical composition, use of the commercial package, or the method of treating a cancer according item 28, wherein the ALK inhibitor is 5-chloro-N2-[2-isopropoxy-5-methyl-4-(4-piperidinyl)phenyl]-N4-[2-(isopropylsulfonyl)phenyl]-2,4-pyrimidinediamine (ceritinib) and the SHP2 inhibitor is (1R,3R)-8-(6-amino-5-((2-amino-3-chloropyridin-4-yl)thio)pyrazin-2-yl)-3-methyl-8-azaspiro[4.5]decan-1-amine.

Item 41: The pharmaceutical combination, the pharmaceutical composition, the commercial package, the pharmaceutical combination for use, the pharmaceutical composition for use, the commercial package for use, use of the pharmaceutical combination, use of the pharmaceutical composition, use of the commercial package, or the method of treating a cancer according item 28, wherein the ALK inhibitor is 5-chloro-N2-[2-isopropoxy-5-methyl-4-(4-piperidinyl)phenyl]-N4-[2-(isopropylsulfonyl)phenyl]-2,4-pyrimidinediamine (ceritinib) and the SHP2 inhibitor is (2S,4R)-4-amino-8-(6-amino-5-((2,3-dichloropyridin-4-yl)thio)pyrazin-2-yl)-8-azaspiro[4.5]decan-2-ol.

Item 42: The pharmaceutical combination, the pharmaceutical composition, the commercial package, the pharmaceutical combination for use, the pharmaceutical composition for use, the commercial package for use, use of the pharmaceutical combination, use of the pharmaceutical composition, use of the commercial package, or the method of treating a cancer according item 28, wherein the ALK inhibitor is 5-chloro-N2-[2-isopropoxy-5-methyl-4-(4-piperidinyl)phenyl]-N4-[2-(isopropylsulfonyl)phenyl]-2,4-pyrimidinediamine (ceritinib) and the SHP2 inhibitor is (2R,4R)-4-amino-8-(6-amino-5-((2,3-dichloropyridin-4-yl)thio)pyrazin-2-yl)-8-azaspiro[4.5]decan-2-ol.

Item 43: The pharmaceutical combination, the pharmaceutical composition, the commercial package, the pharmaceutical combination for use, the pharmaceutical composition for use, the commercial package for use, use of the pharmaceutical combination, use of the pharmaceutical composition, use of the commercial package, or the method of treating a cancer according item 28, wherein the ALK inhibitor is 5-chloro-N2-[2-isopropoxy-5-methyl-4-(4-piperidinyl)phenyl]-N4-[2-(isopropylsulfonyl)phenyl]-2,4-pyrimidinediamine (ceritinib) and the SHP2 inhibitor is (1R)-8-(6-amino-5-((2-amino-3-chloropyridin-4-yl)thio)pyrazin-2-yl)-2-methyl-8-azaspiro[4.5]decan-1-amine.

Item 44: The pharmaceutical combination, the pharmaceutical composition, the commercial package, the pharmaceutical combination for use, the pharmaceutical composition for use, the commercial package for use, use of the pharmaceutical combination, use of the pharmaceutical composition, use of the commercial package, or the method of treating a cancer according item 28, wherein the ALK inhibitor is 5-chloro-N2-[2-isopropoxy-5-methyl-4-(4-piperidinyl)phenyl]-N4-[2-(isopropylsulfonyl)phenyl]-2,4-pyrimidinediamine (ceritinib) and the SHP2 inhibitor is (3S,4S)-8-(6-amino-5-((2-amino-3-chloropyridin-4-yl)thio)pyrazin-2-yl)-3-methyl-2-oxa-8-azaspiro[4.5]decan-4-amine.

Item 45: The pharmaceutical combination, the pharmaceutical composition, the commercial package, the pharmaceutical combination for use, the pharmaceutical composition for use, the commercial package for use, use of the pharmaceutical combination, use of the pharmaceutical composition, use of the commercial package, or the method of treating a cancer according item 28, wherein the ALK inhibitor is 5-chloro-N2-[2-isopropoxy-5-methyl-4-(4-piperidinyl)phenyl]-N4-[2-(isopropylsulfonyl)phenyl]-2,4-pyrimidinediamine (ceritinib) and the SHP2 inhibitor is (3S,4S)-8-(6-amino-5-((2-amino-3-chloropyridin-4-yl)thio)pyrazin-2-yl)-3-ethyl-2-oxa-8-azaspiro[4.5]decan-4-amine.

Item 46: The pharmaceutical combination, the pharmaceutical composition, the commercial package, the pharmaceutical combination for use, the pharmaceutical composition for use, the commercial package for use, use of the pharmaceutical combination, use of the pharmaceutical composition, use of the commercial package, or the method of treating a cancer according item 28, wherein the ALK inhibitor is 5-chloro-N2-[2-isopropoxy-5-methyl-4-(4-piperidinyl)phenyl]-N4-[2-(isopropylsulfonyl)phenyl]-2,4-pyrimidinediamine (ceritinib) and the SHP2 inhibitor is (2R,4R)-4-amino-8-(5-((2-amino-3-chloropyridin-4-yl)thio)pyrazin-2-yl)-8-azaspiro[4.5]decan-2-ol.

Item 47: The pharmaceutical combination, the pharmaceutical composition, the commercial package, the pharmaceutical combination for use, the pharmaceutical composition for use, the commercial package for use, use of the pharmaceutical combination, use of the pharmaceutical composition, use of the commercial package, or the method of treating a cancer according item 28, wherein the ALK inhibitor is 5-chloro-N2-[2-isopropoxy-5-methyl-4-(4-piperidinyl)phenyl]-N4-[2-(isopropylsulfonyl)phenyl]-2,4-pyrimidinediamine (ceritinib) and the SHP2 inhibitor is (1R,3R)-8-(5-((2-amino-3-chloropyridin-4-yl)thio)pyrazin-2-yl)-3-methyl-8-azaspiro[4.5]decan-1-amine.

Item 48: The pharmaceutical combination, the pharmaceutical composition, the commercial package, the pharmaceutical combination for use, the pharmaceutical composition for use, the commercial package for use, use of the pharmaceutical combination, use of the pharmaceutical composition, use of the commercial package, or the method of treating a cancer according item 28, wherein the ALK inhibitor is 5-chloro-N2-[2-isopropoxy-5-methyl-4-(4-piperidinyl)phenyl]-N4-[2-(isopropylsulfonyl)phenyl]-2,4-pyrimidinediamine (ceritinib) and the SHP2 inhibitor is (1R)-8-(5-((2-amino-3-chloropyridin-4-yl)thio)pyrazin-2-yl)-2-methyl-8-azaspiro[4.5]decan-1-amine.

Item 49: The pharmaceutical combination, the pharmaceutical composition, the commercial package, the pharmaceutical combination for use, the pharmaceutical composition for use, the commercial package for use, use of the pharmaceutical combination, use of the pharmaceutical composition, use of the commercial package, or the method of treating a cancer according item 28, wherein the ALK inhibitor is 5-chloro-N2-[2-isopropoxy-5-methyl-4-(4-piperidinyl)phenyl]-N4-[2-(isopropylsulfonyl)phenyl]-2,4-pyrimidinediamine (ceritinib) and the SHP2 inhibitor is (3S,4S)-8-(5-((6-amino-2,3-dichloropyridin-4-yl)thio)pyrazin-2-yl)-3-methyl-2-oxa-8-azaspiro[4.5]decan-4-amine.

Item 50: The pharmaceutical combination, the pharmaceutical composition, the commercial package, the pharmaceutical combination for use, the pharmaceutical composition for use, the commercial package for use, use of the pharmaceutical combination, use of the pharmaceutical composition, use of the commercial package, or the method of treating a cancer according item 28, wherein the ALK inhibitor is 5-chloro-N2-[2-isopropoxy-5-methyl-4-(4-piperidinyl)phenyl]-N4-[2-(isopropylsulfonyl)phenyl]-2,4-pyrimidinediamine (ceritinib) and the SHP2 inhibitor is (3S,4S)-8-(5-((2-amino-3-chloropyridin-4-yl)thio)pyrazin-2-yl)-3-methyl-2-oxa-8-azaspiro[4.5]decan-4-amine.

Item 51: The pharmaceutical combination, the pharmaceutical composition, the commercial package, the pharmaceutical combination for use, the pharmaceutical composition for use, the commercial package for use, use of the pharmaceutical combination, use of the pharmaceutical composition, use of the commercial package, or the method of treating a cancer according item 28, wherein the ALK inhibitor is 5-chloro-N2-[2-isopropoxy-5-methyl-4-(4-piperidinyl)phenyl]-N4-[2-(isopropylsulfonyl)phenyl]-2,4-pyrimidinediamine (ceritinib) and the SHP2 inhibitor is (R)-8-(5-((2-amino-3-chloropyridin-4-yl)thio)pyrazin-2-yl)-8-azaspiro[4.5]decan-1-amine.

Item 52: The pharmaceutical combination, the pharmaceutical composition, the commercial package, the pharmaceutical combination for use, the pharmaceutical composition for use, the commercial package for use, use of the pharmaceutical combination, use of the pharmaceutical composition, use of the commercial package, or the method of treating a cancer according item 28, wherein the ALK inhibitor is 5-chloro-N2-[2-isopropoxy-5-methyl-4-(4-piperidinyl)phenyl]-N4-[2-(isopropylsulfonyl)phenyl]-2,4-pyrimidinediamine (ceritinib) and the SHP2 inhibitor is (S)-8-(5-((2-amino-3-chloropyridin-4-yl)thio)pyrazin-2-yl)-2-oxa-8-azaspiro[4.5]decan-4-amine.

Item 53: The pharmaceutical combination, the pharmaceutical composition, the commercial package, the pharmaceutical combination for use, the pharmaceutical composition for use, the commercial package for use, use of the pharmaceutical combination, use of the pharmaceutical composition, use of the commercial package, or the method of treating a cancer according item 28, wherein the ALK inhibitor is 5-chloro-N2-[2-isopropoxy-5-methyl-4-(4-piperidinyl)phenyl]-N4-[2-(isopropylsulfonyl)phenyl]-2,4-pyrimidinediamine (ceritinib) and the SHP2 inhibitor is 6-amino-2-((3S,4S)-4-amino-3-methyl-2-oxa-8-azaspiro[4.5]decan-8-yl)-3-methyl-5-((2-(trifluoromethyl)pyridin-3-yl)thio)pyrimidin-4(3H)-one.

Item 54: The pharmaceutical combination, the pharmaceutical composition, the commercial package, the pharmaceutical combination for use, the pharmaceutical composition for use, the commercial package for use, use of the pharmaceutical combination, use of the pharmaceutical composition, use of the commercial package, or the method of treating a cancer according item 28, wherein the ALK inhibitor is 5-chloro-N2-[2-isopropoxy-5-methyl-4-(4-piperidinyl)phenyl]-N4-[2-(isopropylsulfonyl)phenyl]-2,4-pyrimidinediamine (ceritinib) and the SHP2 inhibitor is 6-amino-2-((3S,4S)-4-amino-3-methyl-2-oxa-8-azaspiro[4.5]decan-8-yl)-5-((3-chloro-2-methylpyridin-4-yl)thio)-3-methylpyrimidin-4(3H)-one.

Item 55: The pharmaceutical combination, the pharmaceutical composition, the commercial package, the pharmaceutical combination for use, the pharmaceutical composition for use, the commercial package for use, use of the pharmaceutical combination, use of the pharmaceutical composition, use of the commercial package, or the method of treating a cancer according item 28, wherein the ALK inhibitor is 5-chloro-N2-[2-isopropoxy-5-methyl-4-(4-piperidinyl)phenyl]-N4-[2-

(isopropylsulfonyl)phenyl]-2,4-pyrimidinediamine (ceritinib) and the SHP2 inhibitor is 6-amino-2-((3S,4S)-4-amino-3-methyl-2-oxa-8-azaspiro[4.5]decan-8-yl)-5-((2,3-dichlorophenyl)thio)-3-methylpyrimidin-4(3H)-one.

Item 56: The pharmaceutical combination, the pharmaceutical composition, the commercial package, the pharmaceutical combination for use, the pharmaceutical composition for use, the commercial package for use, use of the pharmaceutical combination, use of the pharmaceutical composition, use of the commercial package, or the method of treating a cancer according item 28, wherein the ALK inhibitor is 5-chloro-N2-[2-isopropoxy-5-methyl-4-(4-piperidinyl)phenyl]-N4-[2-(isopropylsulfonyl)phenyl]-2,4-pyrimidinediamine (ceritinib) and the SHP2 inhibitor is 6-amino-2-((1R,3R)-1-amino-3-methyl-8-azaspiro[4.5]decan-8-yl)-3-methyl-5-((3-(trifluoromethyl)pyridin-4-yl)thio)pyrimidin-4(3H)-one.

Item 57: The pharmaceutical combination, the pharmaceutical composition, the commercial package, the pharmaceutical combination for use, the pharmaceutical composition for use, the commercial package for use, use of the pharmaceutical combination, use of the pharmaceutical composition, use of the commercial package, or the method of treating a cancer according item 28, wherein the ALK inhibitor is 5-chloro-N2-[2-isopropoxy-5-methyl-4-(4-piperidinyl)phenyl]-N4-[2-(isopropylsulfonyl)phenyl]-2,4-pyrimidinediamine (ceritinib) and the SHP2 inhibitor is 6-amino-2-((1R,3R)-1-amino-3-methyl-8-azaspiro[4.5]decan-8-yl)-5-(2,3-dichlorophenyl)-3-methylpyrimidin-4(3H)-one.

Item 58: The pharmaceutical combination, the pharmaceutical composition, the commercial package, the pharmaceutical combination for use, the pharmaceutical composition for use, the commercial package for use, use of the pharmaceutical combination, use of the pharmaceutical composition, use of the commercial package, or the method of treating a cancer according item 28, wherein the ALK inhibitor is 5-chloro-N2-[2-isopropoxy-5-methyl-4-(4-piperidinyl)phenyl]-N4-[2-(isopropylsulfonyl)phenyl]-2,4-pyrimidinediamine (ceritinib) and the SHP2 inhibitor is 6-amino-2-((3S,4S)-4-amino-3-methyl-2-oxa-8-azaspiro[4.5]decan-8-yl)-5-((2-chloro-3-methoxyphenyl)thio)-3-methylpyrimidin-4(3H)-one.

Item 59: The pharmaceutical combination, the pharmaceutical composition, the commercial package, the pharmaceutical combination for use, the pharmaceutical composition for use, the commercial package for use, use of the pharmaceutical combination, use of the pharmaceutical composition, use of the commercial package, or the method of treating a cancer according item 28, wherein the ALK inhibitor is 5-chloro-N2-[2-isopropoxy-5-methyl-4-(4-piperidinyl)phenyl]-N4-[2-(isopropylsulfonyl)phenyl]-2,4-pyrimidinediamine (ceritinib) and the SHP2 inhibitor is 6-amino-2-((3S,4S)-4-amino-3-ethyl-2-oxa-8-azaspiro[4.5]decan-8-yl)-3-methyl-5-((2-(trifluoromethyl)pyridin-3-yl)thio)pyrimidin-4(3H)-one.

Item 60: The pharmaceutical combination, the pharmaceutical composition, the commercial package, the pharmaceutical combination for use, the pharmaceutical composition for use, the commercial package for use, use of the pharmaceutical combination, use of the pharmaceutical composition, use of the commercial package, or the method of treating a cancer according item 28, wherein the ALK inhibitor is 5-chloro-N2-[2-isopropoxy-5-methyl-4-(4-piperidinyl)phenyl]-N4-[2-(isopropylsulfonyl)phenyl]-2,4-pyrimidinediamine (ceritinib) and the SHP2 inhibitor is 6-amino-5-((3-amino-2-(trifluoromethyl)phenyl)thio)-2-((3S,4S)-4-amino-3-methyl-2-oxa-8-azaspiro[4.5]decan-8-yl)-3-methylpyrimidin-4(3H)-one.

Item 61: The pharmaceutical combination, the pharmaceutical composition, the commercial package, the pharmaceutical combination for use, the pharmaceutical composition for use, the commercial package for use, use of the pharmaceutical combination, use of the pharmaceutical composition, use of the commercial package, or the method of treating a cancer according item 28, wherein the ALK inhibitor is 5-chloro-N2-[2-isopropoxy-5-methyl-4-(4-piperidinyl)phenyl]-N4-[2-(isopropylsulfonyl)phenyl]-2,4-pyrimidinediamine (ceritinib) and the SHP2 inhibitor is (R)-6-amino-2-(1-amino-3,3-difluoro-8-azaspiro[4.5]decan-8-yl)-5-((2-amino-3-chloropyridin-4-yl)thio)-3-methylpyrimidin-4(3H)-one.

Item 62: The pharmaceutical combination, the pharmaceutical composition, the commercial package, the pharmaceutical combination for use, the pharmaceutical composition for use, the commercial package for use, use of the pharmaceutical combination, use of the pharmaceutical composition, use of the commercial package, or the method of treating a cancer according item 28, wherein the ALK inhibitor is 5-chloro-N2-[2-isopropoxy-5-methyl-4-(4-piperidinyl)phenyl]-N4-[2-(isopropylsulfonyl)phenyl]-2,4-pyrimidinediamine (ceritinib) and the SHP2 inhibitor is 6-amino-2-((3S,4S)-4-amino-3-methyl-2-oxa-8-azaspiro[4.5]decan-8-yl)-3-methyl-5-((3-(trifluoromethyl)pyridin-4-yl)thio)pyrimidin-4(3H)-one.

Item 63: The pharmaceutical combination, the pharmaceutical composition, the commercial package, the pharmaceutical combination for use, the pharmaceutical composition for use, the commercial package for use, use of the pharmaceutical combination, use of the pharmaceutical composition, use of the commercial package, or the method of treating a cancer according item 28, wherein the ALK inhibitor is 5-chloro-N2-[2-isopropoxy-5-methyl-4-(4-piperidinyl)phenyl]-N4-[2-(isopropylsulfonyl)phenyl]-2,4-pyrimidinediamine (ceritinib) and the SHP2 inhibitor is 6-amino-2-((1R,3R)-1-amino-3-methyl-8-azaspiro[4.5]decan-8-yl)-5-(4-chlorophenyl)-3-methylpyrimidin-4(3H)-one.

Item 64: The pharmaceutical combination, the pharmaceutical composition, the commercial package, the pharmaceutical combination for use, the pharmaceutical composition for use, the commercial package for use, use of the pharmaceutical combination, use of the pharmaceutical composition, use of the commercial package, or the method of treating a cancer according item 28, wherein the ALK inhibitor is 5-chloro-N2-[2-isopropoxy-5-methyl-4-(4-piperidinyl)phenyl]-N4-[2-(isopropylsulfonyl)phenyl]-2,4-pyrimidinediamine (ceritinib) and the SHP2 inhibitor is 6-amino-2-((1R,3R)-1-amino-3-methyl-8-azaspiro[4.5]decan-8-yl)-3-methyl-5-phenylpyrimidin-4(3H)-one.

Item 65: The pharmaceutical combination, the pharmaceutical composition, the commercial package, the pharmaceutical combination for use, the pharmaceutical composition for use, the commercial package for use, use of the pharmaceutical combination, use of the pharmaceutical composition, use of the commercial package, or the method of treating a cancer according item 28, wherein the ALK inhibitor is 5-chloro-N2-[2-isopropoxy-5-methyl-4-(4-piperidinyl)phenyl]-N4-[2-(isopropylsulfonyl)phenyl]-2,4-pyrimidinediamine (ceritinib) and the SHP2 inhibitor is (R)-6-(1-amino-8-azaspiro[4.5]decan-8-yl)-3-(2,3-dichlorophenyl)-5-methyl-2,5-dihydro-4H-pyrazolo[3,4-d]pyrimidin-4-one.

Item 66: The pharmaceutical combination, the pharmaceutical composition, the commercial package, the pharmaceutical combination for use, the pharmaceutical composition for use, the commercial package for use, use of the pharmaceutical combination, use of the pharmaceutical composition, use of the commercial package, or the method of treating a cancer according item 28, wherein the ALK inhibitor is 5-chloro-N2-[2-isopropoxy-5-methyl-4-(4-piperidinyl)phenyl]-N4-[2-(isopropylsulfonyl)phenyl]-2,4-pyrimidinediamine (ceritinib) and the SHP2 inhibitor is 2-(4-(aminomethyl)-4-methylpiperidin-1-yl)-5-(2,3-dichlorophenyl)-3,7-dihydro-4H-pyrrolo[2,3-d]pyrimidin-4-one.

Item 67: The pharmaceutical combination, the pharmaceutical composition, the commercial package, the pharmaceutical combination for use, the pharmaceutical composition for use, the commercial package for use, use of the pharmaceutical combination, use of the pharmaceutical composition, use of the commercial package, or the method of treating a cancer according item 28, wherein the ALK inhibitor is 5-chloro-N2-[2-isopropoxy-5-methyl-4-(4-piperidinyl)phenyl]-N4-[2-(isopropylsulfonyl)phenyl]-2,4-pyrimidinediamine (ceritinib) and the SHP2 inhibitor is (3S,4S)-8-(3-(2,3-dichloropyridin-4-yl)-1H-pyrazolo[3,4-b]pyrazin-6-yl)-3-methyl-2-oxa-8-azaspiro[4.5]decan-4-amine.

Item 668: The pharmaceutical combination, the pharmaceutical composition, the commercial package, the pharmaceutical combination for use, the pharmaceutical composition for use, the commercial package for use, use of the pharmaceutical combination, use of the pharmaceutical composition, use of the commercial package, or the method of treating a cancer according item 28, wherein the ALK inhibitor is 5-chloro-N2-[2-isopropoxy-5-methyl-4-(4-piperidinyl)phenyl]-N4-[2-(isopropylsulfonyl)phenyl]-2,4-pyrimidinediamine (ceritinib) and the SHP2 inhibitor is 3-(6-amino-2-methylpyridin-3-yl)-6-((1R,3R)-1-amino-3-methyl-8-azaspiro[4.5]decan-8-yl)-5-methyl-2,5-dihydro-4H-pyrazolo[3,4-d]pyrimidin-4-one.

Item 69: The pharmaceutical combination, the pharmaceutical composition, the commercial package, the pharmaceutical combination for use, the pharmaceutical composition for use, the commercial package for use, use of the pharmaceutical combination, use of the pharmaceutical composition, use of the commercial package, or the method of treating a cancer according item 28, wherein the ALK inhibitor is 5-chloro-N2-[2-isopropoxy-5-methyl-4-(4-piperidinyl)phenyl]-N4-[2-(isopropylsulfonyl)phenyl]-2,4-pyrimidinediamine (ceritinib) and the SHP2 inhibitor is (R)-3-(6-amino-2-methylpyridin-3-yl)-6-(1-amino-3,3-difluoro-8-azaspiro[4.5]decan-8-yl)-5-methyl-2,5-dihydro-4H-pyrazolo[3,4-d]pyrimidin-4-one.

Item 70: The pharmaceutical combination, the pharmaceutical composition, the commercial package, the pharmaceutical combination for use, the pharmaceutical composition for use, the commercial package for use, use of the pharmaceutical combination, use of the pharmaceutical composition, use of the commercial package, or the method of treating a cancer according item 28, wherein the ALK inhibitor is 5-chloro-N2-[2-isopropoxy-5-methyl-4-(4-piperidinyl)phenyl]-N4-[2-(isopropylsulfonyl)phenyl]-2,4-pyrimidinediamine (ceritinib) and the SHP2 inhibitor is 6-((3S,4S)-4-amino-3-methyl-2-oxa-8-azaspiro[4.5]decan-8-yl)-3-(3-chloro-2-(cyclopropylamino)pyridin-4-yl)-5-methyl-2,5-dihydro-4H-pyrazolo[3,4-d]pyrimidin-4-one.

Item 71: The pharmaceutical combination, the pharmaceutical composition, the commercial package, the pharmaceutical combination for use, the pharmaceutical composition for use, the commercial package for use, use of the pharmaceutical combination, use of the pharmaceutical composition, use of the commercial package, or the method of treating a cancer according item 28, wherein the ALK inhibitor is 5-chloro-N2-[2-isopropoxy-5-methyl-4-(4-piperidinyl)phenyl]-N4-[2-(isopropylsulfonyl)phenyl]-2,4-pyrimidinediamine (ceritinib) and the SHP2 inhibitor is 2-((3S,4S)-4-amino-3-methyl-2-oxa-8-azaspiro[4.5]decan-8-yl)-5-(3-chloro-2-methoxypyridin-4-yl)-3-methyl-3,7-dihydro-4H-pyrrolo[2,3-d]pyrimidin-4-one.

Item 72: The pharmaceutical combination, the pharmaceutical composition, the commercial package, the pharmaceutical combination for use, the pharmaceutical composition for use, the commercial package for use, use of the pharmaceutical combination, use of the pharmaceutical composition, use of the commercial package, or the method of treating a cancer according item 28, wherein the ALK inhibitor is 5-chloro-N2-[2-isopropoxy-5-methyl-4-(4-piperidinyl)phenyl]-N4-[2-(isopropylsulfonyl)phenyl]-2,4-pyrimidinediamine (ceritinib) and the SHP2 inhibitor is N-(3-((3-amino-5-(4-amino-4-methylpiperidin-1-yl)pyrazin-2-yl)thio)-2-chlorophenyl)-2-hydroxy-4-oxo-4H-pyrido[1,2-a]pyrimidine-3-carboxamide.

Item 73: The pharmaceutical combination, the pharmaceutical composition, the commercial package, the pharmaceutical combination for use, the pharmaceutical composition for use, the commercial package for use, use of the pharmaceutical combination, use of the pharmaceutical composition, use of the commercial package, or the method of treating a cancer according item 28, wherein the ALK inhibitor is 5-chloro-N2-[2-isopropoxy-5-methyl-4-(4-piperidinyl)phenyl]-N4-[2-(isopropylsulfonyl)phenyl]-2,4-pyrimidinediamine (ceritinib) and the SHP2 inhibitor is N-(3-((3-amino-5-((3S,4S)-4-amino-3-methyl-2-oxa-8-azaspiro[4.5]decan-8-yl)pyrazin-2-yl)thio)-2-chlorophenyl)-2-hydroxy-4-oxo-6,7,8,9-tetrahydro-4H-pyrido[1,2-a]pyrimidine-3-carboxamide.

Item 74: The pharmaceutical combination, the pharmaceutical composition, the commercial package, the pharmaceutical combination for use, the pharmaceutical composition for use, the commercial package for use, use of the pharmaceutical combination, use of the pharmaceutical composition, use of the commercial package, or the method of treating a cancer according item 28, wherein the ALK inhibitor is 5-chloro-N2-[2-isopropoxy-5-methyl-4-(4-piperidinyl)phenyl]-N4-[2-(isopropylsulfonyl)phenyl]-2,4-pyrimidinediamine (ceritinib) and the SHP2 inhibitor is N-(3-((3-amino-5-(4-amino-4-methylpiperidin-1-yl)pyrazin-2-yl)thio)-2-chlorophenyl)-4-hydroxy-2-oxo-1-phenyl-2,5-dihydro-1H-pyrrole-3-carboxamide.

Item 75: The pharmaceutical combination, the pharmaceutical composition, the commercial package, the pharmaceutical combination for use, the pharmaceutical composition for use, the commercial package for use, use of the pharmaceutical combination, use of the pharmaceutical composition, use of the commercial package, or the method of treating a cancer according item 28, wherein the ALK inhibitor is 5-chloro-N2-[2-isopropoxy-5-methyl-4-(4-piperidinyl)phenyl]-N4-[2-(isopropylsulfonyl)phenyl]-2,4-pyrimidinediamine (ceritinib) and the SHP2 inhibitor is (R)—N-(3-((3-amino-5-(1-amino-8-azaspiro[4.5]decan-8-yl)pyrazin-2-yl)thio)-2-chlorophenyl)-2-hydroxy-4-oxo-6,7,8,9-tetrahydro-4H-pyrido[1,2-a]pyrimidine-3-carboxamide.

Item 76: The pharmaceutical combination, the pharmaceutical composition, the commercial package, the pharmaceutical combination for use, the pharmaceutical composition for use, the commercial package for use, use of the pharmaceutical combination, use of the pharmaceutical composition, use of the commercial package, or the method of treating a cancer according item 28, wherein the ALK inhibitor is 5-chloro-N2-[2-isopropoxy-5-methyl-4-(4-piperidinyl)phenyl]-N4-[2-(isopropylsulfonyl)phenyl]-2,4-pyrimidinediamine (ceritinib) and the SHP2 inhibitor is N-(3-((3-amino-5-(4-(aminomethyl)-4-methylpiperidin-1-yl)pyrazin-2-yl)thio)-2-chlorophenyl)-2-hydroxy-4-oxo-6,7,8,9-tetrahydro-4H-pyrido[1,2-a]pyrimidine-3-carboxamide.

Item 77: The pharmaceutical combination, the pharmaceutical composition, the commercial package, the pharmaceutical combination for use, the pharmaceutical composition for use, the commercial package for use, use of the pharmaceutical combination, use of the pharmaceutical composition, use of the commercial package, or the method of treating a cancer according item 28, wherein the ALK inhibitor is 5-chloro-N2-[2-isopropoxy-5-methyl-4-(4-piperidinyl)phenyl]-N4-[2-(isopropylsulfonyl)phenyl]-2,4-pyrimidinediamine (ceritinib) and the SHP2 inhibitor is (R)—N-(3-((3-amino-5-(1-amino-3,3-difluoro-8-azaspiro[4.5]decan-8-yl)pyrazin-2-yl)thio)-2-chlorophenyl)-2-hydroxy-4-oxo-6,7,8,9-tetrahydro-4H-pyrido[1,2-a]pyrimidine-3-carboxamide.

Item 78: The pharmaceutical combination, the pharmaceutical composition, the commercial package, the pharmaceutical combination for use, the pharmaceutical composition for use, the commercial package for use, use of the pharmaceutical combination, use of the pharmaceutical composition, use of the commercial package, or the method of treating a cancer according item 28, wherein the ALK inhibitor is 5-chloro-N2-[2-isopropoxy-5-methyl-4-(4-piperidinyl)phenyl]-N4-[2-(isopropylsulfonyl)phenyl]-2,4-pyrimidinediamine (ceritinib) and the SHP2 inhibitor is N-(3-((3-amino-5-(4-(aminomethyl)-4-methylpiperidin-1-yl)pyrazin-2-yl)thio)-2-chlorophenyl)-2-hydroxy-4-oxo-4H-pyrido[1,2-a]pyrimidine-3-carboxamide.

Item 79: The pharmaceutical combination, the pharmaceutical composition, the commercial package, the pharmaceutical combination for use, the pharmaceutical composition for use, the commercial package for use, use of the pharmaceutical combination, use of the pharmaceutical composition, use of the commercial package, or the method of treating a cancer according item 28, wherein the ALK inhibitor is 5-chloro-N2-[2-isopropoxy-5-methyl-4-(4-piperidinyl)phenyl]-N4-[2-(isopropylsulfonyl)phenyl]-2,4-pyrimidinediamine (ceritinib) and the SHP2 inhibitor is N-(3-((3-amino-5-(4-amino-4-(fluoromethyl)piperidin-1-yl)pyrazin-2-yl)thio)-2-chlorophenyl)-2-hydroxy-4-oxo-6,7,8,9-tetrahydro-4H-pyrido[1,2-a]pyrimidine-3-carboxamide.

Item 80: The pharmaceutical combination, the pharmaceutical composition, the commercial package, the pharmaceutical combination for use, the pharmaceutical composition for use, the commercial package for use, use of the pharmaceutical combination, use of the pharmaceutical composition, use of the commercial package, or the method of treating a cancer according item 28, wherein the ALK inhibitor is 5-chloro-N2-[2-isopropoxy-5-methyl-4-(4-piperidinyl)phenyl]-N4-[2-(isopropylsulfonyl)phenyl]-2,4-pyrimidinediamine (ceritinib) and the SHP2 inhibitor is N-(3-((3-amino-5-(4-amino-4-(fluoromethyl)piperidin-1-yl)pyrazin-2-yl)thio)-2-chlorophenyl)-2-hydroxy-4-oxo-4H-pyrido[1,2-a]pyrimidine-3-carboxamide.

Item 81: The pharmaceutical combination, the pharmaceutical composition, the commercial package, the pharmaceutical combination for use, the pharmaceutical composition for use, the commercial package for use, use of the pharmaceutical combination, use of the pharmaceutical composition, use of the commercial package, or the method of treating a cancer according item 28, wherein the ALK inhibitor is 5-chloro-N2-[2-isopropoxy-5-methyl-4-(4-piperidinyl)phenyl]-N4-[2-(isopropylsulfonyl)phenyl]-2,4-pyrimidinediamine (ceritinib) and the SHP2 inhibitor is (S)—N-(3-((3-amino-5-(4-amino-2-oxa-8-azaspiro[4.5]decan-8-yl)pyrazin-2-yl)thio)-2-chlorophenyl)-2-hydroxy-4-oxo-6,7,8,9-tetrahydro-4H-pyrido[1,2-a]pyrimidine-3-carboxamide.

Item 82: The pharmaceutical combination, the pharmaceutical composition, the commercial package, the pharmaceutical combination for use, the pharmaceutical composition for use, the commercial package for use, use of the pharmaceutical combination, use of the pharmaceutical composition, use of the commercial package, or the method of treating a cancer according item 28, wherein the ALK inhibitor is 5-chloro-N2-[2-isopropoxy-5-methyl-4-(4-piperidinyl)phenyl]-N4-[2-(isopropylsulfonyl)phenyl]-2,4-pyrimidinediamine (ceritinib) and the SHP2 inhibitor is N-(3-((3-amino-5-(4-amino-4-methylpiperidin-1-yl)pyrazin-2-yl)thio)-2-chlorophenyl)-5-benzyl-4-hydroxy-1-methyl-2-oxo-2,5-dihydro-1H-pyrrole-3-carboxamide.

DETAILED DESCRIPTION OF THE INVENTION

Definitions

Figure 1:
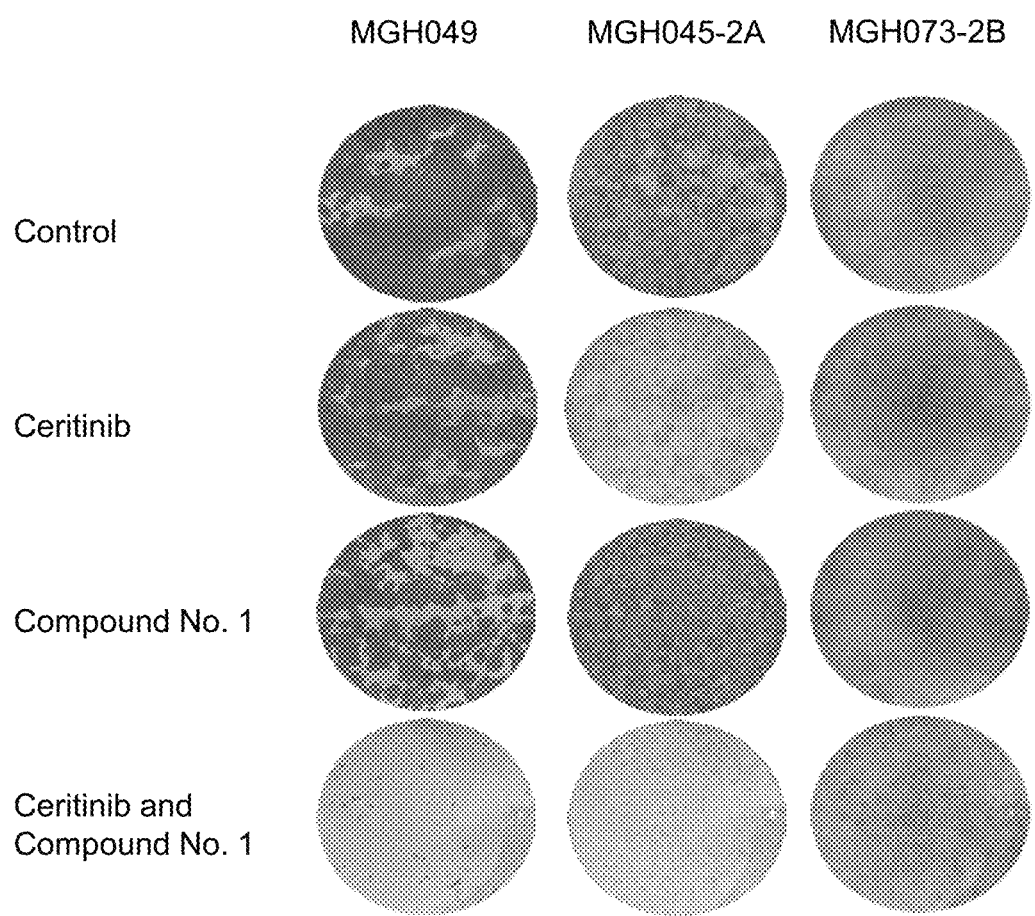
FIG. 1. Images obtained from cell colony formation assays showing SHP2 inhibitor Compound No. 1 enhances the anti-proliferation activity of ceritinib in ALK positive NSCLC cells. Cells were exposed to ceritinib (0.5 µM), Compound No. 1 (5 µM), or the combination for 14 days. For each cell line, all dishes were fixed, stained and photographed at the same time.

The general terms used herein are defined with the following meanings, unless explicitly stated otherwise.

The terms "comprising" and "including" are used herein in their open-ended and non-limiting sense unless otherwise noted.

The terms "a" and "an" and "the" and similar references in the context of describing the invention (especially in the context of the following claims) are to be construed to cover both the singular and the plural, unless otherwise indicated herein or clearly contradicted by context. Where the plural form is used for compounds, salts, and the like, this is taken to mean also a single compound, salt, or the like.

The term "combination" or "pharmaceutical combination" as used herein refers to either a fixed combination in one unit dosage form (e.g. capsule, tablet or sachet), a non-fixed combination or a kit of parts for the combined administration where an ALK inhibitor or a pharmaceutically acceptable salt thereof, and a SHP2 inhibitor, or a pharmaceutically acceptable salt thereof, may be administered simultaneously, independently at the same time or separately within time intervals that allow the combination partners to show a cooperative, e.g., synergistic effect, or an additive effect.

The term "ALK inhibitor" as used herein refers to a compound which targets, decreases or inhibits the synthesis or biological activity of anaplastic lymphoma kinase (ALK). Particularly, the "ALK inhibitor" can be a compound that inhibits ALK with the $IC_{50}$ of less than 1 µM, measured by a Caliper mobility shift assay. The Caliper mobility shift technology is based on the separation of particles of different charges and sizes in an electrical field, similar to capillary electrophoresis. The Caliper kinase assays utilize fluorescently labeled peptides as kinase substrates. The phosphorylation of the peptide in the course of the reaction introduces additional negative charges via the phosphate and hence permits its separation from the phosphorylated peptide. Both, the separation and the detection of the labeled peptides take place in the microfluidic system of the Caliper Lab Chip. The LabChips have 12 "sippers" enabling the parallel analysis of 12 samples at the same time. The fact that both, unphosphorylated peptide (substrate) and phosphorylated peptide (product) are measured and that the separation makes the readout relatively insensitive to interference by fluorescent compounds results in the excellent data quality of this assay. General assay procedure can be performed at 30° C. for 60 min in a total volume of 9 µL including 0.050 µL of compound dilution or pure DMSO, respectively. The reaction can be terminated by the addition of 16 µL of stop solution (100 mM Hepes, 5% (v/v) DMSO, 0.1% (v/v) Coating reagent, 10 mM EDTA, 0.015% (v/v) Brij 35). After termination of the reactions, the plates are transferred into the Caliper LabChip 3000 workstation for analysis. The effect of a compound on the enzymatic activity is obtained from the linear progress curves in the absence and presence of the compound and routinely determined from one reading (end point measurement). According to the present invention, the ALK inhibitor can be for example a compound selected from the group consisting of 5-chloro-N2-[2-isopropoxy-5-methyl-4-(4-piperidinyl)phenyl]-N4-[2-(isopropylsulfonyl)phenyl]-2,4-pyrimidinediamine (ceritinib), (10R)-7-Amino-12-fluoro-2,10,16-trimethyl-15-oxo-10,15,16,17-tetrahydro-2H-8,4-(metheno)pyrazolo[4,3-h][2,5,11]-benzoxadiazacyclotetradecine-3-carbonitrile (lorlatinib; PF-06463922),

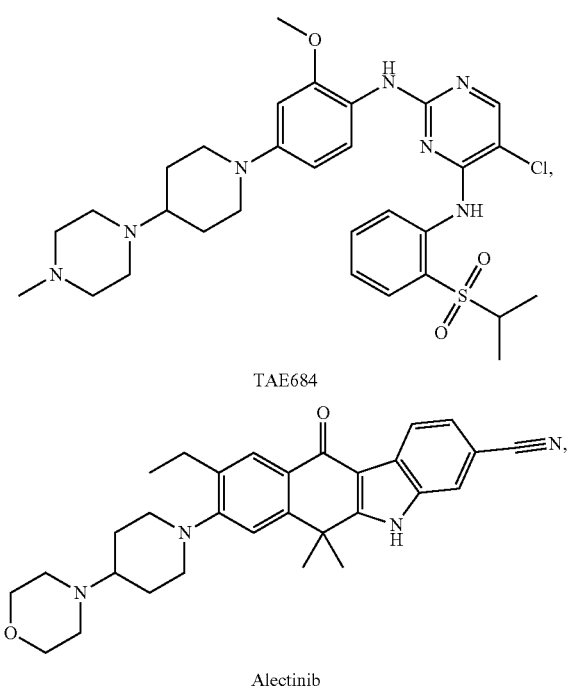

TAE684

Alectinib

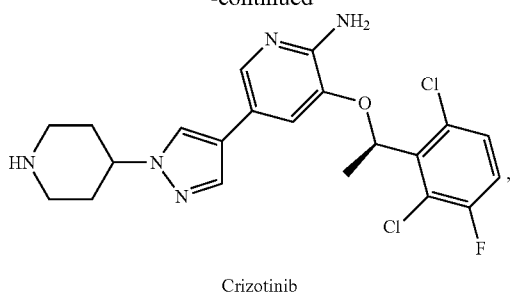

Crizotinib

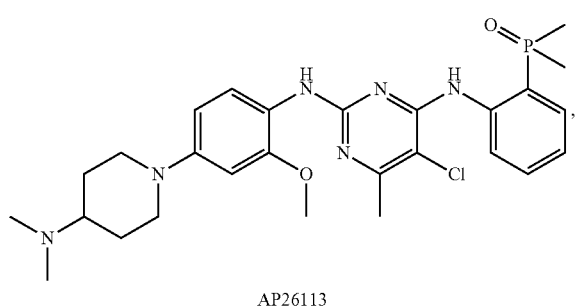

AP26113

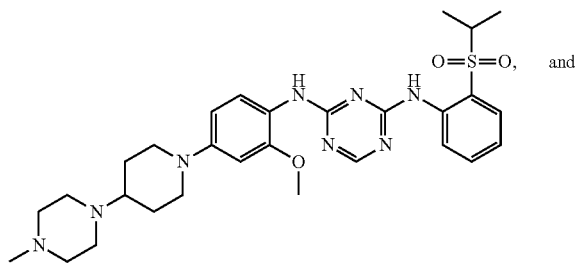

ASP3026

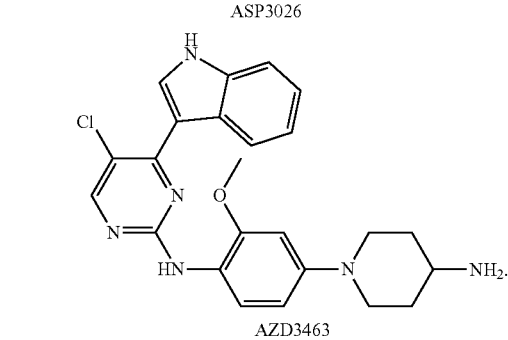

AZD3463

Preferably, the ALK inhibitor is ceritinib, i.e. 5-chloro-N2-(2-isopropoxy-5-methyl-4-(piperidin-4-yl)phenyl)-N4-[2-(propane-2-sulfonyl)-phenyl]-pyrimidine-2,4-diamine, or a pharmaceutically acceptable salt thereof. Ceritinib is a compound of Formula (I), and is described in Example 7 (Compound 66) of WO2008/073687:

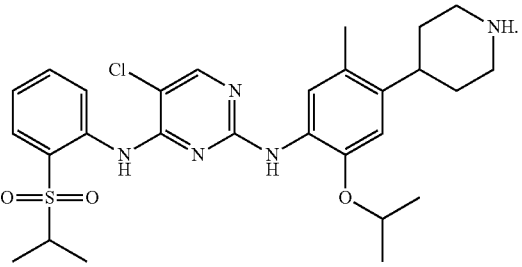

Formula (I)

The term "SHP2 inhibitor" as used herein refers to a compound which targets, decreases or inhibits the biological activity of the non-receptor protein tyrosine phosphatase SHP2. Particularly, the "SHP2 inhibitor" can be a compound that inhibits SHP2 with an $IC_{50}$ of less than 0.5 µM, measured by the SHP2 inhibition assay as described herein and in Nature, 2016, vol. 535, p. 148. The SHP2 inhibitor can be for example any compound from Table 1.

"ALK-rearranged cancer" or "ALK-positive cancer" refer to a cancer with the ALK gene rearranged, mutated, or amplified. This can cause aberrant expression of full-length ALK or causing ALK fusion proteins to drive proliferation. There exist several different ALK fusion partners.

"ALK-positive cancer resistant to an ALK inhibitor" refers to a cancer or tumor that either fails to respond favorably to treatment with prior ALK inhibitors, or alternatively, recurs or relapses after responding favorably to ALK inhibitors. The cancer or tumor may be resistant or refractory at the beginning of treatment or it may become resistant or refractory during treatment. One mechanism for tumor resistance when treated with ALK inhibitors is for mutations to appear in the ALK gene. This mechanism has been demonstrated in a clinical trial in Crizotinib treated patients with ALK positive tumors (mostly non-small cell lung carcinoma). Some of these resistance mutations are similar to the mutations found in neuroblastoma. While not wished to be bound by any theory, it is hypothesized that these resistance mutations lead to activation of ALK to further drive the proliferation of the tumor. Alternatively, by-pass biochemical pathways get activated via various mechanisms that counterbalance inhibition of ALK, which in turn promote proliferation. Those are referred to as "ALK-independent resistance".

The term "COMBINATION OF THE INVENTION", as used herein, refers to a pharmaceutical combination which comprises (i) an ALK inhibitor or a pharmaceutically acceptable salt thereof, and (ii) a SHP2 inhibitor, or a pharmaceutically acceptable salt thereof, and optionally at least one pharmaceutically acceptable carrier. The term "COMBINATION OF THE INVENTION" is also taken to mean a pharmaceutical combination comprising:

A) (i) an ALK inhibitor, or a pharmaceutically acceptable salt thereof, selected from 5-chloro-N2-[2-isopropoxy-5-methyl-4-(4-piperidinyl)phenyl]-N4-[2-(isopropylsulfonyl)phenyl]-2,4-pyrimidinediamine (ceritinib), 9-Ethyl-6,6-dimethyl-8-[4-(4-morpholinyl)-1-piperidinyl]-11-oxo-6,11-dihydro-5H-benzo[b]carbazole-3-carbonitrile (alectinib) and (10R)-7-Amino-12-fluoro-2,10,16-trimethyl-15-oxo-10,15,16,17-tetrahydro-2H-8,4-(metheno)pyrazolo[4,3-h][2,5,11]-benzoxadiazacyclotetradecine-3-carbonitrile (loratinib), and (ii) a SHP2 inhibitor, or a pharmaceutically acceptable salt thereof, and optionally at least one pharmaceutically acceptable carrier;

B) (i) an ALK inhibitor, or a pharmaceutically acceptable salt thereof, selected from 5-chloro-N2-[2-isopropoxy-5-methyl-4-(4-piperidinyl)phenyl]-N4-[2-(isopropylsulfonyl)phenyl]-2,4-pyrimidinediamine (ceritinib), 9-Ethyl-6,6-dimethyl-8-[4-(4-morpholinyl)-1-piperidinyl]-11-oxo-6,11-dihydro-5H-benzo[b]carbazole-3-carbonitrile (alectinib) and (10R)-7-Amino-12-fluoro-2,10,16-trimethyl-15-oxo-10,15,16,17-tetrahydro-2H-8,4-(metheno)pyrazolo[4,3-h][2,5,11]-benzoxadiazacyclotetradecine-3-carbonitrile (loratinib), and (ii) a SHP2 inhibitor of Table 1, or a pharmaceutically acceptable salt thereof, and optionally at least one pharmaceutically acceptable carrier;

C) (i) 5-chloro-N2-[2-isopropoxy-5-methyl-4-(4-piperidinyl)phenyl]-N4-[2-(isopropylsulfonyl)phenyl]-2,4-pyrimidinediamine (ceritinib), or a pharmaceutically acceptable salt thereof, and (ii) a SHP2 inhibitor, or a pharmaceutically acceptable salt thereof, and optionally at least one pharmaceutically acceptable carrier, and D) (i) 5-chloro-N2-[2-isopropoxy-5-methyl-4-(4-piperidinyl)phenyl]-N4-[2-(isopropylsulfonyl)phenyl]-2,4-pyrimidinediamine (ceritinib), or a pharmaceutically acceptable salt thereof, and (ii) a SHP2 inhibitor of Table 1, or a pharmaceutically acceptable salt thereof, and optionally at least one pharmaceutically acceptable carrier.

The term "fixed combination" means that the active ingredients, i.e. an ALK inhibitor, as defined herein, and one or more combination partners, i.e. a SHP2 inhibitor, as defined herein, are administered to a patient simultaneously in the form of a single entity or unit dosage form. The term "non-fixed combination" means that the active ingredients, i.e. an ALK inhibitor, as defined herein, and one or more combination partners, i.e. a SHP2 inhibitor, as defined herein, are administered to a patient as separate entities either simultaneously or sequentially with no specific time limits, wherein such administration provides therapeutically effective levels of the two compounds in the body of the patient. This applies to combinations of two active ingredients and also to a cocktail therapy, e.g. the administration of three or more active ingredients.

The term "a pharmaceutical preparation" is defined herein to refer to especially "a kit of parts" in the sense that the combination partners, i.e. an ALK inhibitor and a SHP2 inhibitor, as defined herein can be dosed independently or by use of different fixed combinations with distinguished amounts of the combination partners, e.g. an ALK inhibitor and a SHP2 inhibitor, simultaneously or at different time points. The parts of the kit of parts can then e.g., be administered simultaneously or chronologically staggered, that is at different time points and with equal or different time intervals for any part of the kit of parts. The ratio of the total amounts of one combination partner to the other combination partner to be administered in the pharmaceutical preparation can be varied, e.g., in order to cope with the needs of a patient sub-population to be treated or the needs of the single patient.

The term "pharmaceutical composition" is defined herein to refer to a mixture or solution containing at least one active ingredient or therapeutic agent to be administered to a subject, e.g., a mammal or human, in order to prevent or treat a particular disease or condition affecting the mammal or human, in particular a proliferative disease, such as cancer, particularly lung cancer.

The terms "drug", "active substance", "active ingredient", "active agent", "agent" are to be understood as meaning a compound in free form or in the form of a pharmaceutically acceptable salt, in particular compounds specified herein. Herein, the term an ALK inhibitor is also referred to as "combination partner (i)". Similarly, the term a SHP2 inhibitor is also referred to as "combination partner (ii)

The term "co-administration" or "combined administration" as used herein is defined to encompass the administration of the selected active ingredients to a single subject in need thereof (e.g. a patient), and are intended to include treatment regimens in which the agents are not necessarily administered by the same route of administration or at the same time.

The term "treat", "treating", "treatment" or "therapy" as used herein comprises a treatment relieving, reducing or alleviating at least one symptom in a subject or effecting a delay of progression of a disease. For example, treatment can be the diminishment of one or several symptoms of a disorder or complete eradication of a disorder, such as cancer. Within the meaning of the present invention, the term "treat" also denotes to arrest, delay the onset (i.e., the period prior to clinical manifestation of a disease) and/or reduce the risk of developing or worsening a disease. The term "protect" is used herein to mean prevent delay or treat, or all, as appropriate, development or continuance or aggravation of a disease in a subject, e.g., a mammal or human.

The term "prevent", "preventing" or "prevention" as used herein comprises the prevention of at least one symptom associated with or caused by the state, disease or disorder being prevented.

The term "jointly therapeutically effective amount" as used herein means the amount at which the therapeutic agents, when given separately (in a chronologically staggered manner, especially a sequence-specific manner) to a warm-blooded animal, especially to a human to be treated, show a (additive, but preferably synergistic) interaction (joint therapeutic effect). Whether this is the case can be determined inter alia by following the blood levels, showing that both compounds are present in the blood of the human to be treated at least during certain time intervals.

The term "pharmaceutically effective amount" of a combination of therapeutic agents is an amount sufficient to provide an observable improvement over the baseline observable signs and symptoms of the disorder treated with the combination.

The term "synergistic effect" as used herein refers to an effect of at least two therapeutic agents: an ALK inhibitor, as defined herein, and at least one SHP2 inhibitor, as defined herein, which is greater than the simple addition of the effects of each drug administered by themselves. The effect can be, for example, slowing the symptomatic progression of a proliferative disease, such as cancer, particularly lung cancer, or symptoms thereof. A synergistic effect can be calculated as shown in the examples. Analogously, a "synergistically effective amount" refers to the amount needed to obtain a synergistic effect.

The term "subject" or "patient" as used herein includes animals, which are capable of suffering from or afflicted with a proliferative disease, such as a cancer or any disorder involving, directly or indirectly, a cancer, particularly lung cancer. Examples of subjects include mammals, e.g., humans, dogs, cows, horses, pigs, sheep, goats, cats, mice, rabbits, rats and transgenic non-human animals. In the preferred embodiment, the subject is a human, e.g., a human suffering from, at risk of suffering from, or potentially capable of suffering from a proliferative disease, such as cancer, particularly ALK-positive cancer, such as NSCLC.

The term about" or "approximately" shall have the meaning of within 10%, more preferably within 5%, of a given value or range.

DESCRIPTION OF THE INVENTION AND PREFERRED EMBODIMENTS

It has now been found that a combination of an inhibitor of anaplastic lymphoma kinase (ALK) and an inhibitor of Src Homolgy-2 phosphatase (SHP2) shows synergistic combination activity in an in vitro cell proliferation assay and in an in vivo xenograft model (See experimental section) and may therefore be effective for the treatment of a proliferative disease, such as cancer, in particular ALK-rearranged or ALK-positive cancer, such as non-small cell lung cancer.

Specifically, it has now been found that a combination of 5-chloro-N2-[2-isopropoxy-5-methyl-4-(4-piperidinyl)phenyl]-N4-[2-(isopropylsulfonyl)phenyl]-2,4-pyrimidinediamine (ceritinib), or a pharmaceutically acceptable salt thereof, and an inhibitor of SHP2, or a pharmaceutically acceptable salt thereof, shows synergistic combination activity in an in vitro cell proliferation assay as shown in the experimental section and may therefore be effective for the treatment of a proliferative disease, such as cancer.

Based on the synergistic combination activity shown in the experimental section, it would be expected that the combination of
- (i) An ALK inhibitor, for example 5-chloro-N2-[2-isopropoxy-5-methyl-4-(4-piperidinyl)phenyl]-N4-[2-(isopropylsulfonyl)phenyl]-2,4-pyrimidinediamine (ceritinib), or a pharmaceutically acceptable salt thereof and
- (ii) a SHP2 inhibitor, or a pharmaceutically acceptable salt thereof, would result in an unexpected improvement in the treatment of proliferative diseases, particularly cancer, and more particularly lung cancer. In particular, the unexpected improvement allows for the treatment of ALK-rearranged cancer, such as anaplastic large-cell lymphoma, gastric cancer, colorectal cancer, neuroblastoma, inflammatory myofibroblastic tumor, renal cancer, pancreatic cancer or NSCLC, that may be even resistant to ALK inhibitors alone. In one embodiment the cancer is resistant to ALK inhibitors due to activated bypass signaling pathways.

When administered simultaneously or sequentially, 5-chloro-N2-[2-isopropoxy-5-methyl-4-(4-piperidinyl)phenyl]-N4-[2-(isopropylsulfonyl)phenyl]-2,4-pyrimidinediamine (ceritinib), or a pharmaceutically acceptable salt thereof, and a SHP2 inhibitor, or a pharmaceutically acceptable salt thereof, interact in a synergistic manner to strongly inhibit cell proliferation and would be thus surprisingly efficacious in the treatment of lung cancer. In particular, the unexpected improvement allows for the treatment of ALK-rearranged NSCLCs that may be resistant to ALK inhibitors alone due to activated bypass signaling pathways.

One aspect of the present invention are pharmaceutical combinations comprising:
- (i) an ALK inhibitor, or a pharmaceutically acceptable salt thereof, and
- (ii) a SHP2 inhibitor, or a pharmaceutically acceptable salt thereof.

In another aspect is such a combination further comprising at least one pharmaceutically acceptable carrier.

Another aspect of the present invention are pharmaceutical combinations comprising:
- (i) 5-chloro-N2-[2-isopropoxy-5-methyl-4-(4-piperidinyl)phenyl]-N4-[2-(isopropylsulfonyl)phenyl]-2,4-pyrimidinediamine (ceritinib), or a pharmaceutically acceptable salt thereof, and
- (ii) a SHP2 inhibitor, or a pharmaceutically acceptable salt thereof.

In another aspect is such a combination further comprising at least one pharmaceutically acceptable carrier.

Various enumerated embodiments of such aspects invention are described herein. It will be recognized that features specified in each embodiment may be combined with other specified features to provide further embodiments of the present invention.

Embodiment 1. A pharmaceutical combination comprising:
- (i) an ALK inhibitor, or a pharmaceutically acceptable salt thereof, selected from 5-chloro-N2-[2-isopropoxy-5-methyl-4-(4-piperidinyl)phenyl]-N4-[2-(isopropylsulfonyl)phenyl]-2,4-pyrimidinediamine (ceritinib), 9-Ethyl-6,6-dimethyl-8-[4-(4-morpholinyl)-1-piperidinyl]-11-oxo-6,11-dihydro-5H-benzo[b]carbazole-3-carbonitrile (alectinib) and (10R)-7-Amino-12-fluoro-2,10,16-trimethyl-15-oxo-10,15,16,17-tetrahydro-2H-8,4-(metheno)pyrazolo[4,3-h][2,5,11]-benzoxadiazacyclotetradecine-3-carbonitrile (loratinib), and
- (ii) a SHP2 inhibitor, or a pharmaceutically acceptable salt thereof.

Embodiment 2. A pharmaceutical combination comprising:
- (i) an ALK inhibitor, or a pharmaceutically acceptable salt thereof, selected from 5-chloro-N2-[2-isopropoxy-5-methyl-4-(4-piperidinyl)phenyl]-N4-[2-(isopropylsulfonyl)phenyl]-2,4-pyrimidinediamine (ceritinib), 9-Ethyl-6,6-dimethyl-8-[4-(4-morpholinyl)-1-piperidinyl]-11-oxo-6,11-dihydro-5H-benzo[b]carbazole-3-carbonitrile (alectinib) and (10R)-7-Amino-12-fluoro-2,10,16-trimethyl-15-oxo-10,15,16,17-tetrahydro-2H-8,4-(metheno)pyrazolo[4,3-h][2,5,11]-benzoxadiazacyclotetradecine-3-carbonitrile (loratinib), and
- (ii) a SHP2 inhibitor of Table 1, or a pharmaceutically acceptable salt thereof,

TABLE 1

| Compound No. | Structure | Name |
|---|---|---|
| 1 | 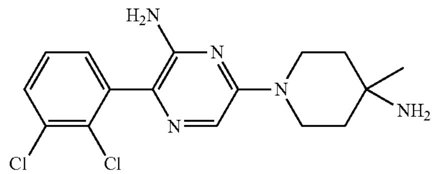 [SMILES: CC1(N)CCN(c2cnc(-c3cccc(Cl)c3Cl)c(N)n2)CC1] | 6-(4-amino-4-methylpiperidin-1-yl)-3-(2,3-dichlorophenyl)pyrazin-2-amine |
| 2 | 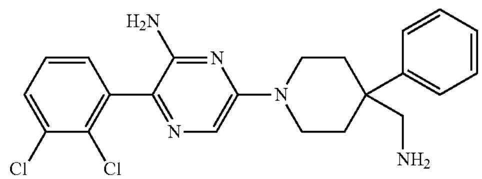 [SMILES: NCC1(c2ccccc2)CCN(c2cnc(-c3cccc(Cl)c3Cl)c(N)n2)CC1] | 6-(4-(aminomethyl)-4-phenylpiperidin-1-yl)-3-(2,3-dichlorophenyl)pyrazin-2-amine |
| 3 | 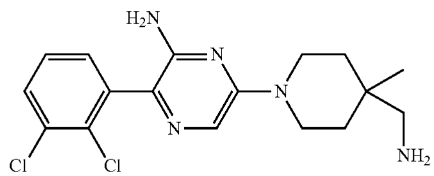 [SMILES: CC1(CN)CCN(c2cnc(-c3cccc(Cl)c3Cl)c(N)n2)CC1] | 6-(4-(aminomethyl)-4-methylpiperidin-1-yl)-3-(2,3-dichlorophenyl)pyrazin-2-amine |
| 4 | 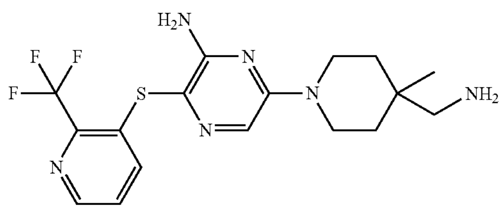 [SMILES: CC1(CN)CCN(c2cnc(Sc3cccnc3C(F)(F)F)c(N)n2)CC1] | 6-(4-(aminomethyl)-4-methylpiperidin-1-yl)-3-((2-(trifluoromethyl)pyridin-3-yl)thio)pyrazin-2-amine |
| 5 | 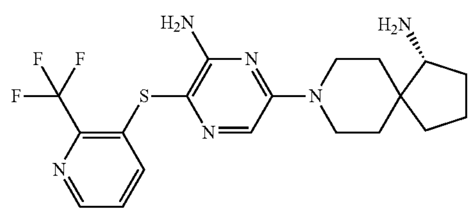 [SMILES: Nc1nc(N2CCC3(CCC[C@H]3N)CC2)cnc1Sc1cccnc1C(F)(F)F] | (R)-8-(6-amino-5-((2-(trifluoromethyl)pyridin-3-yl)thio)pyrazin-2-yl)-8-azaspiro[4.5]decan-1-amine |
| 6 | 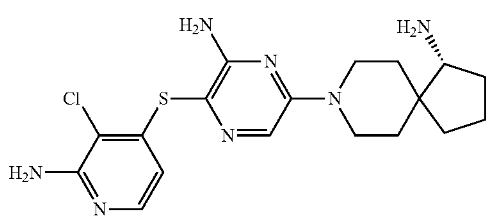 [SMILES: Nc1nc(N2CCC3(CCC[C@H]3N)CC2)cnc1Sc1ccnc(N)c1Cl] | (R)-8-(6-amino-5-((2-amino-3-chloropyridin-4-yl)thio)pyrazin-2-yl)-8-azaspiro[4.5]decan-1-amine |
| 7 | 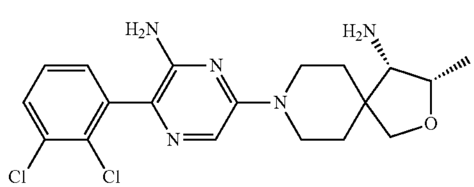 [SMILES: C[C@@H]1OCC2(CCN(c3cnc(-c4cccc(Cl)c4Cl)c(N)n3)CC2)[C@@H]1N] | (3S,4S)-8-(6-amino-5-(2,3-dichlorophenyl)pyrazin-2-yl)-3-methyl-2-oxa-8-azaspiro[4.5]decan-4-amine |
| 8 | 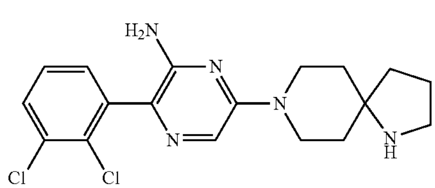 [SMILES: Nc1nc(N2CCC3(CCCN3)CC2)cnc1-c1cccc(Cl)c1Cl] | 3-(2,3-dichlorophenyl)-6-(1,8-diazaspiro[4.5]decan-8-yl)pyrazin-2-amine |

TABLE 1-continued

| Compound No. | Structure | Name |
|---|---|---|
| 9 | 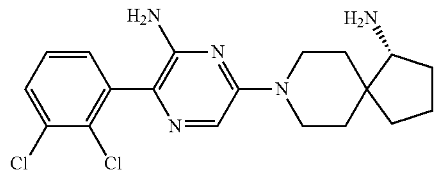 [SMILES: Nc1nc(N2CCC3(CCC[C@H]3N)CC2)cnc1-c1cccc(Cl)c1Cl] | (R)-8-(6-amino-5-(2,3-dichlorophenyl)pyrazin-2-yl)-8-azaspiro[4.5]decan-1-amine |
| 10 | 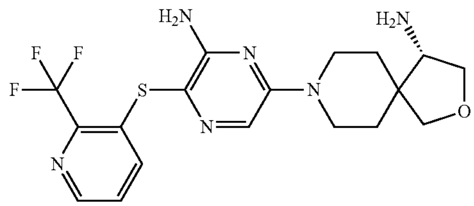 [SMILES: Nc1nc(N2CCC3(CC2)COC[C@H]3N)cnc1Sc1cccnc1C(F)(F)F] | (S)-8-(6-amino-5-((2-(trifluoromethyl)pyridin-3-yl)thio)pyrazin-2-yl)-2-oxa-8-azaspiro[4.5]decan-4-amine |
| 11 | 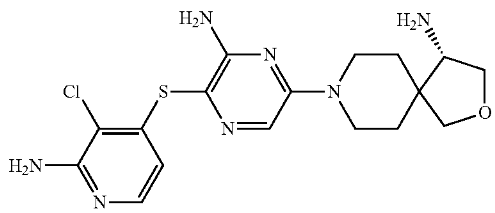 [SMILES: Nc1nc(N2CCC3(CC2)COC[C@H]3N)cnc1Sc1ccnc(N)c1Cl] | (S)-8-(6-amino-5-((2-amino-3-chloropyridin-4-yl)thio)pyrazin-2-yl)-2-oxa-8-azaspiro[4.5]decan-4-amine |
| 12 | 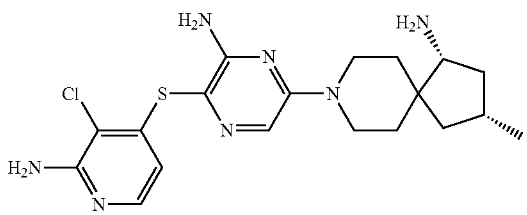 [SMILES: C[C@H]1C[C@@H](N)C2(CCN(c3cnc(Sc4ccnc(N)c4Cl)c(N)n3)CC2)C1] | (1R,3R)-8-(6-amino-5-((2-amino-3-chloropyridin-4-yl)thio)pyrazin-2-yl)-3-methyl-8-azaspiro[4.5]decan-1-amine |
| 13 | 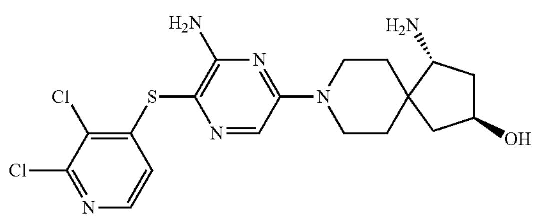 [SMILES: Nc1nc(N2CCC3(CC2)C[C@H](O)C[C@H]3N)cnc1Sc1ccnc(Cl)c1Cl] | (2S,4R)-4-amino-8-(6-amino-5-((2,3-dichloropyridin-4-yl)thio)pyrazin-2-yl)-8-azaspiro[4.5]decan-2-ol |
| 14 | 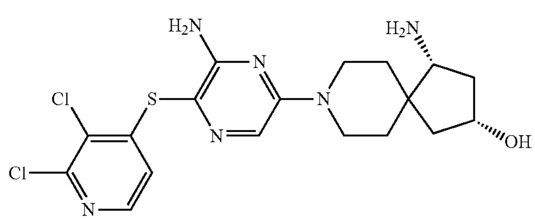 [SMILES: Nc1nc(N2CCC3(CC2)C[C@@H](O)C[C@H]3N)cnc1Sc1ccnc(Cl)c1Cl] | (2R,4R)-4-amino-8-(6-amino-5-((2,3-dichloropyridin-4-yl)thio)pyrazin-2-yl)-8-azaspiro[4.5]decan-2-ol |
| 15 | 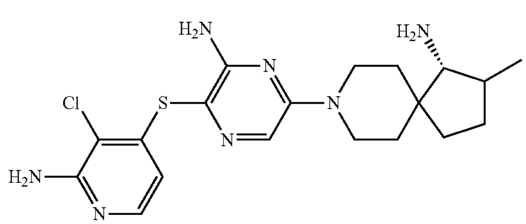 [SMILES: CC1CCC2(CCN(c3cnc(Sc4ccnc(N)c4Cl)c(N)n3)CC2)[C@@H]1N] | (1R)-8-(6-amino-5-((2-amino-3-chloropyridin-4-yl)thio)pyrazin-2-yl)-2-methyl-8-azaspiro[4.5]decan-1-amine |

TABLE 1-continued

| Compound No. | Structure | Name |
|---|---|---|
| 16 | 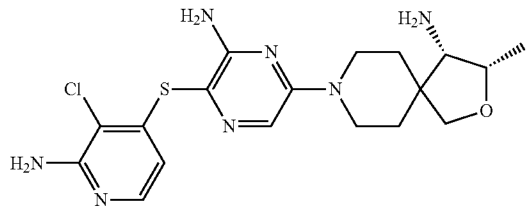 [SMILES: C[C@@H]1OCC2(CCN(c3cnc(Sc4ccnc(N)c4Cl)c(N)n3)CC2)[C@@H]1N] | (3S,4S)-8-(6-amino-5-((2-amino-3-chloropyridin-4-yl)thio)pyrazin-2-yl)-3-methyl-2-oxa-8-azaspiro[4.5]decan-4-amine |
| 17 | 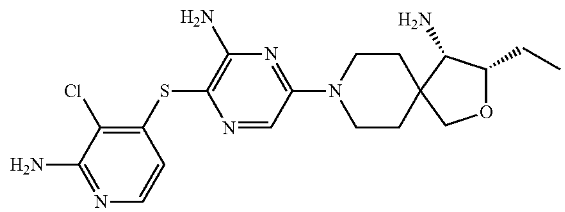 [SMILES: CC[C@@H]1OCC2(CCN(c3cnc(Sc4ccnc(N)c4Cl)c(N)n3)CC2)[C@@H]1N] | (3S,4S)-8-(6-amino-5-((2-amino-3-chloropyridin-4-yl)thio)pyrazin-2-yl)-3-ethyl-2-oxa-8-azaspiro[4.5]decan-4-amine |
| 18 | 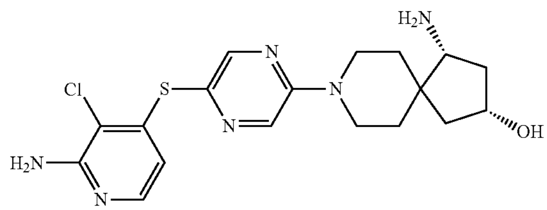 [SMILES: Nc1nccc(Sc2cnc(N3CCC4(CC3)C[C@@H](O)C[C@H]4N)cn2)c1Cl] | (2R,4R)-4-amino-8-(5-((2-amino-3-chloropyridin-4-yl)thio)pyrazin-2-yl)-8-azaspiro[4.5]decan-2-ol |
| 19 | 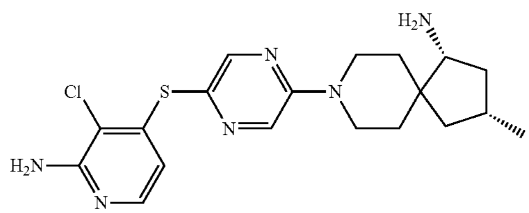 [SMILES: C[C@H]1C[C@@H](N)C2(CCN(c3cnc(Sc4ccnc(N)c4Cl)cn3)CC2)C1] | (1R,3R)-8-(5-((2-amino-3-chloropyridin-4-yl)thio)pyrazin-2-yl)-3-methyl-8-azaspiro[4.5]decan-1-amine |
| 20 | 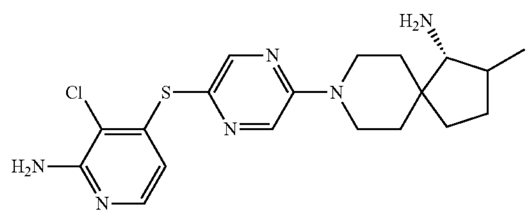 [SMILES: CC1CCC2(CCN(c3cnc(Sc4ccnc(N)c4Cl)cn3)CC2)[C@@H]1N] | (1R)-8-(5-((2-amino-3-chloropyridin-4-yl)thio)pyrazin-2-yl)-2-methyl-8-azaspiro[4.5]decan-1-amine |
| 21 | 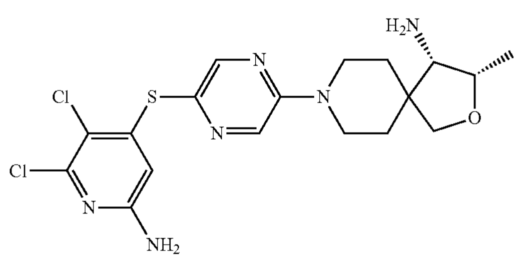 [SMILES: C[C@@H]1OCC2(CCN(c3cnc(Sc4cc(N)nc(Cl)c4Cl)cn3)CC2)[C@@H]1N] | (3S,4S)-8-(5-((6-amino-2,3-dichloropyridin-4-yl)thio)pyrazin-2-yl)-3-methyl-2-oxa-8-azaspiro[4.5]decan-4-amine |
| 22 | 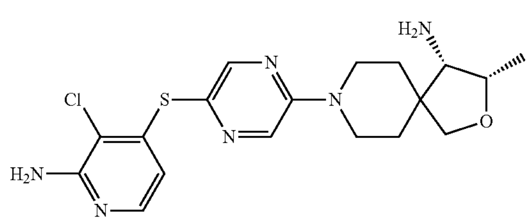 [SMILES: C[C@@H]1OCC2(CCN(c3cnc(Sc4ccnc(N)c4Cl)cn3)CC2)[C@@H]1N] | (3S,4S)-8-(5-((2-amino-3-chloropyridin-4-yl)thio)pyrazin-2-yl)-3-methyl-2-oxa-8-azaspiro[4.5]decan-4-amine |

TABLE 1-continued

| Compound No. | Structure | Name |
|---|---|---|
| 23 | 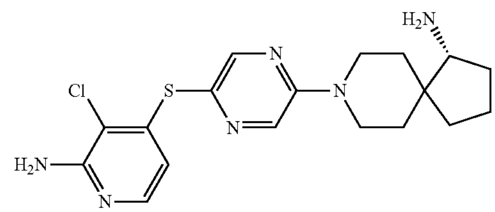 [SMILES: Nc1nccc(Sc2cnc(N3CCC4(CCC[C@H]4N)CC3)cn2)c1Cl] | (R)-8-(5-((2-amino-3-chloropyridin-4-yl)thio)pyrazin-2-yl)-8-azaspiro[4.5]decan-1-amine |
| 24 | 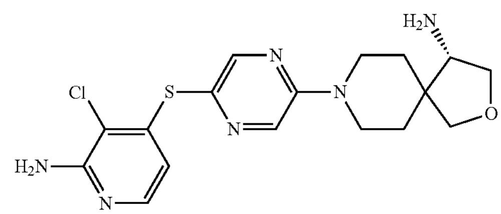 [SMILES: Nc1nccc(Sc2cnc(N3CCC4(CC3)COC[C@H]4N)cn2)c1Cl] | (S)-8-(5-((2-amino-3-chloropyridin-4-yl)thio)pyrazin-2-yl)-2-oxa-8-azaspiro[4.5]decan-4-amine |
| 25 | 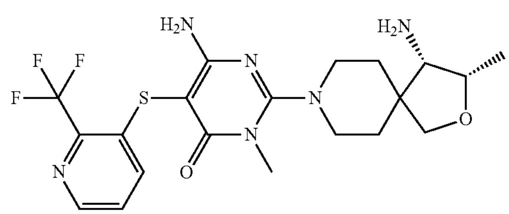 [SMILES: C[C@@H]1OCC2(CCN(c3nc(N)c(Sc4cccnc4C(F)(F)F)c(=O)n3C)CC2)[C@@H]1N] | 6-amino-2-((3S,4S)-4-amino-3-methyl-2-oxa-8-azaspiro[4.5]decan-8-yl)-3-methyl-5-((2-(trifluoromethyl)pyridin-3-yl)thio)pyrimidin-4(3H)-one |
| 26 | 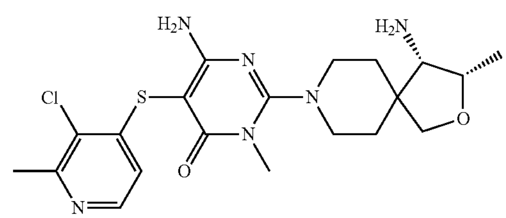 | 6-amino-2-((3S,4S)-4-amino-3-methyl-2-oxa-8-azaspiro[4.5]decan-8-yl)-5-((3-chloro-2-methylpyridin-4-yl)thio)-3-methylpyrimidin-4(3H)-one |
| 27 | 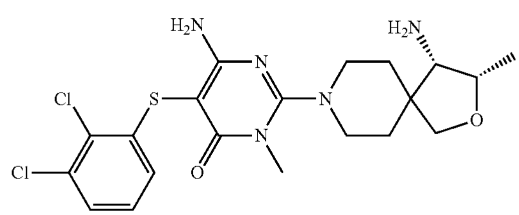 [SMILES: C[C@@H]1OCC2(CCN(c3nc(N)c(Sc4cccc(Cl)c4Cl)c(=O)n3C)CC2)[C@@H]1N] | 6-amino-2-((3S,4S)-4-amino-3-methyl-2-oxa-8-azaspiro[4.5]decan-8-yl)-5-((2,3-dichlorophenyl)thio)-3-methylpyrimidin-4(3H)-one |
| 28 | 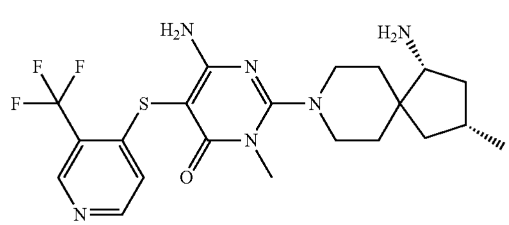 [SMILES: C[C@H]1C[C@@H](N)C2(CCN(c3nc(N)c(Sc4ccncc4C(F)(F)F)c(=O)n3C)CC2)C1] | 6-amino-2-((1R,3R)-1-amino-3-methyl-8-azaspiro[4.5]decan-8-yl)-3-methyl-5-((3-(trifluoromethyl)pyridin-4-yl)thio)pyrimidin-4(3H)-one |
| 29 | 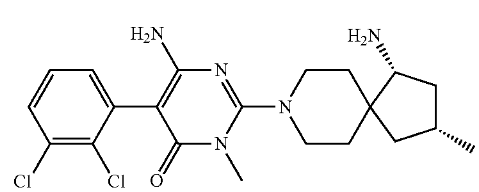 [SMILES: C[C@H]1C[C@@H](N)C2(CCN(c3nc(N)c(-c4cccc(Cl)c4Cl)c(=O)n3C)CC2)C1] | 6-amino-2-((1R,3R)-1-amino-3-methyl-8-azaspiro[4.5]decan-8-yl)-5-(2,3-dichlorophenyl)-3-methylpyrimidin-4(3H)-one |

TABLE 1-continued

| Compound No. | Structure | Name |
|---|---|---|
| 30 | 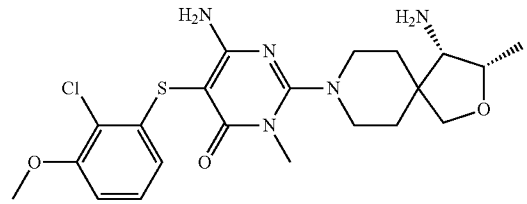 | 6-amino-2-((3S,4S)-4-amino-3-methyl-2-oxa-8-azaspiro[4.5]decan-8-yl)-5-((2-chloro-3-methoxyphenyl)thio)-3-methylpyrimidin-4(3H)-one |
| 31 | 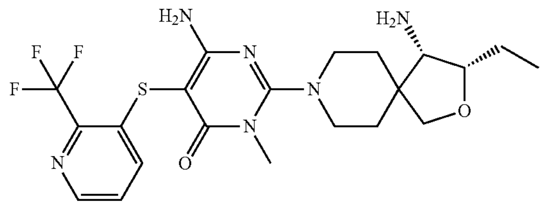 [SMILES: CC[C@@H]1OCC2(CCN(c3nc(N)c(Sc4cccnc4C(F)(F)F)c(=O)n3C)CC2)[C@@H]1N] | 6-amino-2-((3S,4S)-4-amino-3-ethyl-2-oxa-8-azaspiro[4.5]decan-8-yl)-3-methyl-5-((2-(trifluoromethyl)pyridin-3-yl)thio)pyrimidin-4(3H)-one |
| 32 | 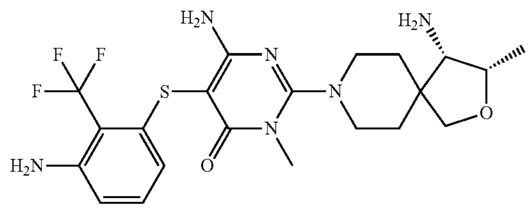 [SMILES: C[C@@H]1OCC2(CCN(c3nc(N)c(Sc4cccc(N)c4C(F)(F)F)c(=O)n3C)CC2)[C@@H]1N] | 6-amino-5-((3-amino-2-(trifluoromethyl)phenyl)thio)-2-((3S,4S)-4-amino-3-methyl-2-oxa-8-azaspiro[4.5]decan-8-yl)-3-methylpyrimidin-4(3H)-one |
| 33 | 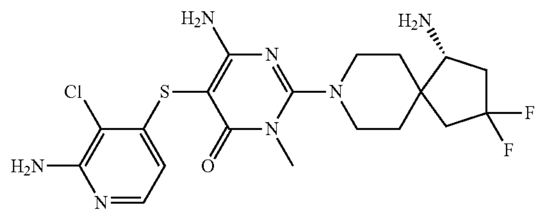 [SMILES: Cn1c(N2CCC3(CC2)CC(F)(F)C[C@H]3N)nc(N)c(Sc2ccnc(N)c2Cl)c1=O] | (R)-6-amino-2-(1-amino-3,3-difluoro-8-azaspiro[4.5]decan-8-yl)-5-((2-amino-3-chloropyridin-4-yl)thio)-3-methylpyrimidin-4(3H)-one |
| 34 | 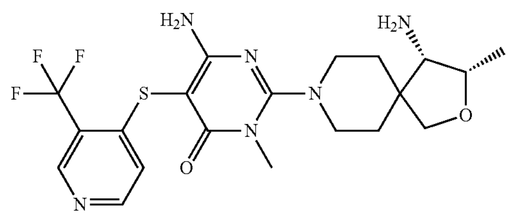 [SMILES: C[C@@H]1OCC2(CCN(c3nc(N)c(Sc4ccncc4C(F)(F)F)c(=O)n3C)CC2)[C@@H]1N] | 6-amino-2-((3S,4S)-4-amino-3-methyl-2-oxa-8-azaspiro[4.5]decan-8-yl)-3-methyl-5-((3-(trifluoromethyl)pyridin-4-yl)thio)pyrimidin-4(3H)-one |
| 35 | 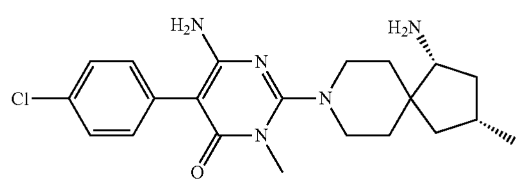 [SMILES: C[C@H]1C[C@@H](N)C2(CCN(c3nc(N)c(-c4ccc(Cl)cc4)c(=O)n3C)CC2)C1] | 6-amino-2-((1R,3R)-1-amino-3-methyl-8-azaspiro[4.5]decan-8-yl)-5-(4-chlorophenyl)-3-methylpyrimidin-4(3H)-one |
| 36 | 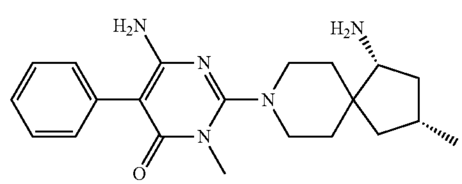 [SMILES: C[C@H]1C[C@@H](N)C2(CCN(c3nc(N)c(-c4ccccc4)c(=O)n3C)CC2)C1] | 6-amino-2-((1R,3R)-1-amino-3-methyl-8-azaspiro[4.5]decan-8-yl)-3-methyl-5-phenylpyrimidin-4(3H)-one |

TABLE 1-continued

| Compound No. | Name |
|---|---|
| 37 | (R)-6-(1-amino-8-azaspiro[4.5]decan-8-yl)-3-(2,3-dichlorophenyl)-5-methyl-2,5-dihydro-4H-pyrazolo[3,4-d]pyrimidin-4-one |
| 38 | 2-(4-(aminomethyl)-4-methylpiperidin-1-yl)-5-(2,3-dichlorophenyl)-3,7-dihydro-4H-pyrrolo[2,3-d]pyrimidin-4-one |
| 39 | (3S,4S)-8-(3-(2,3-dichloropyridin-4-yl)-1H-pyrazolo[3,4-b]pyrazin-6-yl)-3-methyl-2-oxa-8-azaspiro[4.5]decan-4-amine |
| 40 | 3-(6-amino-2-methylpyridin-3-yl)-6-((1R,3R)-1-amino-3-methyl-8-azaspiro[4.5]decan-8-yl)-5-methyl-2,5-dihydro-4H-pyrazolo[3,4-d]pyrimidin-4-one |
| 41 | (R)-3-(6-amino-2-methylpyridin-3-yl)-6-(1-amino-3,3-difluoro-8-azaspiro[4.5]decan-8-yl)-5-methyl-2,5-dihydro-4H-pyrazolo[3,4-d]pyrimidin-4-one |
| 42 | 6-((3S,4S)-4-amino-3-methyl-2-oxa-8-azaspiro[4.5]decan-8-yl)-3-(3-chloro-2-(cyclopropylamino)pyridin-4-yl)-5-methyl-2,5-dihydro-4H-pyrazolo[3,4-d]pyrimidin-4-one |
| 43 | 2-((3S,4S)-4-amino-3-methyl-2-oxa-8-azaspiro[4.5]decan-8-yl)-5-(3-chloro-2-methoxypyridin-4-yl)-3-methyl-3,7-dihydro-4H-pyrrolo[2,3-d]pyrimidin-4-one |

TABLE 1-continued

| Compound No. | Structure | Name |
|---|---|---|
| 44 | 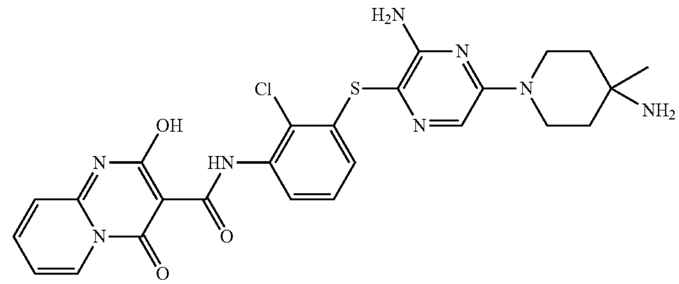 [SMILES: CC1(N)CCN(c2cnc(Sc3cccc(NC(=O)c4c(O)nc5ccccn5c4=O)c3Cl)c(N)n2)CC1] | N-(3-((3-amino-5-(4-amino-4-methylpiperidin-1-yl)pyrazin-2-yl)thio)-2-chlorophenyl)-2-hydroxy-4-oxo-4H-pyrido[1,2-a]pyrimidine-3-carboxamide |
| 45 | 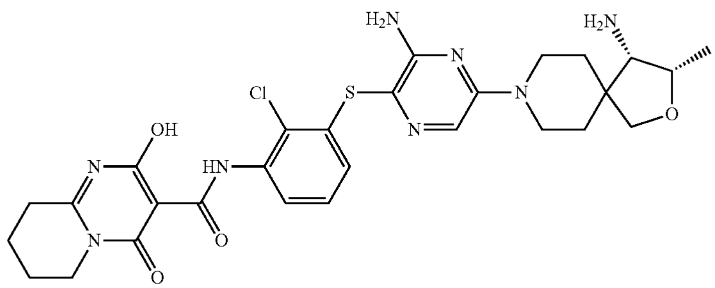 [SMILES: C[C@@H]1OCC2(CCN(c3cnc(Sc4cccc(NC(=O)c5c(O)nc6n(c5=O)CCCC6)c4Cl)c(N)n3)CC2)[C@@H]1N] | N-(3-((3-amino-5-((3S,4S)-4-amino-3-methyl-2-oxa-8-azaspiro[4.5]decan-8-yl)pyrazin-2-yl)thio)-2-chlorophenyl)-2-hydroxy-4-oxo-6,7,8,9-tetrahydro-4H-pyrido[1,2-a]pyrimidine-3-carboxamide |
| 46 | 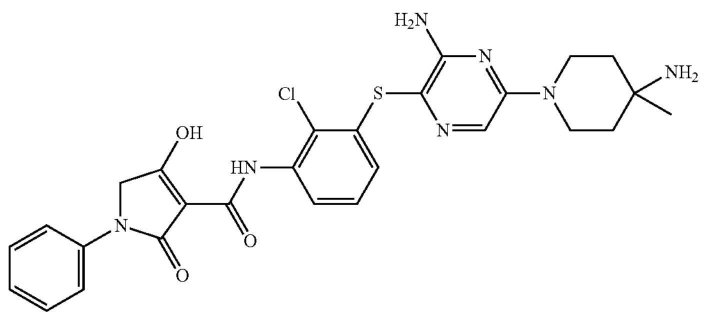 [SMILES: CC1(N)CCN(c2cnc(Sc3cccc(NC(=O)C4=C(O)CN(c5ccccc5)C4=O)c3Cl)c(N)n2)CC1] | N-(3-((3-amino-5-(4-amino-4-methylpiperidin-1-yl)pyrazin-2-yl)thio)-2-chlorophenyl)-4-hydroxy-2-oxo-1-phenyl-2,5-dihydro-1H-pyrrole-3-carboxamide |
| 47 | 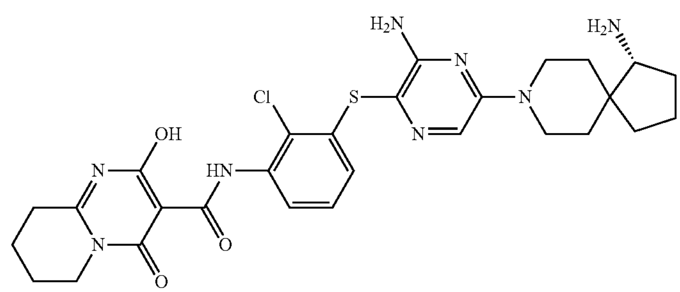 [SMILES: Nc1nc(N2CCC3(CCC[C@H]3N)CC2)cnc1Sc1cccc(NC(=O)c2c(O)nc3n(c2=O)CCCC3)c1Cl] | (R)-N-(3-((3-amino-5-(1-amino-8-azaspiro[4.5]decan-8-yl)pyrazin-2-yl)thio)-2-chlorophenyl)-2-hydroxy-4-oxo-6,7,8,9-tetrahydro-4H-pyrido[1,2-a]pyrimidine-3-carboxamide |
| 48 | 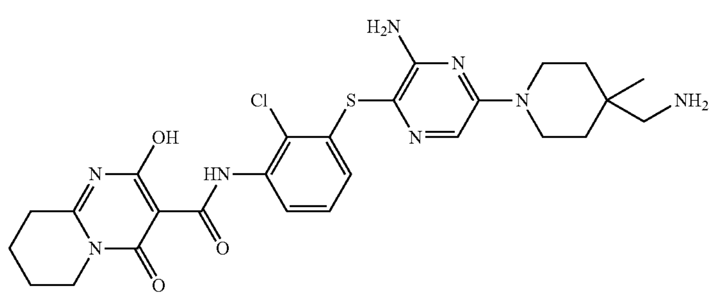 [SMILES: CC1(CN)CCN(c2cnc(Sc3cccc(NC(=O)c4c(O)nc5n(c4=O)CCCC5)c3Cl)c(N)n2)CC1] | N-(3-((3-amino-5-(4-(aminomethyl)-4-methylpiperidin-1-yl)pyrazin-2-yl)thio)-2-chlorophenyl)-2-hydroxy-4-oxo-6,7,8,9-tetrahydro-4H-pyrido[1,2-a]pyrimidine-3-carboxamide |

TABLE 1-continued

| Compound No. | Structure | Name |
|---|---|---|
| 49 | 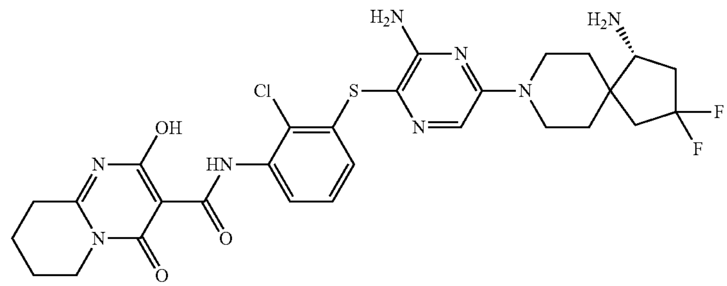 [SMILES: Nc1nc(N2CCC3(CC2)CC(F)(F)C[C@H]3N)cnc1Sc1cccc(NC(=O)c2c(O)nc3n(c2=O)CCCC3)c1Cl] | (R)-N-(3-((3-amino-5-(1-amino-3,3-difluoro-8-azaspiro[4.5]decan-8-yl)pyrazin-2-yl)thio)-2-chlorophenyl)-2-hydroxy-4-oxo-6,7,8,9-tetrahydro-4H-pyrido[1,2-a]pyrimidine-3-carboxamide |
| 50 | 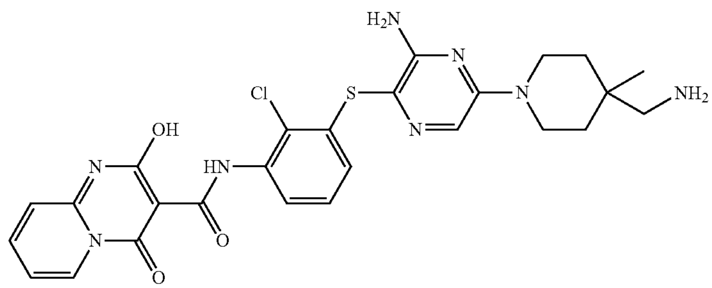 [SMILES: CC1(CN)CCN(c2cnc(Sc3cccc(NC(=O)c4c(O)nc5ccccn5c4=O)c3Cl)c(N)n2)CC1] | N-(3-((3-amino-5-(4-(aminomethyl)-4-methylpiperidin-1-yl)pyrazin-2-yl)thio)-2-chlorophenyl)-2-hydroxy-4-oxo-4H-pyrido[1,2-a]pyrimidine-3-carboxamide |
| 51 | 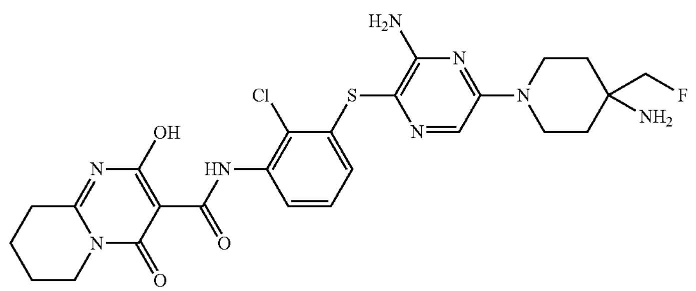 | N-(3-((3-amino-5-(4-amino-4-(fluoromethyl)piperidin-1-yl)pyrazin-2-yl)thio)-2-chlorophenyl)-2-hydroxy-4-oxo-6,7,8,9-tetrahydro-4H-pyrido[1,2-a]pyrimidine-3-carboxamide |
| 52 | 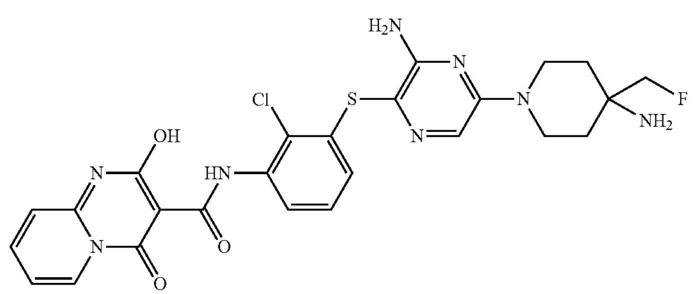 [SMILES: Nc1nc(N2CCC(N)(CF)CC2)cnc1Sc1cccc(NC(=O)c2c(O)nc3ccccn3c2=O)c1Cl] | N-(3-((3-amino-5-(4-amino-4-(fluoromethyl)piperidin-1-yl)pyrazin-2-yl)thio)-2-chlorophenyl)-2-hydroxy-4-oxo-4H-pyrido[1,2-a]pyrimidine-3-carboxamide |
| 53 | 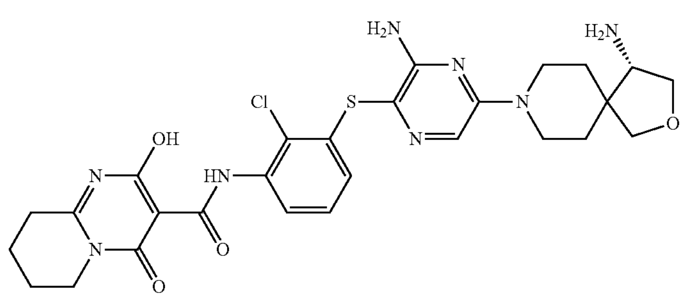 [SMILES: Nc1nc(N2CCC3(CC2)COC[C@H]3N)cnc1Sc1cccc(NC(=O)c2c(O)nc3n(c2=O)CCCC3)c1Cl] | (S)-N-(3-((3-amino-5-(4-amino-2-oxa-8-azaspiro[4.5]decan-8-yl)pyrazin-2-yl)thio)-2-chlorophenyl)-2-hydroxy-4-oxo-6,7,8,9-tetrahydro-4H-pyrido[1,2-a]pyrimidine-3-carboxamide |

TABLE 1-continued

| Compound No. | Structure | Name |
|---|---|---|
| 54 | 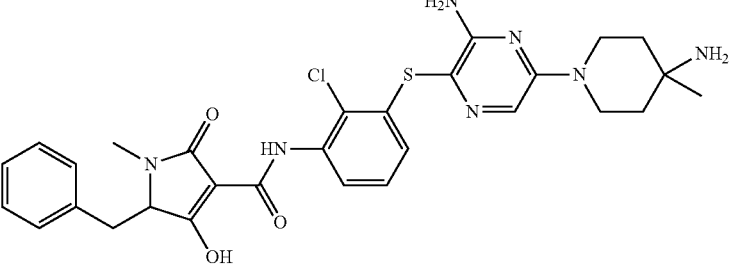 | N-(3-((3-amino-5-(4-amino-4-methylpiperidin-1-yl)pyrazin-2-yl)thio)-2-chlorophenyl)-5-benzyl-4-hydroxy-1-methyl-2-oxo-2,5-dihydro-1H-pyrrole-3-carboxamide |

Embodiment 3. The pharmaceutical combination of Embodiment 1 or Embodiment 2, wherein the ALK inhibitor is 5-chloro-N2-[2-isopropoxy-5-methyl-4-(4-piperidinyl) phenyl]-N4-[2-(isopropylsulfonyl)phenyl]-2,4-pyrimidinediamine (ceritinib), or a pharmaceutically acceptable salt thereof.

Embodiment 4. A pharmaceutical combination comprising:
(i) 5-chloro-N2-[2-isopropoxy-5-methyl-4-(4-piperidinyl)phenyl]-N4-[2-(isopropylsulfonyl)phenyl]-2,4-pyrimidinediamine (ceritinib), or a pharmaceutically acceptable salt thereof, and
(ii) a SHP2 inhibitor of Table 1, or a pharmaceutically acceptable salt thereof.

Embodiment 5. The pharmaceutical combination of any one of Embodiments 1 to 4, wherein the SHP2 inhibitor is 6-(4-amino-4-methylpiperidin-1-yl)-3-(2,3-dichlorophenyl)pyrazin-2-amine.

Embodiment 6. The pharmaceutical combination of any one of Embodiments 1 to 4, wherein the SHP2 inhibitor is 6-(4-(aminomethyl)-4-phenylpiperidin-1-yl)-3-(2,3-dichlorophenyl)pyrazin-2-amine.

Embodiment 7. The pharmaceutical combination of any one of Embodiments 1 to 4, wherein the SHP2 inhibitor is 6-(4-(aminomethyl)-4-methylpiperidin-1-yl)-3-(2,3-dichlorophenyl)pyrazin-2-amine.

Embodiment 8. The pharmaceutical combination of any one of Embodiments 1 to 4, wherein the SHP2 inhibitor is 6-(4-(aminomethyl)-4-methylpiperidin-1-yl)-3-((2-(trifluoromethyl)pyridin-3-yl)thio)pyrazin-2-amine.

Embodiment 9. The pharmaceutical combination of any one of Embodiments 1 to 4, wherein the SHP2 inhibitor is (R)-8-(6-amino-5-((2-(trifluoromethyl)pyridin-3-yl)thio)pyrazin-2-yl)-8-azaspiro[4.5]decan-1-amine.

Embodiment 10. The pharmaceutical combination of any one of Embodiments 1 to 4, wherein the SHP2 inhibitor is (R)-8-(6-amino-5-((2-amino-3-chloropyridin-4-yl)thio)pyrazin-2-yl)-8-azaspiro[4.5]decan-1-amine.

Embodiment 11. The pharmaceutical combination of any one of Embodiments 1 to 4, wherein the SHP2 inhibitor is (3S,4S)-8-(6-amino-5-(2,3-dichlorophenyl)pyrazin-2-yl)-3-methyl-2-oxa-8-azaspiro[4.5]decan-4-amine.

Embodiment 12. The pharmaceutical combination of any one of Embodiments 1 to 4, wherein the SHP2 inhibitor is 3-(2,3-dichlorophenyl)-6-(1,8-diazaspiro[4.5]decan-8-yl) pyrazin-2-amine.

Embodiment 13. The pharmaceutical combination of any one of Embodiments 1 to 4, wherein the SHP2 inhibitor is (R)-8-(6-amino-5-(2,3-dichlorophenyl)pyrazin-2-yl)-8-azaspiro[4.5]decan-1-amine.

Embodiment 14. The pharmaceutical combination of any one of Embodiments 1 to 4, wherein the SHP2 inhibitor is (S)-8-(6-amino-5-((2-(trifluoromethyl)pyridin-3-yl)thio) pyrazin-2-yl)-2-oxa-8-azaspiro[4.5]decan-4-amine.

Embodiment 15. The pharmaceutical combination of any one of Embodiments 1 to 4, wherein the SHP2 inhibitor is (S)-8-(6-amino-5-((2-amino-3-chloropyridin-4-yl)thio) pyrazin-2-yl)-2-oxa-8-azaspiro[4.5]decan-4-amine.

Embodiment 16. The pharmaceutical combination of any one of Embodiments 1 to 4, wherein the SHP2 inhibitor is (1R,3R)-8-(6-amino-5-((2-amino-3-chloropyridin-4-yl) thio)pyrazin-2-yl)-3-methyl-8-azaspiro[4.5]decan-1-amine.

Embodiment 17. The pharmaceutical combination of any one of Embodiments 1 to 4, wherein the SHP2 inhibitor is (2S,4R)-4-amino-8-(6-amino-5-((2,3-dichloropyridin-4-yl) thio)pyrazin-2-yl)-8-azaspiro[4.5]decan-2-ol.

Embodiment 18. The pharmaceutical combination of any one of Embodiments 1 to 4, wherein the SHP2 inhibitor is (2R,4R)-4-amino-8-(6-amino-5-((2,3-dichloropyridin-4-yl) thio)pyrazin-2-yl)-8-azaspiro[4.5]decan-2-ol.

Embodiment 19. The pharmaceutical combination of any one of Embodiments 1 to 4, wherein the SHP2 inhibitor is (1R)-8-(6-amino-5-((2-amino-3-chloropyridin-4-yl)thio) pyrazin-2-yl)-2-methyl-8-azaspiro[4.5]decan-1-amine.

Embodiment 20. The pharmaceutical combination of any one of Embodiments 1 to 4, wherein the SHP2 inhibitor is (3S,4S)-8-(6-amino-5-((2-amino-3-chloropyridin-4-yl)thio) pyrazin-2-yl)-3-methyl-2-oxa-8-azaspiro[4.5]decan-4-amine.

Embodiment 21. The pharmaceutical combination of any one of Embodiments 1 to 4, wherein the SHP2 inhibitor is (3S,4S)-8-(6-amino-5-((2-amino-3-chloropyridin-4-yl)thio) pyrazin-2-yl)-3-ethyl-2-oxa-8-azaspiro[4.5]decan-4-amine.

Embodiment 22. The pharmaceutical combination of any one of Embodiments 1 to 4, wherein the SHP2 inhibitor is (2R,4R)-4-amino-8-(5-((2-amino-3-chloropyridin-4-yl) thio)pyrazin-2-yl)-8-azaspiro[4.5]decan-2-ol.

Embodiment 23. The pharmaceutical combination of any one of Embodiments 1 to 4, wherein the SHP2 inhibitor is (1R,3R)-8-(5-((2-amino-3-chloropyridin-4-yl)thio)pyrazin-2-yl)-3-methyl-8-azaspiro[4.5]decan-1-amine.

Embodiment 24. The pharmaceutical combination of any one of Embodiments 1 to 4, wherein the SHP2 inhibitor is (1R)-8-(5-((2-amino-3-chloropyridin-4-yl)thio)pyrazin-2-yl)-2-methyl-8-azaspiro[4.5]decan-1-amine.

Embodiment 25. The pharmaceutical combination of any one of Embodiments 1 to 4, wherein the SHP2 inhibitor is (3S,4S)-8-(5-((6-amino-2,3-dichloropyridin-4-yl)thio) pyrazin-2-yl)-3-methyl-2-oxa-8-azaspiro[4.5]decan-4-amine.

Embodiment 26. The pharmaceutical combination of any one of Embodiments 1 to 4, wherein the SHP2 inhibitor is (3S,4S)-8-(5-((2-amino-3-chloropyridin-4-yl)thio)pyrazin-2-yl)-3-methyl-2-oxa-8-azaspiro[4.5]decan-4-amine.

Embodiment 27. The pharmaceutical combination of any one of Embodiments 1 to 4, wherein the SHP2 inhibitor is (R)-8-(5-((2-amino-3-chloropyridin-4-yl)thio)pyrazin-2-yl)-8-azaspiro[4.5]decan-1-amine.

Embodiment 28. The pharmaceutical combination of any one of Embodiments 1 to 4, wherein the SHP2 inhibitor is (S)-8-(5-((2-amino-3-chloropyridin-4-yl)thio)pyrazin-2-yl)-2-oxa-8-azaspiro[4.5]decan-4-amine.

Embodiment 29. The pharmaceutical combination of any one of Embodiments 1 to 4, wherein the SHP2 inhibitor is 6-amino-2-((3S,4S)-4-amino-3-methyl-2-oxa-8-azaspiro[4.5]decan-8-yl)-3-methyl-5-((2-(trifluoromethyl)pyridin-3-yl)thio)pyrimidin-4(3H)-one.

Embodiment 30. The pharmaceutical combination of any one of Embodiments 1 to 4, wherein the SHP2 inhibitor is 6-amino-2-((3S,4S)-4-amino-3-methyl-2-oxa-8-azaspiro[4.5]decan-8-yl)-5-((3-chloro-2-methylpyridin-4-yl)thio)-3-methylpyrimidin-4(3H)-one.

Embodiment 31. The pharmaceutical combination of any one of Embodiments 1 to 4, wherein the SHP2 inhibitor is 6-amino-2-((3S,4S)-4-amino-3-methyl-2-oxa-8-azaspiro[4.5]decan-8-yl)-5-((2,3-dichlorophenyl)thio)-3-methylpyrimidin-4(3H)-one.

Embodiment 32. The pharmaceutical combination of any one of Embodiments 1 to 4, wherein the SHP2 inhibitor is 6-amino-2-((1R,3R)-1-amino-3-methyl-8-azaspiro[4.5]decan-8-yl)-3-methyl-5-((3-(trifluoromethyl)pyridin-4-yl)thio)pyrimidin-4(3H)-one.

Embodiment 33. The pharmaceutical combination of any one of Embodiments 1 to 4, wherein the SHP2 inhibitor is 6-amino-2-((1R,3R)-1-amino-3-methyl-8-azaspiro[4.5]decan-8-yl)-5-(2,3-dichlorophenyl)-3-methylpyrimidin-4(3H)-one.

Embodiment 34. The pharmaceutical combination of any one of Embodiments 1 to 4, wherein the SHP2 inhibitor is 6-amino-2-((3S,4S)-4-amino-3-methyl-2-oxa-8-azaspiro[4.5]decan-8-yl)-5-((2-chloro-3-methoxyphenyl)thio)-3-methylpyrimidin-4(3H)-one.

Embodiment 35. The pharmaceutical combination of any one of Embodiments 1 to 4, wherein the SHP2 inhibitor is 6-amino-2-((3S,4S)-4-amino-3-ethyl-2-oxa-8-azaspiro[4.5]decan-8-yl)-3-methyl-5-((2-(trifluoromethyl)pyridin-3-yl)thio)pyrimidin-4(3H)-one.

Embodiment 36. The pharmaceutical combination of any one of Embodiments 1 to 4, wherein the SHP2 inhibitor is 6-amino-5-((3-amino-2-(trifluoromethyl)phenyl)thio)-2-((3S,4S)-4-amino-3-methyl-2-oxa-8-azaspiro[4.5]decan-8-yl)-3-methylpyrimidin-4(3H)-one.

Embodiment 37. The pharmaceutical combination of any one of Embodiments 1 to 4, wherein the SHP2 inhibitor is (R)-6-amino-2-(1-amino-3,3-difluoro-8-azaspiro[4.5]decan-8-yl)-5-((2-amino-3-chloropyridin-4-yl)thio)-3-methylpyrimidin-4(3H)-one.

Embodiment 38. The pharmaceutical combination of any one of Embodiments 1 to 4, wherein the SHP2 inhibitor is 6-amino-2-((3S,4S)-4-amino-3-methyl-2-oxa-8-azaspiro[4.5]decan-8-yl)-3-methyl-5-((3-(trifluoromethyl)pyridin-4-yl)thio)pyrimidin-4(3H)-one.

Embodiment 39. The pharmaceutical combination of any one of Embodiments 1 to 4, wherein the SHP2 inhibitor is 6-amino-2-((1R,3R)-1-amino-3-methyl-8-azaspiro[4.5]decan-8-yl)-5-(4-chlorophenyl)-3-methylpyrimidin-4(3H)-one.

Embodiment 40. The pharmaceutical combination of any one of Embodiments 1 to 4, wherein the SHP2 inhibitor is 6-amino-2-((1R,3R)-1-amino-3-methyl-8-azaspiro[4.5]decan-8-yl)-3-methyl-5-phenylpyrimidin-4(3H)-one.

Embodiment 41. The pharmaceutical combination of any one of Embodiments 1 to 4, wherein the SHP2 inhibitor is (R)-6-(1-amino-8-azaspiro[4.5]decan-8-yl)-3-(2,3-dichlorophenyl)-5-methyl-2,5-dihydro-4H-pyrazolo[3,4-d]pyrimidin-4-one.

Embodiment 42. The pharmaceutical combination of any one of Embodiments 1 to 4, wherein the SHP2 inhibitor is 2-(4-(aminomethyl)-4-methylpiperidin-1-yl)-5-(2,3-dichlorophenyl)-3,7-dihydro-4H-pyrrolo[2,3-d]pyrimidin-4-one.

Embodiment 43. The pharmaceutical combination of any one of Embodiments 1 to 4, wherein the SHP2 inhibitor is (3S,4S)-8-(3-(2,3-dichloropyridin-4-yl)-1H-pyrazolo[3,4-b]pyrazin-6-yl)-3-methyl-2-oxa-8-azaspiro[4.5]decan-4-amine.

Embodiment 44. The pharmaceutical combination of any one of Embodiments 1 to 4, wherein the SHP2 inhibitor is 3-(6-amino-2-methylpyridin-3-yl)-6-((1R,3R)-1-amino-3-methyl-8-azaspiro[4.5]decan-8-yl)-5-methyl-2,5-dihydro-4H-pyrazolo[3,4-d]pyrimidin-4-one.

Embodiment 45. The pharmaceutical combination of any one of Embodiments 1 to 4, wherein the SHP2 inhibitor is (R)-3-(6-amino-2-methylpyridin-3-yl)-6-(1-amino-3,3-difluoro-8-azaspiro[4.5]decan-8-yl)-5-methyl-2,5-dihydro-4H-pyrazolo[3,4-d]pyrimidin-4-one.

Embodiment 46. The pharmaceutical combination of any one of Embodiments 1 to 4, wherein the SHP2 inhibitor is 6-((3S,4S)-4-amino-3-methyl-2-oxa-8-azaspiro[4.5]decan-8-yl)-3-(3-chloro-2-(cyclopropylamino)pyridin-4-yl)-5-methyl-2,5-dihydro-4H-pyrazolo[3,4-d]pyrimidin-4-one.

Embodiment 47. The pharmaceutical combination of any one of Embodiments 1 to 4, wherein the SHP2 inhibitor is 2-((3S,4S)-4-amino-3-methyl-2-oxa-8-azaspiro[4.5]decan-8-yl)-5-(3-chloro-2-methoxypyridin-4-yl)-3-methyl-3,7-dihydro-4H-pyrrolo[2,3-d]pyrimidin-4-one.

Embodiment 48. The pharmaceutical combination of any one of Embodiments 1 to 4, wherein the SHP2 inhibitor is N-(3-((3-amino-5-(4-amino-4-methylpiperidin-1-yl)pyrazin-2-yl)thio)-2-chlorophenyl)-2-hydroxy-4-oxo-4H-pyrido[1,2-a]pyrimidine-3-carboxamide.

Embodiment 49. The pharmaceutical combination of any one of Embodiments 1 to 4, wherein the SHP2 inhibitor is N-(3-((3-amino-5-((3S,4S)-4-amino-3-methyl-2-oxa-8-azaspiro[4.5]decan-8-yl)pyrazin-2-yl)thio)-2-chlorophenyl)-2-hydroxy-4-oxo-6,7,8,9-tetrahydro-4H-pyrido[1,2-a]pyrimidine-3-carboxamide.

Embodiment 50. The pharmaceutical combination of any one of Embodiments 1 to 4, wherein the SHP2 inhibitor is N-(3-((3-amino-5-(4-amino-4-methylpiperidin-1-yl)pyrazin-2-yl)thio)-2-chlorophenyl)-4-hydroxy-2-oxo-1-phenyl-2,5-dihydro-1H-pyrrole-3-carboxamide.

Embodiment 51. The pharmaceutical combination of any one of Embodiments 1 to 4, wherein the SHP2 inhibitor is (R)—N-(3-((3-amino-5-(1-amino-8-azaspiro[4.5]decan-8-yl)pyrazin-2-yl)thio)-2-chlorophenyl)-2-hydroxy-4-oxo-6,7,8,9-tetrahydro-4H-pyrido[1,2-a]pyrimidine-3-carboxamide.

Embodiment 52. The pharmaceutical combination of any one of Embodiments 1 to 4, wherein the SHP2 inhibitor is N-(3-((3-amino-5-(4-(aminomethyl)-4-methylpiperidin-1-yl)pyrazin-2-yl)thio)-2-chlorophenyl)-2-hydroxy-4-oxo-6,7,8,9-tetrahydro-4H-pyrido[1,2-a]pyrimidine-3-carboxamide.

Embodiment 53. The pharmaceutical combination of any one of Embodiments 1 to 4, wherein the SHP2 inhibitor is (R)—N-(3-((3-amino-5-(1-amino-3,3-difluoro-8-azaspiro[4.5]decan-8-yl)pyrazin-2-yl)thio)-2-chlorophenyl)-2-hydroxy-4-oxo-6,7,8,9-tetrahydro-4H-pyrido[1,2-a]pyrimidine-3-carboxamide.

Embodiment 54. The pharmaceutical combination of any one of Embodiments 1 to 4, wherein the SHP2 inhibitor is N-(3-((3-amino-5-(4-(aminomethyl)-4-methylpiperidin-1-yl)pyrazin-2-yl)thio)-2-chlorophenyl)-2-hydroxy-4-oxo-4H-pyrido[1,2-a]pyrimidine-3-carboxamide.

Embodiment 55. The pharmaceutical combination of any one of Embodiments 1 to 4, wherein the SHP2 inhibitor is N-(3-((3-amino-5-(4-amino-4-(fluoromethyl)piperidin-1-yl)pyrazin-2-yl)thio)-2-chlorophenyl)-2-hydroxy-4-oxo-6,7,8,9-tetrahydro-4H-pyrido[1,2-a]pyrimidine-3-carboxamide.

Embodiment 56. The pharmaceutical combination of any one of Embodiments 1 to 4, wherein the SHP2 inhibitor is N-(3-((3-amino-5-(4-amino-4-(fluoromethyl)piperidin-1-yl)pyrazin-2-yl)thio)-2-chlorophenyl)-2-hydroxy-4-oxo-4H-pyrido[1,2-a]pyrimidine-3-carboxamide.

Embodiment 57. The pharmaceutical combination of any one of Embodiments 1 to 4, wherein the SHP2 inhibitor is (S)—N-(3-((3-amino-5-(4-amino-2-oxa-8-azaspiro[4.5]decan-8-yl)pyrazin-2-yl)thio)-2-chlorophenyl)-2-hydroxy-4-oxo-6,7,8,9-tetrahydro-4H-pyrido[1,2-a]pyrimidine-3-carboxamide.

Embodiment 58. The pharmaceutical combination of any one of Embodiments 1 to 4, wherein the SHP2 inhibitor is N-(3-((3-amino-5-(4-amino-4-methylpiperidin-1-yl)pyrazin-2-yl)thio)-2-chlorophenyl)-5-benzyl-4-hydroxy-1-methyl-2-oxo-2,5-dihydro-1H-pyrrole-3-carboxamide.

Embodiment 59. A pharmaceutical combination comprising:
(i) 5-chloro-N2-[2-isopropoxy-5-methyl-4-(4-piperidinyl)phenyl]-N4-[2-(isopropylsulfonyl)phenyl]-2,4-pyrimidinediamine (ceritinib), or a pharmaceutically acceptable salt thereof, and
(ii) a SHP2 inhibitor of any one of Embodiments 5 to 58, or a pharmaceutically acceptable salt thereof.

Embodiment 60. The pharmaceutical combination of any one of Embodiments 1 to 59 further comprising at least one pharmaceutically acceptable carrier.

Embodiment 61. A pharmaceutical composition comprising a pharmaceutical combination of any one of Embodiments 1 to 60 and at least one pharmaceutically acceptable carrier.

Except as otherwise indicated, the description or naming of a particular compound in the specification and claims is intended to include both individual enantiomers, diastereomeric mixtures, racemic or otherwise, thereof. Accordingly, this invention also includes all such isomers, including diastereomeric mixtures and resolved enantiomers of the compounds of this invention. Diastereomeric mixtures can be separated into their individual diastereomers on the basis of their physical chemical differences by methods known to those skilled in the art, for example, by chromatography or fractional crystallization. Enantiomers can be separated by converting the enantiomer mixture into a diastereomeric mixture by reaction with an appropriate optically active compound (e.g., alcohol), separating the diastereomers and converting (e.g., hydrolyzing) the individual diastereomers to the corresponding pure enantiomers. The methods for the determination of stereochemistry and the separation of stereoisomers are well known in the art (see discussion in Chapter 4 of "Advanced organic Chemistry", 4$^{th}$ edition, J. March. John Wiley and Sons, New York, 1992).

When referring to an ALK inhibitor, the term "salt" or "salts" is understood to be a salt of an ALK inhibitor and are preferably pharmaceutically acceptable salts. Pharmaceutically acceptable acid addition salts can be formed with inorganic acids and organic acids. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like.

As related to a SHP2 inhibitor, the term "salt" or "salts", unless otherwise indicated, includes salts of acidic and basic groups which may be present in the SHP2 inhibitor. A SHP2 inhibitor that is basic in nature is capable of forming a wide variety of salts with various inorganic and organic acids. Pharmaceutically acceptable acid addition salts can be formed with inorganic acids and organic acids. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like. Since a SHP2 inhibitor may include more than one acidic or basic moieties, the SHP2 inhibitor may include mono, di or tri-salts in a single active ingredient. In the case of an acidic moiety in a SHP2 inhibitor, a salt may be formed by treatment of a SHP2 inhibitor with a basic compound, particularly an inorganic base. For example, inorganic salts are those formed with alkali and alkaline earth metals such as lithium, sodium, potassium, barium and calcium. Organic base salts include, for example, ammonium, dibenzylammonium, benzylammonium, 2-hydroxyethylammonium, bis(2-hydroxyethyl)ammonium, phenylethylbenzylamine, dibenzyl-ethylenediamine, and the like salts. Other salts of acidic moieties may include, for example, those salts formed with procaine, quinine and N-methylglusoamine, and salts formed with basic amino acids such as glycine, ornithine, histidine, phenylglycine, lysine and arginine.

The term "pharmaceutically acceptable" is defined herein to refer to those compounds, materials, compositions and/or dosage forms, which are, within the scope of sound medical judgment, suitable for contact with the tissues a subject, e.g., a mammal or human, without excessive toxicity, irritation allergic response and other problem complications commensurate with a reasonable benefit/risk ratio.

Unless otherwise specified, or clearly indicated by the text, reference to therapeutic agents useful in the pharmaceutical combination of the present invention includes both the free form and all pharmaceutically acceptable salts of an ALK inhibitor and a SHP2 inhibitor.

In each case where citations of patent applications are given herein, the subject matter relating to the compounds is hereby incorporated into the present application by reference. The compounds used as therapeutic agents in the pharmaceutical combinations of the present invention can be prepared and administered as described in the cited documents, respectively. Also within the scope of this invention is the combination of two separate therapeutic agents as set forth herein, although a pharmaceutical combination within the scope of this invention could include three therapeutic agents or more.

The pharmaceutical compositions for separate administration of both combination partners, or for the administration in a fixed combination, i.e. a single galenical composition comprising the COMBINATION OF THE INVENTION, may be prepared in a manner known per se and are those suitable for enteral, such as oral or rectal, and parenteral administration to mammals (warm-blooded animals), including humans, comprising at least one pharmacologically active combination partner alone, e.g. as indicated above, or in combination with one or more pharmaceutically acceptable carriers, especially suitable for enteral or parenteral application. The pharmaceutical composition may contain, from about 0.1% to about 99.9%, preferably from about 1% to about 60%, of the therapeutic agent(s).

Suitable pharmaceutical compositions for the combination therapy for enteral or parenteral administration are, for example, those in unit dosage forms, such as coated tablets, tablets, capsules or suppositories, or ampoules. If not indicated otherwise, these are prepared in a manner known per se, for example by means of various conventional mixing, comminution, direct compression, granulating, coating, dissolving, lyophilizing processes, or fabrication techniques readily apparent to those skilled in the art. It will be appreciated that the unit content of a combination partner contained in an individual dose of each dosage form need not in itself constitute an effective amount since the necessary effective amount may be reached by administration of a plurality of dosage units, or the therapeutic effect may be achieved only after both combination partners are administered to the subject.

A unit dosage form containing the combination of agents or individual agents of the combination of agents may be in the form of micro-tablets enclosed inside a capsule, e.g. a gelatin capsule. For this, a gelatin capsule as is employed in pharmaceutical formulations can be used, such as the hard gelatin capsule.

The unit dosage forms of the present invention may optionally further comprise additional conventional carriers or excipients used for pharmaceuticals. Examples of such carriers include, but are not limited to, disintegrants, binders, lubricants, glidants, stabilizers, and fillers, diluents, colorants, flavours and preservatives. One of ordinary skill in the art may select one or more of the aforementioned carriers with respect to the particular desired properties of the dosage form. The amount of each carriers used may vary within ranges conventional in the art. The following references further disclose techniques and excipients used to formulate oral dosage forms. See *The Handbook of Pharmaceutical Excipients*, 4$^{th}$ edition, Rowe et al., Eds., American Pharmaceuticals Association (2003); and *Remington: the Science and Practice of Pharmacy*, 20$^{th}$ edition, Gennaro, Ed., Lippincott Williams & Wilkins (2003).

These optional additional conventional carriers may be incorporated into the oral dosage form either by incorporating the one or more conventional carriers into the initial mixture before or during granulation or by combining the one or more conventional carriers with granules comprising the combination of agents or individual agents of the combination of agents in the oral dosage form. In the latter embodiment, the combined mixture may be further blended, e.g., through a V-blender, and subsequently compressed or molded into a tablet, for example a monolithic tablet, encapsulated by a capsule, or filled into a sachet.

A therapeutically effective amount of an ALK inhibitor in vivo may range depending on the route of administration, between about 0.05 to about 50 mg per kg body weight per day, preferably about 0.1-25 mg/kg/day, more preferably from about 0.5-10 mg/kg/day, in single or divided doses. For a 70 kg human, this would amount to a preferable dosage range of about 35-750 mg per day. Daily dose of ceritinib can be for example 750 mg when fasted, or 450 or 600 mg with food. The recommended dose and schedule for crizotinib is 250 mg orally, twice daily, with or without food. Alectinib can be for example used by administering 300 mg twice daily. Lorlatinib dose used in clinic can for example be 100 mg once-daily, but can still change.

A therapeutically effective amount of a SHP2 inhibitor in vivo may range depending on the route of administration, between about 0.05 to about 15 mg per kg body weight per day, preferably about 0.1-5 mg/kg/day, more preferably from about 0.25-3 mg/kg/day, in single or divided doses. For a 70 kg human, this would amount to a preferable dosage range of about 17.5-210 mg per day.

In accordance with the present invention, a therapeutically effective amount of each of the combination partners, i.e. an ALK inhibitor and a SHP2 inhibitor, as defined herein, of the COMBINATION OF THE INVENTION may be administered simultaneously or sequentially and in any order, and the combination partners may be administered separately or as a fixed combination. For example, the method of treating a proliferative disease according to the invention may comprise (1) administration of the ALK inhibitor in free or a pharmaceutically acceptable salt form and (2) administration of the SHP2 INHIBITOR in free or a pharmaceutically acceptable salt form, simultaneously or sequentially in any order, in jointly therapeutically effective amounts, preferably in synergistically effective amounts, e.g. in daily or intermittently dosages. The individual combination partners, i.e. an ALK inhibitor and A SHP2 INHIBITOR, as defined herein, of the COMBINATION OF THE INVENTION may be administered separately at different times during the course of therapy or concurrently in divided or single combination forms. Furthermore, the term "administering" is therefore to be understood as embracing all such regimens of simultaneous or alternating treatment and the term "administering" is to be interpreted accordingly. The term also encompasses the use of a pro-drug of a combination partner that converts in vivo to the combination partner as such.

The effective dosage of each of the combination partners employed in the COMBINATION OF THE INVENTION may vary depending on the particular compound or pharmaceutical composition employed, the mode of administration, the condition being treated, and the severity of the condition being treated. Thus, the dosage regimen of the COMBINATION OF THE INVENTION is selected in accordance with a variety of factors including the route of administration and the renal and hepatic function of the patient. A clinician or physician of ordinary skill can readily determine and prescribe the effective amount of the single therapeutic agents required to alleviate, counter or arrest the progress of the condition.

The optimum ratios, individual and combined dosages, and concentrations of the combination partners, i.e. an ALK inhibitor and a SHP2 inhibitor, as defined herein, of the COMBINATION OF THE INVENTION that yield efficacy without toxicity are based on the kinetics of the therapeutic agents' availability to target sites, and may be determined using methods known to those of skill in the art.

The effective dosage of each of the combination partners may require more frequent administration of one of the compound(s) as compared to the other compound(s) in the combination. Therefore, to permit appropriate dosing, packaged pharmaceutical products may contain one or more dosage forms that contain the combination of compounds, and one or more dosage forms that contain one of the combination of compounds, but not the other compound(s) of the combination. When the combination partners, which are employed in the COMBINATION OF THE INVENTION, are marketed as single drugs, their dosage and mode of administration can be in accordance with the information provided on the package insert of the respective marketed drug, if not mentioned herein otherwise.

The optimal dosage of each combination partner for treatment of a proliferative disease can be determined empirically for each individual using known methods and will depend upon a variety of factors, including, though not limited to, the degree of advancement of the disease; the age, body weight, general health, gender and diet of the individual; the time and route of administration; and other medications the individual is taking.

The amount of each combination partner that may be combined with the carrier materials to produce a unit dosage form will vary depending upon the individual treated and the particular mode of administration. In some embodiments the unit dosage forms containing the combination of agents as described herein will contain the amounts of each agent of the combination that are typically administered when the agents are administered alone.

Frequency of dosage may vary depending on the compound used and the particular condition to be treated or prevented. Patients may generally be monitored for therapeutic effectiveness using assays suitable for the condition being treated or prevented, which will be familiar to those of ordinary skill in the art.

An aspect of the present invention further relates to a pharmaceutical preparation comprising:
- (1) one or more unit dosage forms of (i) an ALK inhibitor, or a pharmaceutically acceptable salt thereof, and
- (2) one or more unit dosage forms of (ii) a SHP2 inhibitor, or a pharmaceutically acceptable salt thereof.

Another aspect of the present invention further relates to a pharmaceutical preparation comprising:
- (1) one or more unit dosage forms of (i) 5-chloro-N2-[2-isopropoxy-5-methyl-4-(4-piperidinyl)phenyl]-N4-[2-(isopropylsulfonyl)phenyl]-2,4-pyrimidinediamine (ceritinib), or a pharmaceutically acceptable salt thereof, and
- (2) one or more unit dosage forms of (ii) a SHP2 inhibitor, or a pharmaceutically acceptable salt thereof.

Various enumerated embodiments of the pharmaceutical preparation aspect of the invention are described herein. It will be recognized that features specified in each embodiment may be combined with other specified features to provide further embodiments of the present invention.

Embodiment 62. A pharmaceutical preparation comprising:
- (1) one or more unit dosage forms of (i) an ALK inhibitor, or a pharmaceutically acceptable salt thereof, selected from 5-chloro-N2-[2-isopropoxy-5-methyl-4-(4-piperidinyl)phenyl]-N4-[2-(isopropylsulfonyl)phenyl]-2,4-pyrimidinediamine (ceritinib), 9-Ethyl-6,6-dimethyl-8-[4-(4-morpholinyl)-1-piperidinyl]-11-oxo-6,11-dihydro-5H-benzo[b]carbazole-3-carbonitrile (alectinib) and (10R)-7-Amino-12-fluoro-2,10,16-trimethyl-15-oxo-10,15,16,17-tetrahydro-2H-8,4-(metheno)pyrazolo[4,3-h][2,5,11]-benzoxadiazacyclotetradecine-3-carbonitrile (loratinib), and
- (2) one or more unit dosage forms of (ii) a SHP2 inhibitor, or a pharmaceutically acceptable salt thereof.

Embodiment 63. A pharmaceutical preparation comprising:
- (1) one or more unit dosage forms of (i) an ALK inhibitor, or a pharmaceutically acceptable salt thereof, selected from 5-chloro-N2-[2-isopropoxy-5-methyl-4-(4-piperidinyl)phenyl]-N4-[2-(isopropylsulfonyl)phenyl]-2,4-pyrimidinediamine (ceritinib), 9-Ethyl-6,6-dimethyl-8-[4-(4-morpholinyl)-1-piperidinyl]-11-oxo-6,11-dihydro-5H-benzo[b]carbazole-3-carbonitrile (alectinib) and (10R)-7-Amino-12-fluoro-2,10,16-trimethyl-15-oxo-10,15,16,17-tetrahydro-2H-8,4-(metheno)pyrazolo[4,3-h][2,5,11]-benzoxadiazacyclotetradecine-3-carbonitrile (loratinib), and
- (2) one or more unit dosage forms of (ii) a SHP2 inhibitor of Table 1, or a pharmaceutically acceptable salt thereof.

Embodiment 64. A pharmaceutical preparation comprising:
- (1) one or more unit dosage forms of (i) an ALK inhibitor, or a pharmaceutically acceptable salt thereof, selected from 5-chloro-N2-[2-isopropoxy-5-methyl-4-(4-piperidinyl)phenyl]-N4-[2-(isopropylsulfonyl)phenyl]-2,4-pyrimidinediamine (ceritinib), 9-Ethyl-6,6-dimethyl-8-[4-(4-morpholinyl)-1-piperidinyl]-11-oxo-6,11-dihydro-5H-benzo[b]carbazole-3-carbonitrile (alectinib) and (10R)-7-Amino-12-fluoro-2,10,16-trimethyl-15-oxo-10,15,16,17-tetrahydro-2H-8,4-(metheno)pyrazolo[4,3-h][2,5,11]-benzoxadiazacyclotetradecine-3-carbonitrile (loratinib), and
- (2) one or more unit dosage forms of (ii) a SHP2 inhibitor of any one of Embodiments 5 to 59, or a pharmaceutically acceptable salt thereof.

Embodiment 65. A pharmaceutical preparation comprising:
- (1) one or more unit dosage forms of (i) 5-chloro-N2-[2-isopropoxy-5-methyl-4-(4-piperidinyl)phenyl]-N4-[2-(isopropylsulfonyl)phenyl]-2,4-pyrimidinediamine (ceritinib), or a pharmaceutically acceptable salt thereof, and
- (2) one or more unit dosage forms of (ii) a SHP2 inhibitor of Table 1, or a pharmaceutically acceptable salt thereof.

Embodiment 66. A pharmaceutical preparation comprising:
- (1) one or more unit dosage forms of (i) 5-chloro-N2-[2-isopropoxy-5-methyl-4-(4-piperidinyl)phenyl]-N4-[2-(isopropylsulfonyl)phenyl]-2,4-pyrimidinediamine (ceritinib), or a pharmaceutically acceptable salt thereof, and
- (2) one or more unit dosage forms of (ii) a SHP2 inhibitor of any one of Embodiments 5 to 59, or a pharmaceutically acceptable salt thereof.

Embodiment 67. The pharmaceutical preparation of any one of Embodiments 61 to 66 further comprising at least one pharmaceutically acceptable carrier.

A combination of the invention, as defined herein, could be effective for the treatment of a proliferative disease, such as cancer, particularly lung cancer. In particular, a combination, as defined herein, could result, for example, in an unexpected improvement, over monotherapy with an ALK inhibitor, in the treatment ALK-rearranged NSCLC, including when such NSCLC is resistant to treatment with an ALK inhibitor alone.

Particularly effective is the combination in the treatment of ALK rearranged or ALK-positive cancer. The ALK-positive cancer can be anaplastic large-cell lymphoma, gastric cancer, colorectal cancer, breast cancers, oesophageal cancer, neuroblastoma, inflammatory myofibroblastic tumor, renal cancer, pancreatic cancer or lung cancer. Specifically, the cancer can be ALK-positive non-small cell lung cancer or ALK-positive neuroblastoma, preferably NSCLC. Since the combination has proven to be effective even in cancer resistant to an ALK inhibitor, the combination can be successfully employed in the treatment of said cancer. The cancer can be resistant either to the same ALK inhibitor as used in the combination or a different one. The combination can thus be added as a second line treatment after the disease has progressed or cancer has become resistant to the ALK inhibitor alone. The experiments have shown that the combination overcomes resistance that arose via ALK inactivation mutation or through ALK-independent resistance, i.e. via a compensatory pathway (by-pass pathway). The combination can be utilized in both situations. Preferably, the combination of the present invention is used in cancer characterized by an ALK-independent resistance.

The combination of the invention may provide a synergistic therapeutic effect, e.g. with regard to alleviating, delaying progression of or inhibiting the symptoms of proliferative diseases, such as cancer, particularly lung cancer. Certain combinations of the invention may provide an additive effect, e.g. with regard to alleviating, delaying progression of or inhibiting the symptoms of proliferative diseases, such as cancer, particularly lung cancer.

Thus, an aspect of the present invention particularly pertains to a pharmaceutical combination comprising:
  (i) an ALK inhibitor, or a pharmaceutically acceptable salt thereof, and
  (ii) a SHP2 inhibitor, or a pharmaceutically acceptable salt thereof, for use in the treatment of cancer.

Another aspect of the present invention particularly pertains to a pharmaceutical combination comprising:
  (i) 5-chloro-N2-[2-isopropoxy-5-methyl-4-(4-piperidinyl)phenyl]-N4-[2-(isopropylsulfonyl)phenyl]-2,4-pyrimidinediamine (ceritinib), or a pharmaceutically acceptable salt thereof, and
  (ii) a SHP2 inhibitor, or a pharmaceutically acceptable salt thereof, for use in the treatment of cancer.

Various enumerated embodiments of the use of a pharmaceutical combination of the invention are described herein. It will be recognized that features specified in each embodiment may be combined with other specified features to provide further embodiments of the present invention.

Embodiment 68. The pharmaceutical combination of any one of Embodiments 1 to 60, or the pharmaceutical composition of Embodiment 61, wherein the ALK inhibitor, or a pharmaceutically acceptable salt thereof, and the SHP2 inhibitor, or a pharmaceutically acceptable salt thereof, are provided jointly in synergistically effective amounts for use in the treatment of cancer.

Embodiment 69. The pharmaceutical combination of any one of Embodiments 1 to 60, or the pharmaceutical composition of Embodiment 61, for use in the treatment of cancer.

Embodiment 70. Use of the pharmaceutical combination of any one of Embodiments 1 to 60, or the use of the pharmaceutical composition of Embodiment 61, in the treatment of cancer, wherein the ALK inhibitor, or a pharmaceutically acceptable salt thereof, and the SHP2 inhibitor, or a pharmaceutically acceptable salt thereof, are provided jointly in synergistically effective amounts.

Embodiment 71. Use of the pharmaceutical combination of any one of Embodiments 1 to 60, or the use of the pharmaceutical composition of Embodiment 61, in the treatment of cancer.

Embodiment 72. The pharmaceutical combination of Embodiment 68 or Embodiment 69, the pharmaceutical composition of Embodiment 68 or Embodiment 69, use of the pharmaceutical combination of Embodiment 70 or Embodiment 71, or use of the pharmaceutical composition of Embodiment 70 or Embodiment 71, wherein the cancer is an ALK-positive cancer.

Embodiment 73. The pharmaceutical combination of Embodiment 68 or Embodiment 69, the pharmaceutical composition of Embodiment 68 or Embodiment 69, use of the pharmaceutical combination of Embodiment 70 or Embodiment 71, or use of the pharmaceutical composition of Embodiment 70 or Embodiment 71, wherein the cancer is an ALK-positive cancer selected from anaplastic large-cell lymphoma, gastric cancer, breast cancers, oesophageal cancer, colorectal cancer, neuroblastoma, inflammatory myofibroblastic tumor, renal cancer, pancreatic cancer and lung cancer.

Embodiment 74. The pharmaceutical combination of Embodiment 68 or Embodiment 69, the pharmaceutical composition of Embodiment 68 or Embodiment 69, use of the pharmaceutical combination of Embodiment 70 or Embodiment 71, or use of the pharmaceutical composition of Embodiment 70 or Embodiment 71, wherein the cancer is ALK-positive non-small cell lung cancer.

Embodiment 75. The pharmaceutical combination of Embodiment 68 or Embodiment 69, the pharmaceutical composition of Embodiment 68 or Embodiment 69, use of the pharmaceutical combination of Embodiment 70 or Embodiment 71, or use of the pharmaceutical composition of Embodiment 70 or Embodiment 71, wherein the cancer is ALK-positive neuroblastoma.

Embodiment 76. The pharmaceutical combination of Embodiment 68 or Embodiment 69, the pharmaceutical composition of Embodiment 68 or Embodiment 69, use of the pharmaceutical combination of Embodiment 70 or Embodiment 71, or use of the pharmaceutical composition of Embodiment 70 or Embodiment 71, wherein the cancer is an ALK-positive cancer resistant to an ALK inhibitor.

Embodiment 77. The pharmaceutical combination of Embodiment 68 or Embodiment 69, the pharmaceutical composition of Embodiment 68 or Embodiment 69, use of the pharmaceutical combination of Embodiment 70 or Embodiment 71, or use of the pharmaceutical composition of Embodiment 70 or Embodiment 71, wherein the cancer is an ALK-positive cancer resistant to the ALK inhibitor of the pharmaceutical combination.

Embodiment 78. The pharmaceutical combination of Embodiment 68 or Embodiment 69, the pharmaceutical composition of Embodiment 68 or Embodiment 69, use of the pharmaceutical combination of Embodiment 70 or Embodiment 71, or use of the pharmaceutical composition of Embodiment 70 or Embodiment 71, wherein the cancer is an ALK-positive cancer characterized by ALK-independent resistance to an ALK inhibitor.

An aspect of the present invention relates to a method of treating a proliferative disease, such as cancer, in a subject in need thereof, comprising the administration of a COMBINATION OF THE INVENTION to said subject.

Another aspect of the present invention relates to a method of treating a proliferative disease, such as cancer, in a subject in need thereof, comprising the simultaneous or sequential administration to said subject a therapeutically effective amount of:
(i) an ALK inhibitor, or a pharmaceutically acceptable salt thereof, and
(ii) a SHP2 inhibitor, or a pharmaceutically acceptable salt thereof.

Another aspect of the present invention relates to a method of treating a proliferative disease, such as cancer, in a subject in need thereof, comprising the simultaneous or sequential administration to said subject a therapeutically effective amount of:
(i) 5-chloro-N2-[2-isopropoxy-5-methyl-4-(4-piperidinyl)phenyl]-N4-[2-(isopropylsulfonyl)phenyl]-2,4-pyrimidinediamine (ceritinib), or a pharmaceutically acceptable salt thereof, and
(ii) a SHP2 inhibitor, or a pharmaceutically acceptable salt thereof, and optionally at least one pharmaceutically acceptable carrier.

Various enumerated embodiments of the methods of treatment using a pharmaceutical combination of the invention are described herein. It will be recognized that features specified in each embodiment may be combined with other specified features to provide further embodiments of the present invention.

Embodiment 79. A method for treating cancer, in a subject in need thereof, comprising the simultaneous or sequential administration to said subject a therapeutically effective amount of:
(i) an ALK inhibitor, or a pharmaceutically acceptable salt thereof, selected from 5-chloro-N2-[2-isopropoxy-5-methyl-4-(4-piperidinyl)phenyl]-N4-[2-(isopropylsulfonyl)phenyl]-2,4-pyrimidinediamine (ceritinib), 9-Ethyl-6,6-dimethyl-8-[4-(4-morpholinyl)-1-piperidinyl]-11-oxo-6,11-dihydro-5H-benzo[b]carbazole-3-carbonitrile (alectinib) and (10R)-7-Amino-12-fluoro-2,10,16-trimethyl-15-oxo-10,15,16,17-tetrahydro-2H-8,4-(metheno)pyrazolo[4,3-h][2,5,11]-benzoxadiazacyclotetradecine-3-carbonitrile (loratinib), and
(ii) a SHP2 inhibitor, or a pharmaceutically acceptable salt thereof, and optionally at least one pharmaceutically acceptable carrier.

Embodiment 80. A method for treating cancer, in a subject in need thereof, comprising the simultaneous or sequential administration to said subject a therapeutically effective amount of:
(i) an ALK inhibitor, or a pharmaceutically acceptable salt thereof, selected from 5-chloro-N2-[2-isopropoxy-5-methyl-4-(4-piperidinyl)phenyl]-N4-[2-(isopropylsulfonyl)phenyl]-2,4-pyrimidinediamine (ceritinib), 9-Ethyl-6,6-dimethyl-8-[4-(4-morpholinyl)-1-piperidinyl]-11-oxo-6,11-dihydro-5H-benzo[b]carbazole-3-carbonitrile (alectinib) and (10R)-7-Amino-12-fluoro-2,10,16-trimethyl-15-oxo-10,15,16,17-tetrahydro-2H-8,4-(metheno)pyrazolo[4,3-h][2,5,11]-benzoxadiazacyclotetradecine-3-carbonitrile (loratinib), and
(ii) a SHP2 inhibitor of Table 1, or a pharmaceutically acceptable salt thereof, and optionally at least one pharmaceutically acceptable carrier.

Embodiment 81. A method for treating cancer, in a subject in need thereof, comprising the simultaneous or sequential administration to said subject a therapeutically effective amount of:
(i) an ALK inhibitor, or a pharmaceutically acceptable salt thereof, selected from 5-chloro-N2-[2-isopropoxy-5-methyl-4-(4-piperidinyl)phenyl]-N4-[2-(isopropylsulfonyl)phenyl]-2,4-pyrimidinediamine (ceritinib), 9-Ethyl-6,6-dimethyl-8-[4-(4-morpholinyl)-1-piperidinyl]-11-oxo-6,11-dihydro-5H-benzo[b]carbazole-3-carbonitrile (alectinib) and (10R)-7-Amino-12-fluoro-2,10,16-trimethyl-15-oxo-10,15,16,17-tetrahydro-2H-8,4-(metheno)pyrazolo[4,3-h][2,5,11]-benzoxadiazacyclotetradecine-3-carbonitrile (loratinib), and
(ii) a SHP2 inhibitor of any one of Embodiments 5 to 58, or a pharmaceutically acceptable salt thereof, and optionally at least one pharmaceutically acceptable carrier.

Embodiment 82. A method for treating cancer, in a subject in need thereof, comprising the simultaneous or sequential administration to said subject a therapeutically effective amount of:
(i) 5-chloro-N2-[2-isopropoxy-5-methyl-4-(4-piperidinyl)phenyl]-N4-[2-(isopropylsulfonyl)phenyl]-2,4-pyrimidinediamine (ceritinib), or a pharmaceutically acceptable salt thereof, and
(ii) a SHP2 inhibitor of Table 1, or a pharmaceutically acceptable salt thereof, and optionally at least one pharmaceutically acceptable carrier.

Embodiment 83. A method for treating cancer, in a subject in need thereof, comprising the simultaneous or sequential administration to said subject of a therapeutically effective amount of:
(i) 5-chloro-N2-[2-isopropoxy-5-methyl-4-(4-piperidinyl)phenyl]-N4-[2-(isopropylsulfonyl)phenyl]-2,4-pyrimidinediamine (ceritinib), or a pharmaceutically acceptable salt thereof, and
(ii) a SHP2 inhibitor of any one of Embodiments 5 to 58, or a pharmaceutically acceptable salt thereof, and optionally at least one pharmaceutically acceptable carrier.

Embodiment 84. The method of any one of Embodiments 79 to 83, wherein the cancer is an ALK-positive cancer.

Embodiment 85. The method of any one of Embodiments 79 to 83, wherein the cancer is an ALK-positive cancer selected from anaplastic large-cell lymphoma, gastric cancer, breast cancers, oesophageal cancer, colorectal cancer, neuroblastoma, inflammatory myofibroblastic tumor, renal cancer, pancreatic cancer and lung cancer.

Embodiment 86. The method of any one of Embodiments 79 to 83, wherein the cancer is ALK-positive non-small cell lung cancer.

Embodiment 87. The method of any one of Embodiments 79 to 83, wherein the cancer is ALK-positive neuroblastoma.

Embodiment 88. The method of any one of Embodiments 79 to 83, wherein the cancer is an ALK-positive cancer resistant to an ALK inhibitor.

Embodiment 89. The method of any one of Embodiments 79 to 83, wherein the cancer is an ALK-positive cancer resistant to the ALK inhibitor of the pharmaceutical combination.

Embodiment 90. The method of any one of Embodiments 79 to 83, wherein the cancer is an ALK-positive cancer characterized by ALK-independent resistance to an ALK inhibitor.

An aspect of the present invention relates to pharmaceutical combinations or pharmaceutical compositions comprising:
(i) an ALK inhibitor, or a pharmaceutically acceptable salt thereof, and (ii) a SHP2 inhibitor, or a pharmaceutically acceptable salt thereof, and optionally at least one pharmaceutically acceptable carrier, for use as a medicament.

Another aspect of the present invention relates to pharmaceutical combinations or pharmaceutical compositions comprising:
- (i) 5-chloro-N2-[2-isopropoxy-5-methyl-4-(4-piperidinyl)phenyl]-N4-[2-(isopropylsulfonyl)phenyl]-2,4-pyrimidinediamine (ceritinib), or a pharmaceutically acceptable salt thereof, and
- (ii) a SHP2 inhibitor, or a pharmaceutically acceptable salt thereof, and optionally at least one pharmaceutically acceptable carrier, for use as a medicament.

Various enumerated embodiments of the invention are described herein. It will be recognized that features specified in each embodiment may be combined with other specified features to provide further embodiments of the present invention.

Embodiment 91. Use of the pharmaceutical combination of any one of Embodiments 1 to 60, or use of the pharmaceutical composition of Embodiment 61 as a medicament.

An aspect of the present invention relates to pharmaceutical combinations or pharmaceutical compositions comprising:
- (i) an ALK inhibitor, or a pharmaceutically acceptable salt thereof, and
- (ii) a SHP2 inhibitor, or a pharmaceutically acceptable salt thereof, and optionally at least one pharmaceutically acceptable carrier, for use in the manufacture of a medicament for the treatment of cancer.

Another aspect of the present invention relates to pharmaceutical combinations or pharmaceutical compositions comprising:
- (i) 5-chloro-N2-[2-isopropoxy-5-methyl-4-(4-piperidinyl)phenyl]-N4-[2-(isopropylsulfonyl)phenyl]-2,4-pyrimidinediamine (ceritinib), or a pharmaceutically acceptable salt thereof, and
- (ii) a SHP2 inhibitor, or a pharmaceutically acceptable salt thereof, and optionally at least one pharmaceutically acceptable carrier, for use in the manufacture of a medicament for the treatment of cancer.

Various enumerated embodiments of the invention are described herein. It will be recognized that features specified in each embodiment may be combined with other specified features to provide further embodiments of the present invention.

Embodiment 92. Use of the pharmaceutical combination of any one of Embodiments 1 to 60, or use of the pharmaceutical composition of Embodiment 61 in the manufacture of a medicament for the treatment of cancer.

Embodiment 93. The use of Embodiment 92, wherein the cancer is an ALK-positive cancer.

Embodiment 94. The use of Embodiment 92, wherein the cancer is an ALK-positive cancer selected from anaplastic large-cell lymphoma, gastric cancer, breast cancers, oesophageal cancer, colorectal cancer, neuroblastoma, inflammatory myofibroblastic tumor, renal cancer, pancreatic cancer and lung cancer.

Embodiment 95. The use of Embodiment 92, wherein the cancer is ALK-positive non-small cell lung cancer.

Embodiment 96. The use of Embodiment 92, wherein the cancer is ALK-positive neuroblastoma.

Embodiment 97. The use of Embodiment 92, wherein the cancer is an ALK-positive cancer resistant to an ALK inhibitor.

Embodiment 98. The use of Embodiment 92, wherein the cancer is an ALK-positive cancer resistant to the ALK inhibitor of the pharmaceutical combination.

Embodiment 99. The use of Embodiment 92, wherein the cancer is an ALK-positive cancer characterized by ALK-independent resistance to an ALK inhibitor.

The present disclosure further provides a commercial package comprising as therapeutic agents a combination comprising: (a) an ALK inhibitor, or a pharmaceutically acceptable salt thereof, and (b) a SHP2 inhibitor, or a pharmaceutically acceptable salt thereof, and optionally at least one pharmaceutically acceptable carrier for use in the preparation of a pharmaceutical composition, together with instructions for simultaneous, separate or sequential administration thereof for use in the treatment of cancer.

An aspect of the present invention relates to a commercial package comprising a pharmaceutical combination comprising:
- (i) an ALK inhibitor, or a pharmaceutically acceptable salt thereof, and
- (ii) a SHP2 inhibitor, or a pharmaceutically acceptable salt thereof, together with instructions for simultaneous or sequential administration thereof for use in the treatment of a proliferative disease, such as cancer.

Another aspect of the present invention relates to a commercial package comprising a pharmaceutical combination comprising:
- (i) 5-chloro-N2-[2-isopropoxy-5-methyl-4-(4-piperidinyl)phenyl]-N4-[2-(isopropylsulfonyl)phenyl]-2,4-pyrimidinediamine (ceritinib), or a pharmaceutically acceptable salt thereof, and
- (ii) a SHP2 inhibitor, or a pharmaceutically acceptable salt thereof, together with instructions for simultaneous or sequential administration thereof for use in the treatment of a proliferative disease, such as cancer.

Various enumerated embodiments of the invention are described herein. It will be recognized that features specified in each embodiment may be combined with other specified features to provide further embodiments of the present invention.

Embodiment 100. A commercial package comprising the pharmaceutical combination of any one of Embodiments 1 to 60, together with instructions for simultaneous or sequential administration thereof for use in the treatment of cancer.

Embodiment 101. The commercial package of Embodiment 100, wherein the cancer is an ALK-positive cancer.

Embodiment 102. The commercial package of Embodiment 100, wherein the cancer is an ALK-positive cancer selected from anaplastic large-cell lymphoma, gastric cancer, breast cancers, oesophageal cancer, colorectal cancer, neuroblastoma, inflammatory myofibroblastic tumor, renal cancer, pancreatic cancer and lung cancer.

Embodiment 103. The commercial package of Embodiment 100, wherein the cancer is ALK-positive non-small cell lung cancer.

Embodiment 104. The commercial package of Embodiment 100, wherein the cancer is ALK-positive neuroblastoma.

Embodiment 105. The commercial package of Embodiment 100, wherein the cancer is an ALK-positive cancer resistant to an ALK inhibitor.

Embodiment 106. The commercial package of Embodiment 100, wherein the cancer is an ALK-positive cancer resistant to the ALK inhibitor of the pharmaceutical combination.

Embodiment 107. The commercial package of Embodiment 100, wherein the cancer is an ALK-positive cancer characterized by ALK-independent resistance to an ALK inhibitor.

The following Examples illustrate the invention described above; they are not, however, intended to limit the scope of the invention in any way. The beneficial effects of the pharmaceutical combination of the present invention can also be determined by other test models known as such to the person skilled in the pertinent art.

Below are a list of certain abbreviations used throughout the disclosure.

| Abbreviation | Description |
|---|---|
| ATCC | American Type Culture Collection |
| DCM | dichloromethane |
| DIPEA | N,N-diisopropylethylamine, N-ethyl-N-isopropylpropan-2-amine |
| DMF | N,N-dimethylformamide |
| DMSO | dimethylsulfoxide |
| EtOAc | ethyl acetate |
| h. | hour |
| HPLC | High-performance liquid chromatography |
| M | molar |
| min | minutes |
| ml or mL | millilitre |
| m/z | mass to charge ratio |
| NMP | N-methylpyrrolidinone, 1-methyl-2-pyrrolidinone |
| NMR | Nuclear magnetic resonance |
| PBS | Phosphate Buffered Saline |
| RT | Room Temperature |
| TFA | trifluoroacetic acid |

EXAMPLES

Example 1: The synthesis of N-(3-((3-amino-5-(4-amino-4-methylpiperidin-1-yl)pyrazin-2-yl)thio)-2-chlorophenyl)-2-hydroxy-4-oxo-4H-pyrido[1,2-a]pyrimidine-3-carboxamide (Compound No. 44 of Table 1)

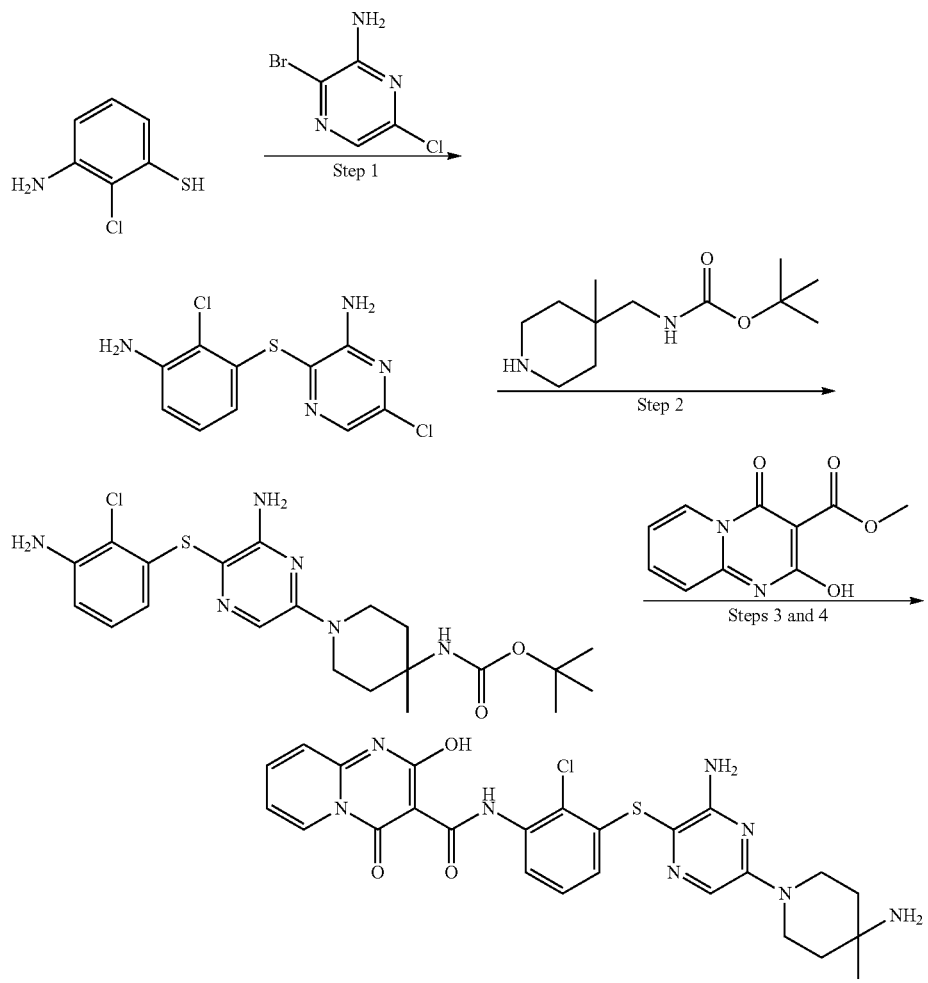

Step 1: A suspension of 3-amino-2-chlorobenzenethiol hydrochloride (8.0 g, 40.8 mmol), 3-bromo-6-chloropyrazin-2-amine (6.0 g, 28.8 mmol), Cu(I) iodide (1.1 g, 5.8 mmol), 1,10-phenanthroline (2.1 g, 11.7 mmol) and potassium phosphate (12.5 g, 58.9 mmol) in dioxane (80 mL) was heated to 85° C. for 4 h. After cooling to RT, the reaction mixture was diluted with EtOAc (100 mL), filtered through a pad of Celite®, concentrated under reduced pressure to an oil and suspended in DCM (100 mL). The resulting off-white precipitate was collected by filtration and dried to give 3-((3-amino-2-chlorophenyl)thio)-6-chloropyrazin-2-amine (6.5 g). MS m/z 287.1 (M+H)$^+$.

Step 2: A suspension of 3-((3-amino-2-chlorophenyl)thio)-6-chloropyrazin-2-amine (0.29 g, 1.0 mmol), tert-butyl (4-methylpiperidin-4-yl)carbamate (0.43 g, 2.0 mmol) and DIPEA (0.87 mL, 5.0 mmol) in NMP (5 mL) was radiated in a microwave reactor to 150° C. for 2 h. After cooling to RT, the reaction mixture was diluted with EtOAc (100 mL), washed with water and brine, dried over MgSO$_4$, filtered and concentrated under reduced pressure. The crude product was purified by silica chromatography (10-50% EtOAc/heptane) to give 0.44 g of tert-butyl (1-(6-amino-5-((3-amino-2-chlorophenyl)thio)pyrazin-2-yl)-4-methylpiperidin-4-yl)carbamate. MS m/z 465.2 (M+H)$^+$.

Step 3: A suspension of tert-butyl (1-(6-amino-5-((3-amino-2-chlorophenyl)thio)pyrazin-2-yl)-4-methylpiperidin-4-yl)carbamate (0.13 g, 0.26 mmol) and methyl 2-hydroxy-4-oxo-4H-pyrido[1,2-a]pyrimidine-3-carboxylate (69.1 mg, 0.314 mmol) in bromobenzene (2 mL) was heated to 170° C. in a microwave reactor for 1 h. After cooling the reaction mixture to RT, it was concentrated under reduced pressure and the resulting residue was purified by HPLC (15-40% MeCN in water, 0.1% NH$_4$OH modifier), to give tert-butyl (1-(6-amino-5-((2-chloro-3-(2-hydroxy-4-oxo-4H-pyrido[1,2-a]pyrimidine-3-carboxamido)phenyl)thio)pyrazin-2-yl)-4-methylpiperidin-4-yl)carbamate (0.09 g). MS m/z 653.3 (M+H)$^+$.

Step 4: To a solution of tert-butyl (1-(6-amino-5-((2-chloro-3-(2-hydroxy-4-oxo-4H-pyrido[1,2-a]pyrimidine-3-carboxamido)phenyl)thio)pyrazin-2-yl)-4-methylpiperidin-4-yl)carbamate (0.09 g, 0.14 mmol) in DCM (0.5 mL) was added TFA (0.5 mL). After stirring at RT for 2 h, the volatiles were removed under reduced pressure and the resulting residue was purified by HPLC (15-40% MeCN in water, 0.1% TFA modifier). The lyophilized product was dissolved in MeOH containing HCl (1.2 M) and dried to give N-(3-((3-amino-5-(4-amino-4-methylpiperidin-1-yl)pyrazin-2-yl)thio)-2-chlorophenyl)-2-hydroxy-4-oxo-4H-pyrido[1,2-a]pyrimidine-3-carboxamide as the HCl salt (0.085 g). $^1$H NMR (400 MHz, Methanol-d$_4$) δ ppm 9.19 (d, J=6.8 Hz, 1H), 8.34 (d, J=8.0 Hz, 1H), 8.24 (t, J=7.9 Hz, 1H), 7.81 (s, 1H), 7.61 (d, J=8.7 Hz, 1H), 7.52 (d, J=7.1 Hz, 1H), 7.29 (t, J=8.3 Hz, 1H), 6.74 (d, J=7.9 Hz, 1H), 4.26 (d, J=14.2 Hz, 2H), 3.52 (m, 2H), 1.93 (m, 4H), 1.53 (s, 3H). HRMS calcd for C$_{25}$H$_{26}$ClN$_8$O$_3$S (M+H)$^+$ 553.1537, found 553.1524. The IC$_{50}$=0.006 μM.

Using appropriate starting materials Compound Nos. 45-54 were synthesized using similar method described in Example 1.

Example 3

Compound Nos. 1-3 of Table 1 were synthesized using the methods described in WO2015/107493.
Compound No. 4 was synthesized using the methods described in WO2015/107494.
Compound Nos. 5-17 were synthesized using the methods described in WO2015/107495.
Compound Nos. 18-24 were synthesized using the methods described in PCT/IB2016053550.
Compound Nos. 25-36 were synthesized using the methods described in PCT/IB2016053549.
Compound Nos. 37-43 were synthesized using the methods described in PCT/IB2016053548.

Example 4: Compounds of Table 1 were Assessed for their Ability to Selectively Inhibit SHP2 Activity. The Inhibitory Properties of the Compounds of the Invention Described Herein can be Evidenced by Testing in any One of the Following Assays SHP2 Allosteric Inhibition Assay SHP2 is allosterically activated through binding of bis-tyrosyl-phorphorylated peptides to its Src Homology 2 (SH2) domains. The latter activation step leads to the release of the auto-inhibitory interface of SHP2, which in turn renders the SHP2 protein tyrosine phosphatase (PTP) active and available for substrate recognition and reaction catalysis. The catalytic activity of SHP2 was monitored using the surrogate substrate DiFMUP in a prompt fluorescence assay format.

More specifically, the phosphatase reactions were performed at room temperature in 384-well black polystyrene plate, flat bottom, low flange, non-binding surface (Corning, Cat #3575) using a final reaction volume of 25 μL and the following assay buffer conditions: 60 mM HEPES, pH 7.2, 75 mM NaCl, 75 mM KCl, 1 mM EDTA, 0.05% P-20, 5 mM DTT.

The inhibition of SHP2 (concentrations varying from 0.003-100 μM) was monitored using an assay in which 0.5 nM of SHP2 was incubated with of 0.5 μM of peptide IRS1_pY1172(dPEG8)pY1222 (sequence: H2N-LN(pY)IDLDLV(dPEG8)LST(pY)ASINFQK-amide (SEQ ID NO: 1)). After 30-60 minutes incubation at 25° C., the surrogate substrate DiFMUP (Invitrogen, cat #D6567) was added to the reaction and incubated at 25° C. for 30 minutes. The reaction was then quenched by the addition of 5 μL of a 160 μM solution of bpV(Phen) (Enzo Life Sciences cat #ALX-270-204). The fluorescence signal was monitored using a microplate reader (Envision, Perki-Elmer) using excitation and emission wavelengths of 340 nm and 450 nm, respectively. The inhibitor dose response curves were analyzed using normalized IC$_{50}$ regression curve fitting with control based normalization. The IC$_{50}$ values for the compounds of Table 1 are given in Table 2 below.

TABLE 2

| SHP2 inhibition (allosteric assay) | |
|---|---|
| Compound No. | IC$_{50}$ (μM) |
| 1 | 0.071 |
| 2 | 0.065 |
| 3 | 0.076 |
| 4 | 0.029 |
| 5 | 0.011 |
| 6 | 0.014 |
| 7 | 0.039 |
| 8 | 0.155 |
| 9 | 0.073 |
| 10 | 0.025 |
| 11 | 0.007 |
| 12 | 0.005 |

TABLE 2-continued

SHP2 inhibition (allosteric assay)

| Compound No. | IC$_{50}$ (μM) |
|---|---|
| 13 | 0.003 |
| 14 | 0.004 |
| 15 | 0.009 |
| 16 | 0.010 |
| 17 | 0.009 |
| 18 | 0.0045 |
| 19 | 0.006 |
| 20 | 0.006 |
| 21 | 0.014 |
| 22 | 0.008 |
| 23 | 0.007 |
| 24 | 0.006 |
| 25 | 0.053 |
| 26 | 0.048 |
| 27 | 0.033 |
| 28 | 0.018 |
| 29 | 0.014 |
| 30 | 0.017 |
| 31 | 0.021 |
| 32 | 0.020 |
| 33 | 0.014 |
| 34 | 0.093 |
| 35 | 0.174 |
| 36 | 0.025 |
| 37 | 0.026 |
| 38 | 0.062 |
| 39 | 0.067 |
| 40 | 0.016 |
| 41 | 0.009 |
| 42 | 0.036 |
| 43 | 0.026 |
| 44 | 0.006 |
| 45 | 0.023 |
| 46 | 0.004 |
| 47 | 0.001 |
| 48 | 0.006 |
| 49 | 0.042 |
| 50 | 0.007 |
| 51 | 0.006 |
| 52 | 0.005 |
| 53 | 0.018 |
| 54 | 0.0073 |

Example 5: Cell Growth Inhibition and Synergy Assessment in ALK Positive Cell Lines after Treatment with Combinations of the Present Invention Cell Lines The MGH049, MGH045-2A and MGH073-2B cell lines were established at Massachusetts General Hospital. MGH049 is described in Friboulet L, et al. Cancer Discov. 2014 June; 4(6):662-73. MGH045 is described in Friboulet L, et al. Cancer Discov. 2014 June; 4(6):662-73). MGH045-1A, is described in Science, 2014, December 19; 346(6216): 1480-1).

All human lung cancer samples were obtained from patients with informed consent, and all procedures were carried out under an Institutional Review Board (IRB)-approved protocol. The cell lines were cultured in DMEM (ATCC) supplemented with 10% FBS, or in RPMI (ATCC) supplemented with 15% FBS.

SHP2 Inhibition Enhances the Inhibition of ALK-Rearranged NSCLC Cell Growth by Ceritinib In Vitro—Cell Colony Formation Assays Cell colony formation assays were used to assess cell viability and proliferation after compound treatments. Cells were plated into 6-well tissue culture plates (6×10$^5$ cells/well) in a total volume of 2 mL. After 24 hours, compounds were added to the plates. At the end points of the assays, cells were fixed, stained with crystal violet and photographed.

FIG. 1 shows the photographs obtained from cell colony formation assays with MGH049, MGH045-2A and MGH073-2B cells used to assess the anti-proliferative effect of ceritinib in combination with a SHP2 inhibitor (Compound No. 1). Cells were exposed to ceritinib, Compound No. 1 or the combination for 14 days, and stained with crystal violet. The combination of ALK and SHP2 inhibition led to significant inhibition of cell survival compared with ceritinib alone. Compound No. 1 had no effect on cell growth as a single agent, suggesting that these cell lines are ALK-dependent and signaling via SHP2 functions as a survival pathway or confers resistance to ceritinib. These results suggested that combination of ALK and SHP2 inhibition may either enhance the anti-tumor activity of an ALK inhibitor, particularly ceritinib, and/or overcome ALK inhibitor resistance, particularly ceritinib resistance in ALK-positive cancer, such as NSCLC.

Combination of ALK and SHP2 Inhibition is More Potent in Inhibiting Tumor Growth than Single Agents Alone In Vivo-Xenograft Studies MGH049 and MGH045-2A tumor xenograft models were used to evaluate the efficacy of the combination of an ALK inhibitor with a SHP2 inhibitor in vivo. All animal studies were conducted in accordance with the guidelines as published in the Guide for the Care and Use of Laboratory Animals and Novartis International Animal Care and Use Committee (IACUC) regulations and guidelines. The MGH045-2A cells were harvested during exponential growth. Each athymic female nude mouse (Harlan Laboratories, Indianapolis, IN) was inoculated subcutaneously in the upper right flank with 5×10$^6$ NB-1 cells suspended in 0.2 mL cold PBS. The development of MGH049 xenograft tumors comprised 2 steps. In the first step, 1×10$^7$ MGH049 cells harvested during exponential growth were suspended in a 1:1 mixture of cold PBS and Matrigel (BD Biosciences, San Jose, CA) in a total volume of 0.2 mL, and injected subcutaneously into the upper right flank of nude mice. Tumors established in this step were collected and fragmented. Tumor fragments were then implanted into the upper right flank of nude mice. Tumor volumes were monitored with calipers twice per week. When tumor volume reached approximately 200 mm$^3$, mice were randomized (n=5 per group) and orally administered vehicle, 25 mg/kg ceritinib, 75 mg/kg Compound No. 1 or 25 mg/kg ceritinib plus 75 mg/kg Compound No. 1 daily, respectively.

Figure 2:
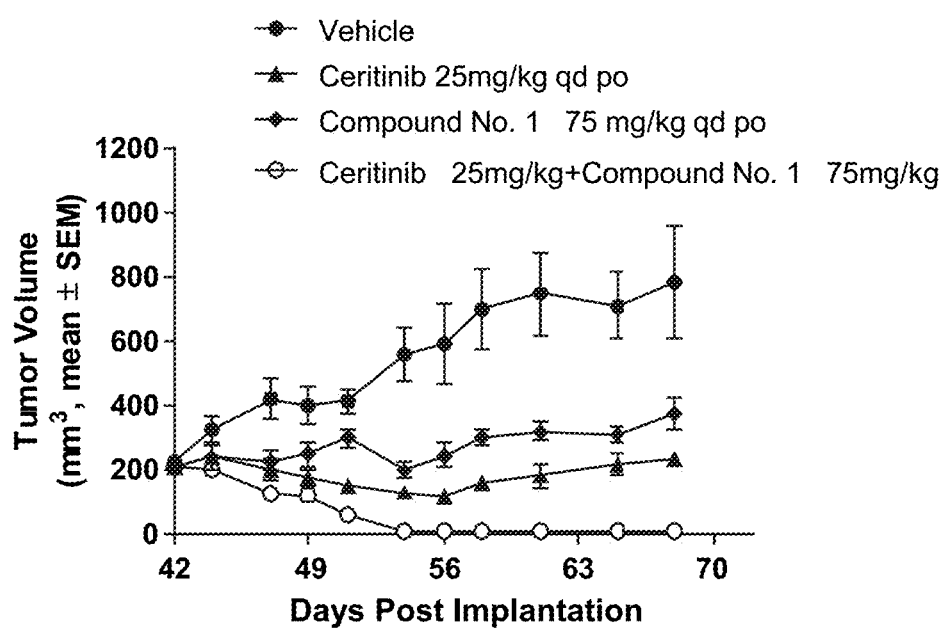
FIG. 2. Plot of the growth inhibition of MGH049 tumor model with ceritinb, Compound No. 1, or the combination of ceritinib and Compound No. 1. The MGH049 cell line was implanted into the flanks of nude mice. Animals were randomized into 4 groups when the average tumor volume was 200-300 mm$^3$ and received vehicle, ceritinib (20 mg/kg), Compound No. 1 (75 mg/kg) or both inhibitors in combination. Tumor dimensions and body weights were measured at the time of randomization and twice weekly thereafter for the study duration. Average tumor volume and SEM are shown as a function of time. Data shows the combination of ceritinib and Compound No. 1 is more effective in the inhibition of tumor growth than either compound alone in vivo.
Figure 3:
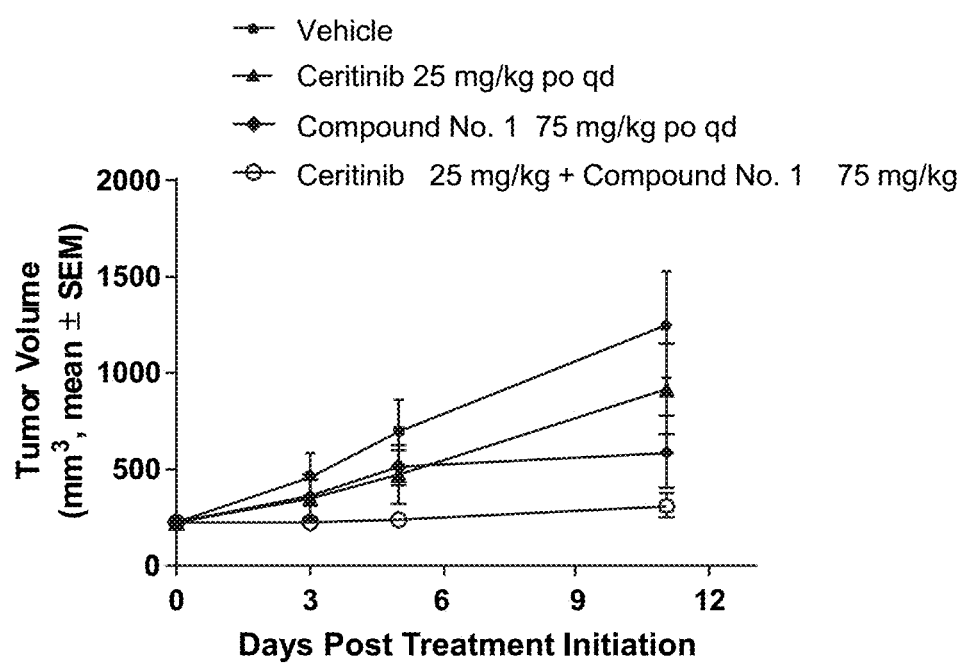
FIG. 3. Plot of the growth inhibition of MGH045-2A tumor model with ceritinb, Compound No. 1, or the combination of ceritinib and Compound No. 1. The MGH045-2A cell line was implanted into the flanks of nude mice. Animals were randomized into 4 groups when the average tumor volume was 200-300 mm³ and received vehicle, ceritinib (20 mg/kg), Compound No. 1 (75 mg/kg) or both inhibitors in combination. Tumor dimensions and body weights were measured at the time of randomization and twice weekly thereafter for the study duration. Average tumor volume and SEM are shown as a function of time. Data shows the combination of ceritinib and Compound No. 1 is more effective in the inhibition of tumor growth than either compound alone in vivo.
Figure 4:
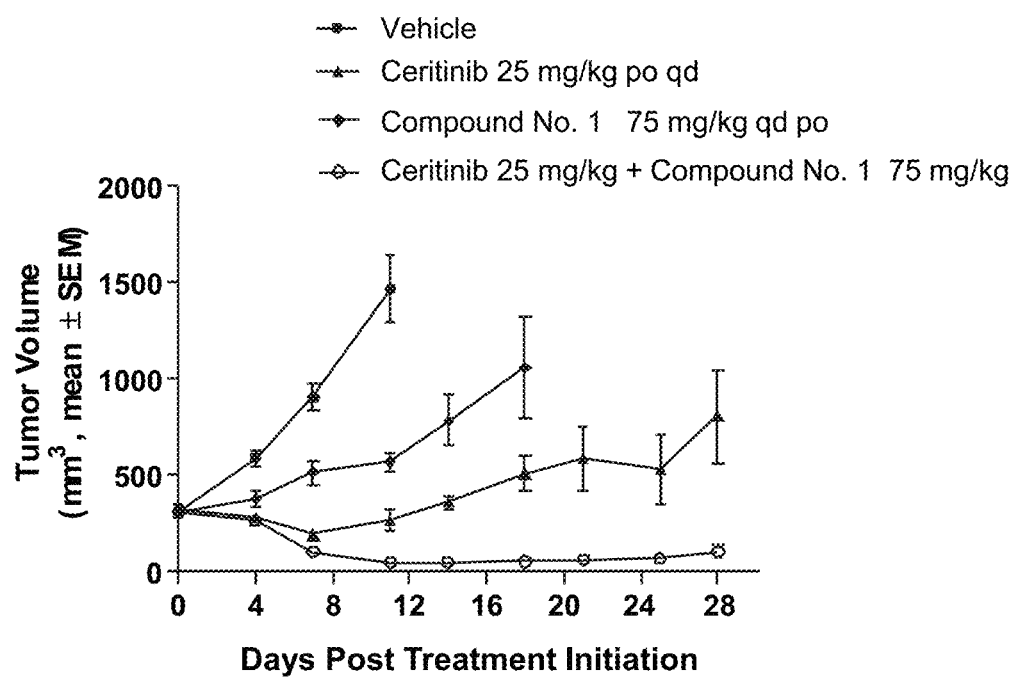
FIG. 4. Plot of the growth inhibition of MGH073-2B tumor model with ceritinb, Compound No. 1, or the combination of ceritinib and Compound No. 1. The MGH073-2B cell line was implanted into the flanks of nude mice. Animals were randomized into 4 groups when the average tumor volume was 200-300 mm³ and received vehicle, ceritinib (20 mg/kg), Compound No. 1 (75 mg/kg) or both inhibitors in combination. Tumor dimensions and body weights were measured at the time of randomization and twice weekly thereafter for the study duration. Average tumor volume and SEM are shown as a function of time. Data shows the combination of ceritinib and Compound No. 1 is more effective in the inhibition of tumor growth than either compound alone in vivo.

FIG. 2 demonstrates that in the MGH049 tumor xenograft model the combination of ceritinib and a SHP2 inhibitor (Compound No. 1) was more effective in the inhibition of tumor growth than either compound alone. FIG. 3 demonstrates that in the MGH045-2A tumor xenograft model the combination of ceritinib and a SHP2 inhibitor (Compound No. 1) was more effective in the inhibition of tumor growth than either compound alone. FIG. 4 demonstrates that in the MGH073-B tumor xenograft model the combination of ceritinib and a SHP2 inhibitor (Compound No. 1) was more effective in the inhibition of tumor growth than either compound alone.

The data shown in FIGS. 1-4 demonstrate that synergistic combination activity for an ALK inhibitor in combination with a SHP2 inhibitor, by way of example ceritinib and Compound No. 1, was observed in both an in vitro cell proliferation assay and an in vivo xenograft study.

It is believed that similar behavior is obtained using the other compounds of Table 1.

SHP2 Inhibition Enhances the Inhibition of ALK-Rearranged NSCLC Cell Growth by Ceritinib In Vitro—Cell Colony Formation Assays-Ceritinib Resistant MGH049 Cells The synergistic combination activity for an ALK inhibitor in combination with a SHP2 inhibitor, by way of example ceritinib, was further demonstrated using a cell colony formation assay with ceritinib resistant MGH049 cells. The cell colony formation assay with ceritinib resistant MGH049 cells were used to assess the anti-proliferative effect of ceritinib in combination with SHP2 inhibitors of Table 1.

Ceritinib resistant MGH049 cells were plated into 12-well tissue culture plates ($2\times10^5$ cells/well) in a total volume of 0.5 mL. After 24 hours, compounds were added to the plates. Cells were exposed for 7 days to either DMSO, ceritinib (0.5 µM), a compound of Table 1 (3 µM), or the combination of ceritinib (0.5 µM) and a compound of Table 1 (3 µM). At the end points of the assays, cells were fixed, stained with crystal violet, and photographed. The crystal violet staining was then extracted in 20% acetic acid and measured as absorbance at 590 nm in duplicates. The absorbance was normalized to the average of six readings in DMSO (without compound) which was set at 100.

Table 3 shows the normalized crystal violet absorbance at 590 nm—obtained with—a compound of Table 1 in DMSO alone or with 0.5 µM ceritinib.

As observed in FIG. 1, the data in Table 3 demonstrates that the combination of ALK and SHP2 inhibition led to significant inhibition of cell survival compared with ceritinib alone in ceritinib-resistant cells. Compound No. 1 had no effect on cell growth as a single agent, suggesting that these cell lines are ALK-dependent and signaling via SHP2 functions as a survival pathway or confers resistance to ceritinib. These results suggested that combination of ALK and SHP2 inhibition may either enhance the anti-tumor activity of an ALK inhibitor, particularly ceritinib, and/or overcome ALK inhibitor resistance, particularly ceritinib resistance in ALK-positive cancer, such as NSCLC.

TABLE 3

| Compound Number | Normalized Crystal Violet abs. (590 nm) DMSO | Normalized Crystal Violet abs. (590 nm) 0.5 µM ceritinib |
| --- | --- | --- |
| No compound | 100 +/− 7 | 35 +/− 3 |
| 1 | 117 +/− 1.4 | 30.1 +/− 0.1 |
| 2 | 67 +/− 0.3 | 10.3 +/− 0.25 |
| 3 | 90.2 +/− 0.8 | 27.6 +/− 0.7 |
| 4 | 97.1 +/− 1.6 | 23.9 +/− 0.5 |
| 5 | | |
| 6 | 44.5 +/− 0.2 | 5.4 +/− 0.1 |
| 7 | 98.2 +/− 2.9 | 20 +/− 0.3 |
| 8 | 99.9 +/− 2.1 | 35.2 +/− 0.7 |
| 9 | 118 +/− 1.6 | 32.1 +/− 1.1 |
| 10 | n/d | n/d |
| 11 | 58.9 +/− 0.35 | 6.4 +/− 0.18 |
| 12 | 30.1 +/− 0.13 | 6.7 +/− 0.072 |
| 13 | 42.8 +/− 0.46 | 6.8 +/− 0.11 |
| 14 | 51.2 +/− 0.053 | 8.1 +/− 0.091 |
| 15 | 31 +/− 0.61 | 6.1 +/− 0.14 |
| 16 | 34.4 +/− 0.38 | 6.6 +/− 0.09 |
| 17 | 29.4 +/− 0.41 | 5.3 +/− 0.067 |
| 18 | 32.3 +/− 1.04 | 5.4 +/− 0.043 |
| 19 | 96.1 +/− 0.18 | 12 +/− 0.11 |
| 20 | 54.7 +/− 0.34 | 7.2 +/− 0.043 |
| 21 | 48.2 +/− 0.61 | 6.0 +/− 0.024 |
| 22 | 19.5 +/− 0.26 | 5.6 +/− 0.40 |
| 23 | 34.8 +/− 0.13 | 5.0 +/− 0.038 |
| 24 | 43.5 +/− 0.32 | 6.2 +/− 0.16 |
| 25 | 52.5 +/− 0.61 | 6.7 +/− 0.11 |
| 26 | n/d | n/d |
| 27 | 37.8 +/− 0.043 | 6.6 +/− 0.15 |
| 28 | 28.1 +/− 0.35 | 5.4 +/− 0.20 |
| 29 | 25.1 +/− 0.086 | 5.4 +/− 0.21 |
| 30 | 39.4 +/− 0.47 | 5.8 +/− 0.077 |
| 31 | 36.4 +/− 0.55 | 6.5 +/− 0.23 |
| 32 | 58.2 +/− 0.26 | 7.9 +/− 0.22 |
| 33 | 73.3 +/− 0.69 | 8.1 +/− 0.2 |
| 34 | 43.6 +/− 0.70 | 7.2 +/− 0.17 |
| 35 | 32.2 +/− 0.048 | 5.4 +/− 0.24 |
| 36 | 23.8 +/− 0.48 | 5.4 +/− 0.20 |
| 37 | 45 +/− 0.52 | 5.5 +/− 0.15 |
| 38 | 83.9 +/− 1.6 | 25.8 +/− 0.17 |
| 39 | 97.9 +/− 0.14 | 24.5 +/− 0.40 |
| 40 | 22.4 +/− 0.51 | 5.7 +/− 0.019 |
| 41 | 25.3 +/− 1.4 | 5.2 +/− 0.058 |
| 42 | 51.7 +/− 0.014 | 8.5 +/− 0.25 |
| 43 | 95.6 +/− 0.058 | 20.2 +/− 0.55 |
| 44 | 37.0 +/− 0.68 | 7.7 +/− n/a |
| 45 | 12.1 +/− 0.024 | 6.0 +/− 0.16 |
| 46 | 70.9 +/− 0.76 | 12.9 +/− 0.31 |
| 47 | 14.8 +/− 0.1 | 6.5 +/− 0.038 |
| 48 | 52.3 +/− 0.13 | 6.8 +/− 0.25 |
| 49 | 26.5 +/− 0.25 | 5.3 +/− 0.23 |
| 50 | 98.9 +/− 0.077 | 9.7 +/− 0.33 |
| 51 | 94 +/− 0.65 | 29.7 +/− 0.37 |
| 52 | 67.9 +/− 1.0 | 21.8 +/− 0.33 |
| 53 | 46.5 +/− 0.55 | 19.6 +/− 3.0 |
| 54 | 132.4 +/− 0.65 | 32.5 +/− 0.69 |

Note:
n/d = not determined

The invention claimed is:

1. A method of treating a cancer in a subject, comprising administering to said subject a therapeutically effective amount of:

(i) an ALK inhibitor or a pharmaceutically acceptable salt thereof, wherein the ALK inhibitor is ceritinib, and (ii) a SHP2 inhibitor or a pharmaceutically acceptable salt thereof, wherein the SHP2 inhibitor is selected from the group consisting of:

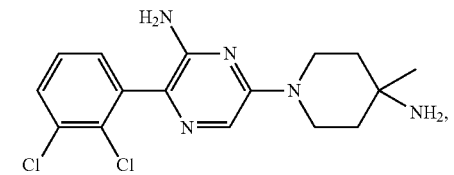

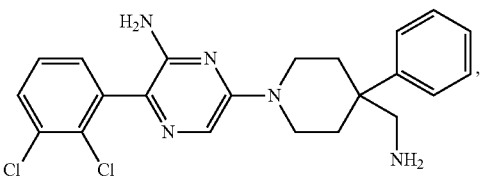

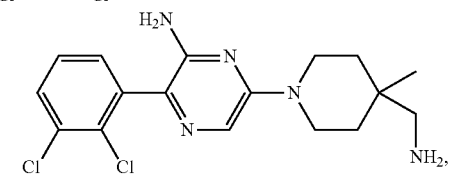

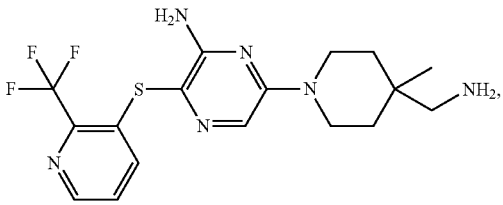

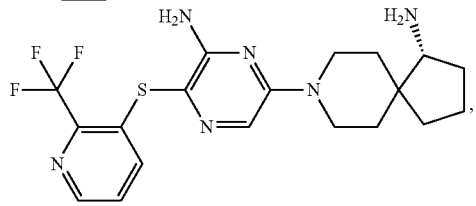

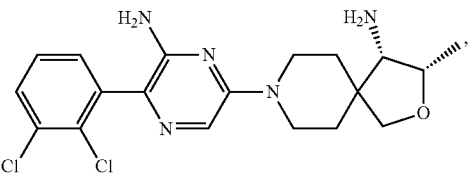

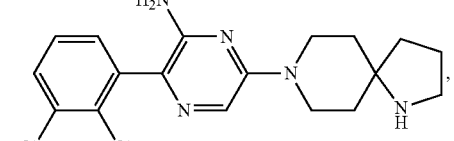

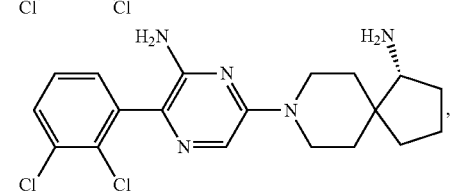

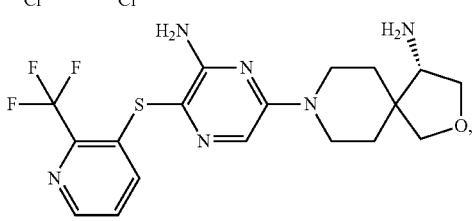

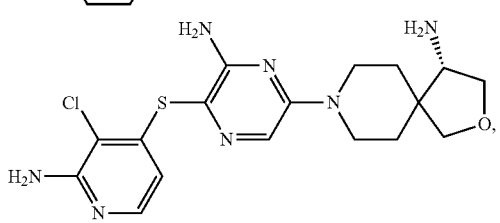

-continued

75
-continued
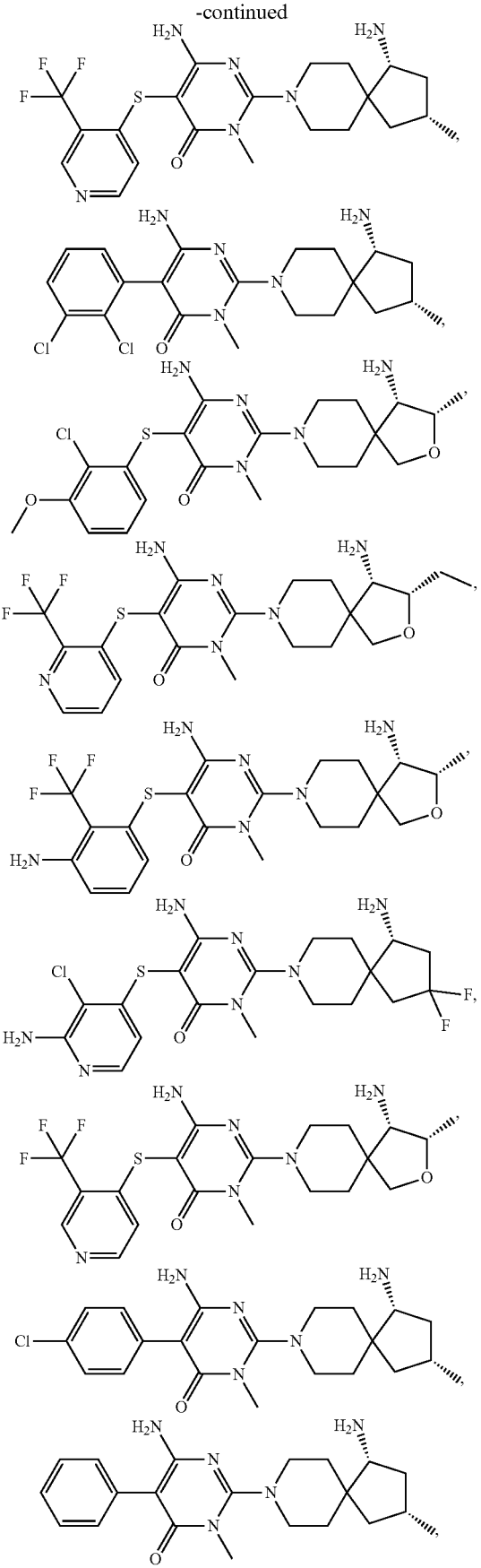
76
-continued
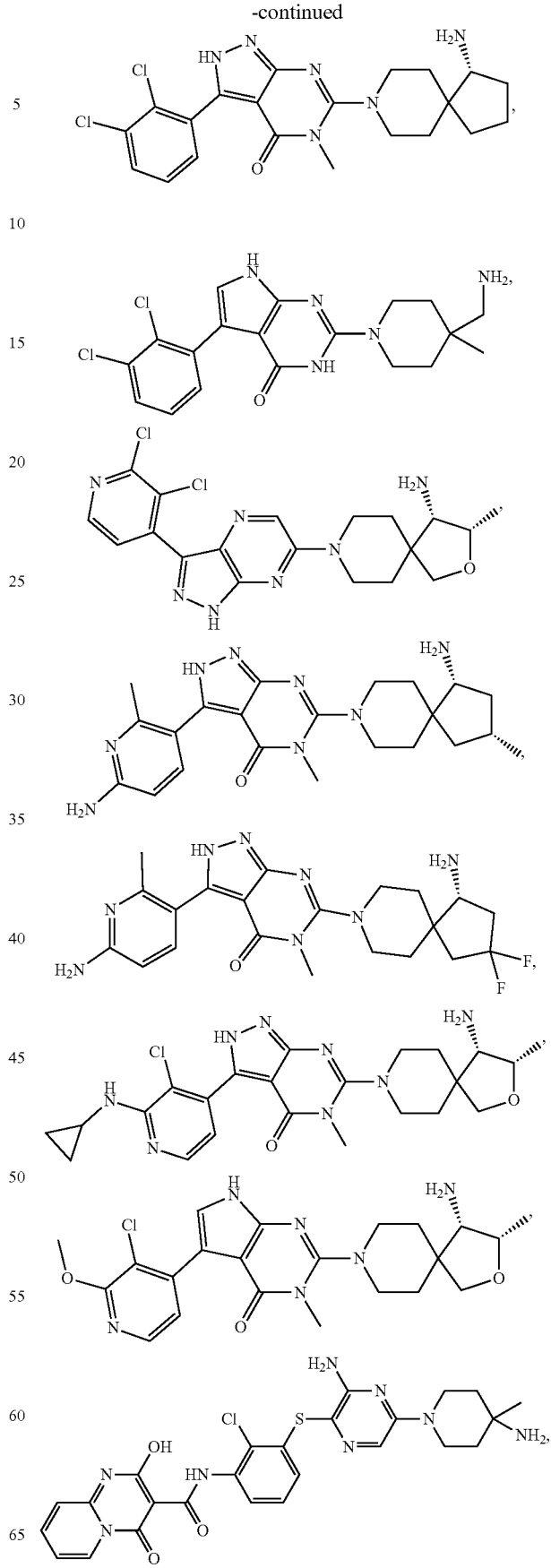

-continued

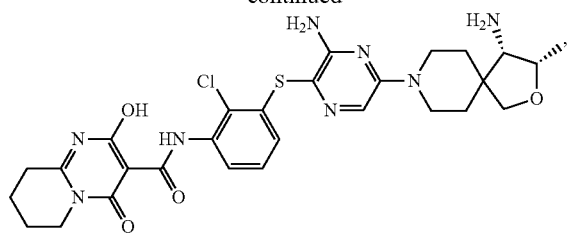

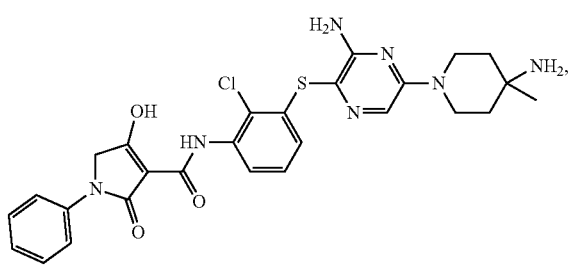

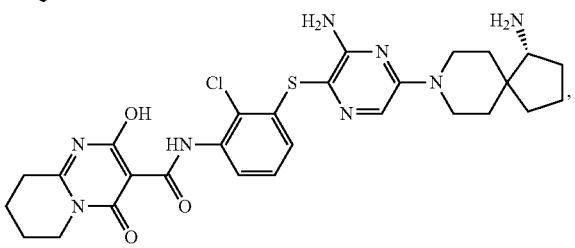

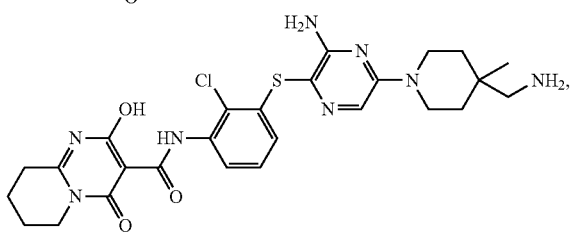

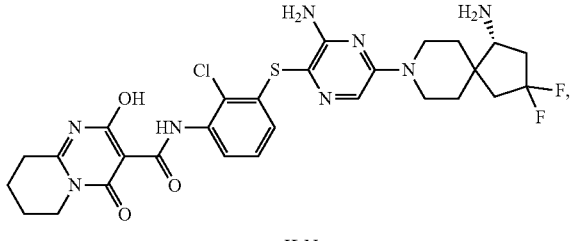

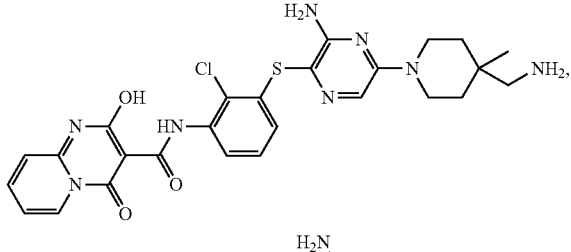

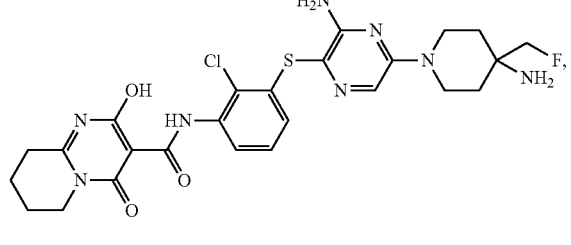

-continued

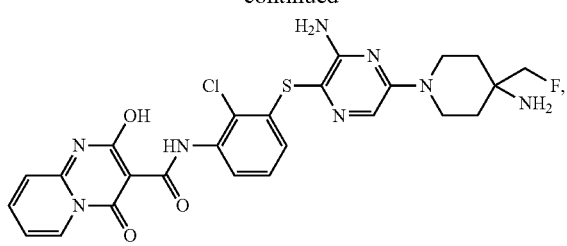

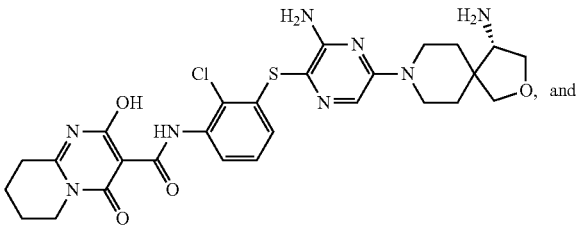

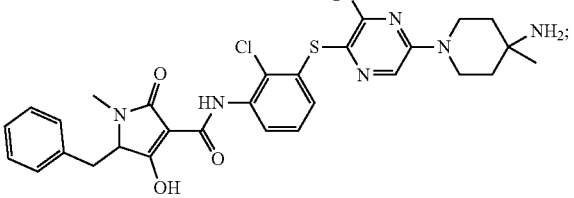, and

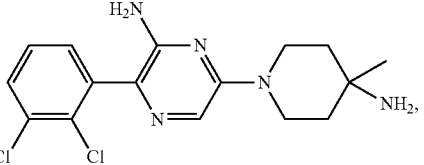

wherein the cancer is an ALK-positive cancer selected from anaplastic large-cell lymphoma, gastric cancer, breast cancers, oesophageal cancer, colorectal cancer, neuroblastoma, inflammatory myofibroblastic tumor, renal cancer, pancreatic cancer and lung cancer.

2. The method of claim 1, wherein the wherein the SHP2 inhibitor is selected from the group consisting of:

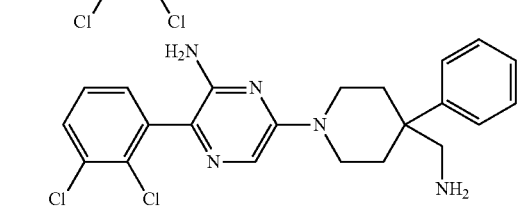

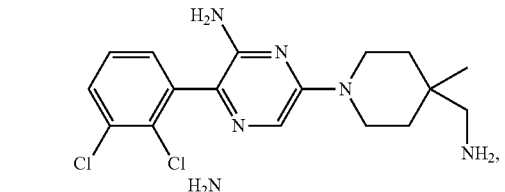

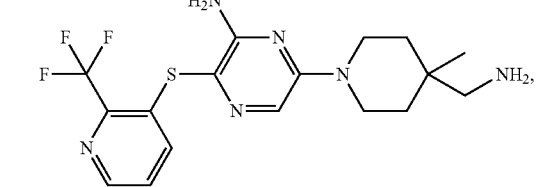

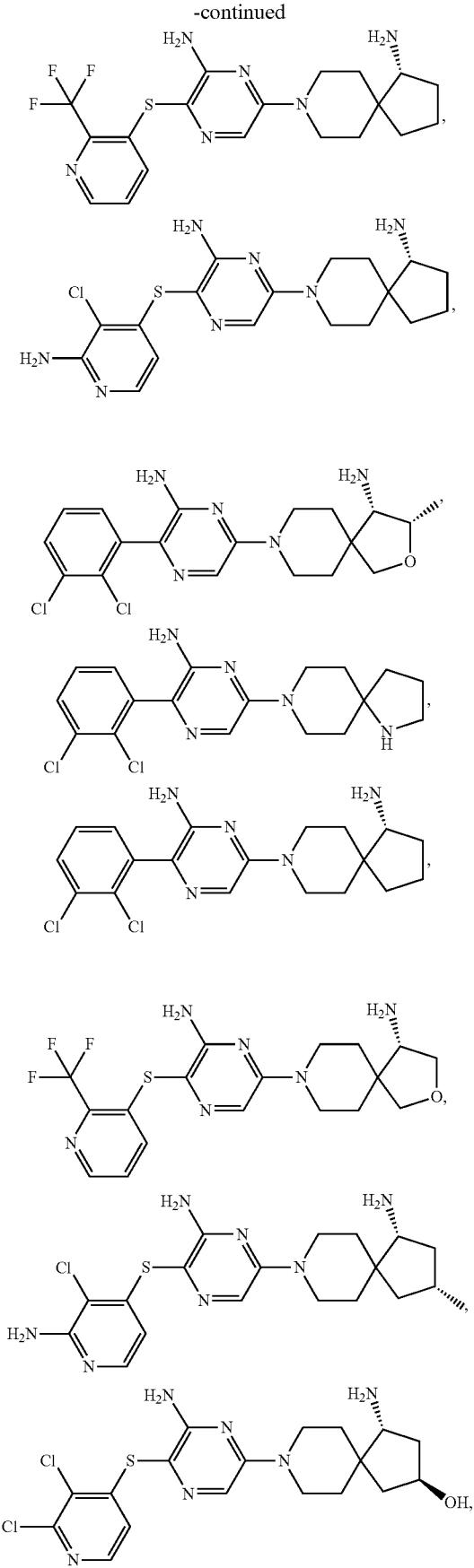
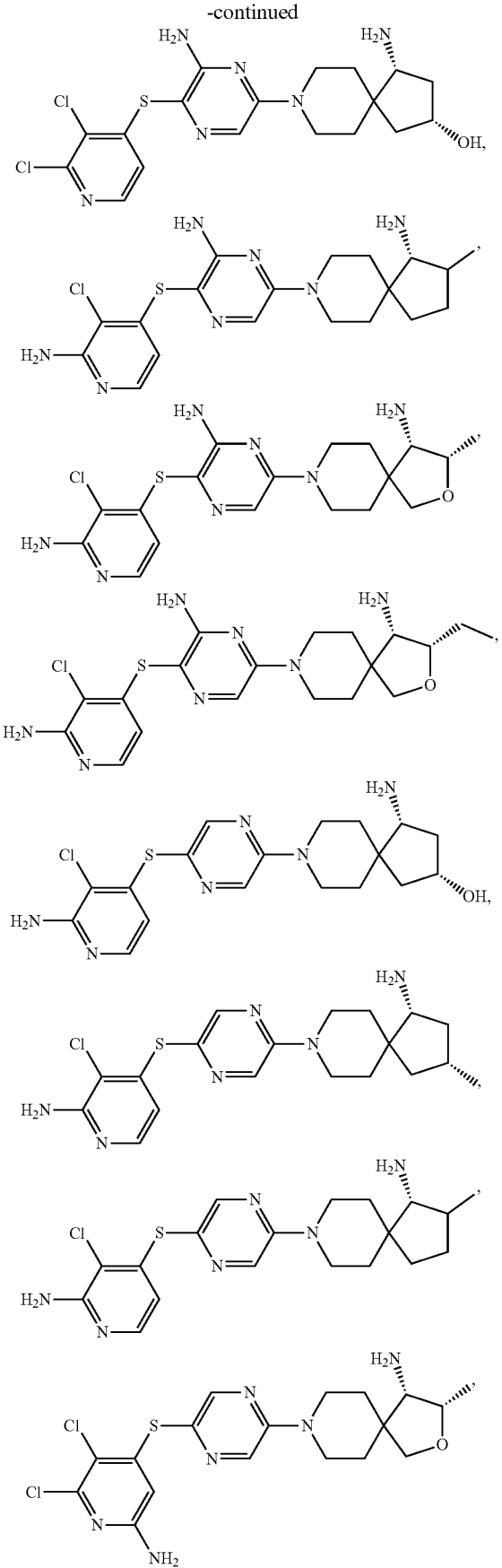

-continued

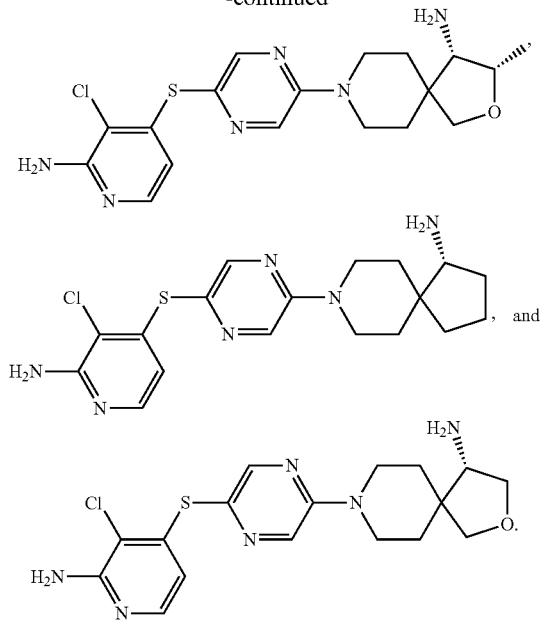

, and

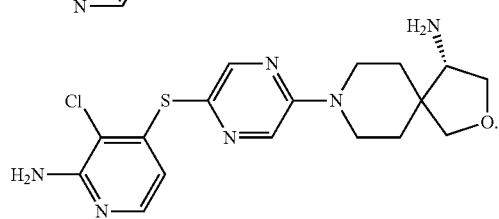

3. The method of claim 2, wherein the wherein the SHP2 inhibitor is

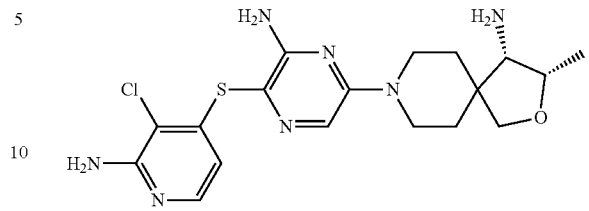

4. The method of claim 1, wherein the cancer is ALK-positive cancer resistant to an ALK inhibitor alone.

5. The method of claim 1, wherein the cancer is ALK-positive cancer characterized by ALK-independent resistance to an ALK inhibitor alone.

6. The method of claim 1, wherein the ALK-positive cancer is lung cancer.

7. The method of claim 6, wherein the ALK-positive cancer is non-small cell lung cancer (NSCLC).

* * * * *